US006646013B1

(12) United States Patent
Barker et al.

(10) Patent No.: US 6,646,013 B1
(45) Date of Patent: Nov. 11, 2003

(54) NUTRIENT FORMULATIONS FOR DISEASE REDUCTION

(75) Inventors: Anna D. Barker, Portland, OR (US); Robert W. Day, Seattle, WA (US); Anthony J. Dennis, Portland, OR (US); Norman R. Farnsworth, Downers Grove, IL (US); Julie A. Haack, Eugene, OR (US); Joseph M. McCord, Denver, CO (US); John D. Potter, Seattle, WA (US)

(73) Assignee: Nutri-Logics, San Fransisco, CA (US)

( * ) Notice: Subject to any disclaimer, the term of this patent is extended or adjusted under 35 U.S.C. 154(b) by 0 days.

(21) Appl. No.: 09/596,036

(22) Filed: Jun. 15, 2000

Related U.S. Application Data

(60) Provisional application No. 60/139,347, filed on Jun. 15, 1999.

(51) Int. Cl.$^7$ ...................... A61K 31/05; A61K 31/075; A61K 31/505; A61K 31/50; A61K 31/70
(52) U.S. Cl. ...................... 514/731; 514/730; 514/728; 514/717; 514/678; 514/725; 514/258; 514/248; 514/458; 514/562; 514/25
(58) Field of Search .............................. 514/458, 562, 514/731, 730, 25, 728, 717, 678, 725, 258, 248

(56) References Cited

U.S. PATENT DOCUMENTS

| | | | |
|---|---|---|---|
| 5,157,030 A | * 10/1992 | Galat et al. | |
| 5,171,571 A | * 12/1992 | Stephen et al. | 424/195.1 |
| 5,430,049 A | * 7/1995 | Gaut et al. | |
| 5,565,211 A | 10/1996 | Rossi | |
| 5,643,623 A | * 7/1997 | Schmitz et al. | 426/73 |
| 5,679,864 A | * 10/1997 | Krackov et al. | |
| 5,954,640 A | 9/1999 | Szabo | |

FOREIGN PATENT DOCUMENTS

| | | | |
|---|---|---|---|
| EP | 0514451 B1 | * 1/1997 | A23L/1/302 |
| WO | WO-98/56397 A1 | * 12/1998 | A61K/35/78 |
| WO | WO 99 18814 A | 4/1999 | |

OTHER PUBLICATIONS

World Health Organization and the International Agency for the Research of Cancer, Carotenoids. IARC Handbooks of Cancer Prevention. vol. 2. 1998, Lyon, France: International Agency for Research on Cancer. p. 326. (Ref. 29).

De Flora, S., et al., Inhibition of urethan–induced lung tumors in mice by dietary N–acetylcysteine. Cancer Lett, 1986. 32(3): p. 235–41. (Ref. 79).

Toda, S., et al., Natural antioxidants. III. Antioxidative components isolated from rhizome by Curcumalonga L. Chem Pharm Bull (Tokyo), 1985. 33(4): p. 1725–8. (Ref. 112).

Shalini, V.K. and L. Srinivas, Lipid peroxide induced DNA damage: protection by turmeric (Curcuma longa). Mol Cell Biochem, 1987. 77(1): p. 3–10. (Ref. 131).

Xu, Y.X., et al., Curcumin inhibits IL1 alpha and TNF–alpha induction of AP–1 and NF–κB DNA–binding activity in bone marrow stromal cells. Hematopathol Mol Hematol, 1997. 11(1): p. 49–62. (Ref. 147).

Non–Steroidal Anti–Inflammatory Drugs. IARC Handbooks of Cancer Prevention. vol. 1. 1997, Lyon: International Agency for Research on Cancer. (Cover, copyright page, table of contents). (Ref. 321).

Mattia De G et al.: "Reduction of Oxidative Stress by Oral–N–Acetyl–L–Cysteine Treatment decreases plasma soluble vascular cell adhesion Molecule–1 concentrations in non–obese, non–dyslipidaemic, normotensive, patients with non–insulin–dependent diabetes" Diabetologia, Berlin, DE, vol. 41, No. 11, 1998, pp. 1392–1396, XP000870074.

KJ Helzlsouer et al.: "Summary of the round table discussion on strategies for cancer prevention: diet. food. additives, supplements and drugs" Cancer Research (Suppl). vol. 54. (Apr. 1, 1994), pp. 2044s–2051s, XP001118315.

Krishnan K., Ruffin MT, Brenner DE: "Colon cancer chemoprevention: clinical development of aspirin as a chemopreventive agent" Journel of Cellular Biochemistry Supplements, vol. 28–29, 1997 pp. 148–158, XP002230891.

Wargovich MJ: "Experimental evidence for cancer preventive elements in foods" Cancer Letters, vol. 114, 1997, pp. 11–17, XP002230892, Ireland, table I.

Mori H. Tanaka T. Sugie S, Yoshimi N, Kawamori T, Hirose Y, Ohnishi M: "Chemoprevention by naturally occurring and synthetic agents in oral, liver, and large bowel carcinogenesis" Journal of Cellular Biochemistry Supplements, vol. 27, 1997, pp. 35–41, XP002230893 USA.

Huang MT, Newmark HL, Frenkel K: "Inhibitory effects of curcumin on tumorigenesis in mice" Journal of Cellular Biochemistry Supplements, vol. 27, 1997, pp. 26–34, XP002230894 USA.

Copy of Supplementary Partial European Search Report included in communication from EPO on Mar. 18, 2003.

World Cancer Research Fund (WCRF), Food, Nutrition and the Prevention of Cancer: a Global Perspective. 1997, Menasha: American Institute for Cancer Research. p. 426. (Ref. 1).

Steinmetz, K.A. and J.D. Potter, Vegetables, fruit, and cancer prevention: a review. J Am Diet Assoc, 1996. 96(10): p. 1027–39. (Ref. 2).

(List continued on next page.)

Primary Examiner—Sreeni Padmanabhan
Assistant Examiner—S. Jiang
(74) Attorney, Agent, or Firm—Baker & Daniels

(57) ABSTRACT

The instant invention provides a combination of multiple nutrients useful to reduce colon rectal cancer in a mannalian or human subject. Further, the combination provides synergistic ratios of the useful nutrients.

12 Claims, 5 Drawing Sheets

OTHER PUBLICATIONS

Hercberg, S., et al., Background and rationale behind the SU.VI.MAX Study, a prevention trial using nutritional doses of a combination of antioxidant vitamins and minerals to reduce cardiovascular diseases and cancers. SUpplementation ent Vitamines et Mineraux AntioXydants Study. Int J Vitam Nutr Res, 1998.68(1): p. 3–20.

Block, G., B. Patterson, and A. Subar, Fruit, vegetables, and cancer prevention: a review of the epidemiological evidence. Nutr Cancer, 1992. 18(1): p. 1–29. (Ref. 5).

Byers, T. and N. Guerrero, Epidemiologic evidence for vitamin C and vitamin E in cancer prevention. Am J Clin Nutr, 1995. 62(Suppl): p. 1385S–1392S. (Ref. 6).

van Poppel, G. and R.A. Goldbohm, Epidemiologic evidence for beta–carotene and cancer prevention. Am J Clin Nutr, 1995. 62(6 Suppl): p. 1393S–1402S. (Ref. 7).

Block, G., Vitamin C and cancer prevention: the epidemiologic evidence. Am J Clin Nutr, 1991. 53(Suppl): p. 270S–282S. (Ref. 8).

Greenwald, P., NCI Cancer prevention and control research. Preventive Med, 1993. 22: p. 642–660. (Ref. 9).

Nowell, P.C., The clonal evolution of tumor cell populations. Science, 1976. 194(4260): p. 23–8. (Ref. 10).

Weinstein, I.B., et al., Molecular mechanisms of mutagenesis and multistage carcinogenesis, in The Molecular Basis of Cancer, J. Mendelsohn, et al., Editors. 1995, W.B. Saunders: Philadelphia. p. 59–85. (Ref. 11).

Anzano, M.A., et al., Prevention of breast cancer in the rat with 9–cis–retinoic acid as a single agent and in combination with tamoxifen. Cancer Res, 1994. 54(17): p. 4614–7. (Ref. 13).

Anzano, M.A., et al., Chemoprevention of mammary carcinogenesis in the rat: combined use of raloxifene and 9–cis–retinoic acid. J Natl Cancer Inst, 1996. 88(2): p. 123–5. (Ref. 14).

Ratko, T.A., et al., Chemoprevention of MNU–induced mammary tumors in the mature rat by 4–HPR and tamoxifen. Anticancer Res, 1992. 12(4): p. 1147–53. (Ref. 16).

Lucia, M.S., et al., Chemopreventive activity of tamoxifen, N–(4–hydroxyphenyl)retinamide, and the vitamin D analogue Ro24–5531 for androgen–promoted carcinomas of the rat seminal vesicle and prostate. Cancer Res, 1995. 55(23): p. 5621–7. (Ref. 17).

Reddy, B.S., et al., Chemoprevention of colon carcinogenesis by concurrent administration of piroxicam, a nonsteroid antiinflammatory drug with D,L–alpha–difluoromethylornithine, an ornithine decarboxylase inhibitor, in diet. Cancer Res, 1990. 50(9): p. 2562–8. (Ref. 18).

Kelloff, G.J., et al., Mechanistic considerations in chemopreventive drug development. J Cell Biochem Suppl, 1994. 20: p. 1–24. (Ref. 19).

Kelloff, G.J., et al., Inhibition of chemical carcinogenesis, in Chemical Induction of Cancer. Modulation of Combination Effects, J.C. Arcos, M.F. Argus, and Y. Woo, Editors. 1995, Birkhauser: Boston, p. 73–122. (Ref. 20).

Prasad, K.N., W. Cole, and P. Hovland, Cancer prevention studies: past, present, and future directions. Nutrition, 1998. 14(2): p. 197–210; discussion 237–8. (Ref. 21).

Free Radicals in Biology and Medicine. 2nd ed, ed. B. Halliwall and J.M.C. Gutteridge. 1989, Oxford, UK: Clarendon Press. (Ref. 22).

McCord, J.M., Human disease, free radicals, and the oxidant/antioxidant balance. Clin Biochem, 1993. 26(5): p. 351–7. (Ref. 23).

McCord, J., The Importance of Oxidant–Antioxidant Balance, in Oxidative Stress, Cancer, AIDS, and Neurogenerative Diseases, L. Montagnier, R. Olivier, and C. Pasquier, Editors. 1996. Marcel Dekker: New York. p. 1–6. (Ref. 24).

Jacob, R.A., et al., Vitamin C, in Modern Nutrition in Health and Disease, M.E. Shils, J.A. Olson, and M. Shike, Editors. 1993, Lea and Febiger: Philadelphia. p. 432–48. (Ref. 25).

Huang, M.T., et al., Inhibitory effects of dietary curcumin on forestomach, duodenal, and colon carcinogenesis in mice. Cancer Res, 1994. 54(22): p. 5841–7. (Ref. 26).

Kuroda, Y. and Y. Hara, Antimutagenic and anticarcinogenic activity of tea polyphenols. Mutat Res, 1999. 436(1): p. 69–97. (Ref. 27).

Wang, Z.Y., et al., Inhibitory effects of black tea, green tea, decaffeinated black tea, and decaffeinated green tea on ultraviolet B light–induced skin carcinogenesis in 7,12–dimethylbenz[1]anthracene–initiated SKH–1 mice. Cancer Res. 1994. 54(13): p. 3428–35. (Ref. 28).

Bjorneboe, A., G.E. Bjorneboe, and C.A. Drevon, Absorption, transport and distribution of vitamin E. J Nutr, 1990. 120(3): p. 233–42. (Ref. 30).

Machlin, L.J. and A. Bendich, Free radical tissue damage: protective role of antioxidant nutrients. Faseb J, 1987. 1(6): p. 441–5. (Ref. 31).

Tappel, A.L., Vitamin E and selenium protection from in vivo lipid peroxidation. Ann N Y Acad Sci, 1980. 355: p. 18–31. (Ref. 32).

Ames, B.N., Dietary carcinogenesis and anticarcinogens. Oxgen radicals and degenerative diseases. Science, 1983. 221(4617): p. 1256–64. (Ref. 33).

Knekt, P., Role of vitamin E in the prophylaxis of cancer. Ann Med, 1991. 23(1): p. 3–12. (Ref. 34).

Blot, W.J., et al., Nutrition intervention trials in Linxian, China: supplementation with specific vitamin/mineral combinations, cancer incidence, and disease–specific mortality in the general population. J Natl Cancer Inst, 1993. 85(18): p. 1483–92. (Ref. 35).

Bostick, R.M., et al., Reduced risk of colon cancer with high intake of vitamin E: the Iowa Women's Health Study. Cancer Res, 1993. 53(18): p. 4203–7. (Ref. 36).

The effect of vitamin E and beta carotene on the incidence of lung cancer and other cancers in male smokers. The Alpha–Tocopherol, Beta Carotene Cancer Prevention Study Group. N Engl J Med, 1994. 330(15): p. 1029–35. (Ref. 37).

Ohshima, H., J.C. Bereziat, and H. Bartsch, Monitoring N–nitrosamino acids relaxed in the urine and feces of rats as an index for endodgenous nitrosation. Carcinogenesis, 1982. 3(1): p. 115–20. (Ref. 38).

Hennekens, C.H., J.E. Buring, and R. Peto, Antioxidant vitamins—benefits not yet proved. N Engl J Med, 1994. 330(15): p. 1081–1. (Ref. 39).

Kelloff, G.J., et al., Clinical development plan: vitamin E. J Cell Biochem Suppl, 1994. 20: p. 282–99. (Ref. 40).

Cadenas, E. and L. Packer, Handbook of antioxidants. Antioxidants Health Dis, 1996. 3: p. 1–602. (Ref. 41).

Buettner, G.R., The pecking order of free radicals and antioxidants: lipid peroxidation, alpha–tocopherol, and ascorbate. Arch Biochem Biophys, 1993. 300(2): p. 535–43. (Ref. 42).

Niki, E., Vitamin C as an antioxidant. World Rev Nutr Diet, 1991. 64: p. 1–30. (Ref. 43).

Sharma, M.K. and G.R. Buettner, Interaction of vitamin C and vitamin E during free radical stress in plasma: an ESR study. Free Radic Biol Med, 1993. 14(6): p. 649–53. (Ref. 44).

Buettner, G.R. and B.A. Jurkiewicz, Ascorbate free radical as a marker of oxidative stress: an EPR study: Free Radic Biol Med, 1993. 14(1): p. 49–55. (Ref. 45).

Golumbic, C. and H.A. Mattill, Antioxidants and the autoxidation of fats XIII: the antioxygenic action of ascorbic acid in association with tocopherols, hydroquinones, and related compounds. J Am Chem Soc, 1941. 63: p. 1279–80. (Ref. 47).

Shamberger, R.J. and D.V. Frost, Possible protective effect of selenium against human cancer. Can Med Assoc J, 1969. 100(14): p. 682. (Ref. 48).

Shamberger, R.J. and C.E. Willis, Selenium distribution and human cancer mortality. CRC Crit Rev Clin Lab Sci, 1971. 2(2): p. 211–21. (Ref. 49).

Schrauzer, G.N., D.A. White, and C.J. Schneider, Cancer mortality correlation studies—III: statistical associations with dietary selenium intakes. Bioinorg Chem, 1977. 7(1): p. 23–31. (Ref. 50).

Yu, S. Y., et al., Regional variation of cancer mortality incidence and its relation to selenium levels in China. Biol Trace Elem Res, 1985: 7: p. 21–29. (Ref. 51).

Combs, G.F., Jr., Selenium and cancer, in Antioxidants and Disease Prevention, H. Garewal, Editor. 1997. CRC Press: New York. p. 97–113. (Ref. 52).

Clark, L.C., et al., Plasma selenium concentration predicts the prevalence of colorectal adenomatous polyps. Cancer Epidemiol Biomarkers Prev, 1993. 2(1): p. 41–6. (Ref. 53).

Salonen, J.T., et al., Association between serum selenium and the risk of cancer. Am J Epidemiol, 1984. 120(3): p. 342–9. (Ref. 54).

Willett, W.C., et al., Prediagnostic serum selenium and risk of cancer. Lancet, 1983. 2(8342): p. 130–4. (Ref. 55).

Helzlsouer, K.J., G.W. Comstock, and J.S. Morris, Selenium, lycopene alpha–tocopherol, beta–carotene, retinol, and subsequent bladder cancer, Cancer Res, 1989. 49(21): p. 6144–8. (Ref. 56).

Kok, F.J., et al., Is serum selenium a risk factor for cancer in men only?. Am J Epidemiol, 1987. 125(1): p. 12–6. (Ref. 57).

van den Brandt, P.A., et al., A prospective cohort study on toenail selenium levels and risk of gastrointestinal cancer. J Natl Cancer Inst, 1993. 85(3): p. 224–9. (Ref. 58).

van den Brandt, P.A., et al., A prospective cohort study on selenium status and the risk of lung cancer. Cancer Res, 1993. 53(20): p. 4860–5. (Ref. 59).

Helzlsou

Clark, L.C., et al., Effects of selenium supplementation for cancer prevention in patients with carcinoma of the skin. A randomized controlled trial. Nutritional Prevention of Cancer Study Group. JAMA, 1996. 276(24): p. 1957–63. (Ref. 62).

Combs, G.F., Jr. and W.P. Gray, Chemopreventive agents: selenium. Pharmacol Ther, 1998. 79(3): p. 179–92. (Ref. 63).

Rotruck, J.T., et al., Selenium: biochemical role as a component of glutahione peroxidase. Science, 1973. 179(73): p. 588–90. (Ref. 64).

Burk, R.F., Molecular biology of selenium with implications for its metabolism. Faseb J, 1991. 5(9): p. 2274–9. (Ref. 65).

Stadtman, T.C., Selenocysteine. Annu Rev Biochem, 1996. 65: p. 83–100. (Ref. 66).

Arthur, J.R. and G.J. Beckett, New metabolic roles for selenium. Proc Nutr Soc, 1994. 53(3): p. 615–34. (Ref. 67).

Sunde, R.A., Molecular biology of selenoproteins. Annu Rev Nutr, 1990. 10: p. 451–74. (Ref. 68).

Kohrle, J., Thyroid hormone deiodination in target tissues—a regulatory role for the trace element selenium? Exp Clin Endocrinol, 1994. 102(2): p. 63–89. (Ref. 69).

Taylor, E.W., Selenium and cellular immunity. Evidence that selenoproteins may be encoded in the +1 reading frame overlapping the human CD4, CD8, and HLA–DR genes. Biol Trace Elem Res, 1995. 49(2–3): p. 85–95. (Ref. 70).

Roy, M., et al., Supplementation with selenium restores age–related decline in immune cell function. Proc Soc Exp Biol Med, 1995. 209(4): p. 369–75. (Ref. 71).

Shan, X.Q., T.Y. Aw, and D.P. Jones, Glutathione–dependent protection against oxidative injury. Pharmacol Ther, 1990. 47(1): p. 61–71. (Ref. 72).

Thomas, S.H., Paracetamol (acetaminophen) poisoning. Pharmacol Ther, 1993. 60(1): p. 91–120. (Ref. 73).

De Flora, S., et al., Antioxidant activity and other mechanisms of thiols involved in chemoprevention of mutation and cancer. Am J Med, 1991. 91(3C): p. 122S–120S. (Ref. 74).

De Flora, S., G. A. Rossi, and A. De Flora, Metabolic, desmutagenic and anticarcinogenic effects of N–acetylcysteine. Respiration, 1986. 50(Suppl 1): p. 43–9. (Ref. 75).

Izzotti, A., et al., Inhibition by N–acetylcysteine of carcinogen–DNA adducts in the tracheal epithelium of rats exposed to cigarette smoke. Carcinogenesis, 1995. 16(3): p. 669–72. (Ref. 76).

Cesarone, C.F., et al., Differential assay and biological significance of poly(ADP–ribose) polymerase activity in isolated liver nuclei. Mutat Res, 1990. 245(3): p. 157–63. (Ref. 77).

Albini, A., et al., Inhibition of invasion, geletinase activity, tumor take and metastasis of malignant cells by N–acetylcysteine. Int J Cancer, 1995. 61(1): p. 121–9. (Ref. 78).

Cesarone, C.F., et al., Effects of aminothiols in 2–acetylaminofluorene–treated rats. I. Damage and repair of liver DNA, hyperplastic foci, and Zymbal gland tumors. In Vivo, 1987. 1(2): p. 85–92. (Ref. 80).

Wilpart, M., A. Speder, and M. Roberfroid, Anti–initiation activity of N–acetylcysteine in experimental colonic carcinogenesis, Cancer Lett, 1986. 31(3): p. 319–24. (Ref. 81).

Reddy, B.S., et al., Chemoprevention of colon carcinogenesis by organosulfur compounds. Cancer Res, 1993. 53(15): p. 3493–8. (Ref. 82).

Cianfriglia, F., et al. Minerva Stomatol, 1994. 43(6): p. 255–61. (Ref. 83).

De Vries, N. and S. De Flora, N–acetyl–l–cysteine. J Cell Biochem Suppl, 1993: p. 270–7. (Ref. 84).

Issels, R.D., et al., Promotion of cystine uptake and its utilization for glutathione biosynthesis induced by cysteamine and N–acetylcysteine. Biochem Pharmacol, 1988. 37(5): p. 881–8. (Ref. 85).

De Flora, S., et al., In vivo effects of N–acetylcysteine on glutathione metabolism and on the biotransformation of carcinogenic and/or mutagenic compounds. Carcinogenesis, 1985. 6(12): p. 1735–45. (Ref. 86).

Nakata, K., et al., Effects of age of levels of cysteine, glutathione and related enzyme activities in livers of mice and rats and an attempt to replenish hepatic glutathione level of mouse with cysteine derivatives. Mech Ageing Dev, 1996. 90(3): p. 195–207. (Ref. 87).

Hoffer, E., et al., N–acetylcysteine increases the glutathione content and protects rats alveolar type II cells against paraquat–induced cytotoxicity. Toxicol Lett, 1996. 84(1): p. 7–12. (Ref. 88).

Corcoran, G.B. and B.K. Wong, Role of glutathione in prevention of acetimophen–induced hepatotoxicity by N–acetyl–L–cysteine in vivo: studies with N–acetyl–D–cysteine in mice. J Pharmacol Exp Ther, 1986. 238(1): p. 54–61 (Ref. 89).

Cotgreave, I.A., et al., No penetration of orally administered N–acetylcysteine into bronchoalveolar lavage fluid. Eur J Respir Dis, 1987. 70(2): p. 73–7. (Ref. 90).

Bridgeman, M.M., et al., Cysteine and glutathione concentrations in plasma and bronchoalveolar lavage fluid after treatment with N–acetylcysteine. Thorax, 1991. 46(1): p. 39–42. (Ref. 91).

Brurgunder, J.M., A. Varriale, and B.H. Lauterburg, Effect of N–acetylcysteine on plasma cysteine and glutathione following paracetamol administration. Eur J Clin Pharmacol, 1989. 36(2): p. 127–31. (Ref. 92).

Aruoma, O.I., et al., The antioxidant action of N–acetylcysteine: its reaction with hydrogen peroxide, hydroxyl radical, superoxide, and hypochlorous acid. Free Radic Biol Med, 1989. 6(6): p. 593–7. (Ref. 93).

Moldeus, P., I.A. Cotgreave, and M. Berggren, Lung protection by a thiol–containing antioxidant: N–acetylcysteine. Respiration, 1986. 50(Supp 1): p. 31–42. (Ref. 94).

Wagner, P.D., et al., Protection against pulmonary 02 toxicity by N–acetylcysteine. Eur Respir J, 1989. 2(2): p. 116–26. (Ref. 95).

Bonanomi, L. and A. Gazzaniga, Toxicological, pharmacokinetic and metabolix studies on acetylcysteine. Eur J Respir Dis Suppl, 1980. 111: p. 45–51. (Ref. 96).

Marui, N., et al., Vascular cell adhesion molecule–1 (VCAM–1) gene transcription and expression are regulated through and antioxidant–sensitive mechanism in human vascular endothelial cells. J Clin Invest, 1993. 92(4): p. 1866–74. (Ref. 97).

Weber, C., et al., Antioxidants inhibit monocyte adhesion by suppressing nuclear factor–kappa B mobilization and induction of vascular cell adhesion molecule–1 in endothelial cells stimulated to generate radicals. Arterioscler Thromb, 1994. 14(10): p. 1665–73. (Ref. 98).

Faruqi, R., C. de la Motte, and P.E. DiCorleto, Alpha–tocopherol inhibits agonist–induced monocytic cell adhesion to cultured human endothelial cells. J Clin Invest, 1994. 94(2): p. 592–600. (Ref. 99).

Ratan, R.R., T.H. Murphy, and J.M. Baraban, Macromolecular synthesis inhibitors prevent oxidative stress–induced apoptosis in embryonic cortical neurons by shunting cysteine from protein synthesis to glutathione. j Neurosci, 1994. 14(7): p. 4385–92. (Ref. 100).

Rothstein, J.D., et al., Chronic inhibition of superoxide dismutase produces apoptotic deat of spinal neurons. Proc Natl Acad Sci U S A, 1994. 91(10): p. 4155–9. (Ref. 101).

Talley, A.K., et al., Tumor necrosis factor alpha–induced apoptosis in human neuronal cells: protection by the antioxidant N–acetylcysteine and the genes bcl–2 and crmA. Mol Cell Biol, 1995. 15(5): . 2359–66. (Ref. 102).

Abello, P.A., S.A. Fidler, and T.G. Buchman, Thiol reducing agents modulate induced apoptosis in porcine endothelial cells. Shock, 1994. 2(2): p. 79–83. (Ref. 103).

Zamzami, N., et al., Reduction in mitochondrial potential constitutes an early irreversible step of programmed lymphocyte death in vivo. J Exp Med, 1995. 181(5): p. 1661–72. (Ref. 104).

Fang, W., et al., Bcl–xL rescues WEHI 231 B lymphocytes from oxidant–mediated death following diverse apoptotic stimuli. J Immunol, 1995. 155(1): p. 66–75. (Ref. 105).

Miller, L.F. and B.H. Rumack, Clinical safety of high oral doses of acetylcysteine. Semin Oncol, 1983. 10(1 Suppl 1): p. 76–85. (Ref. 106).

Johnston, R.E., H.C. Hawkins, and J.H. Weikel, Jr., The toxicity of N–acetylcysteine in laboratory animals. Semin Oncol, 1983. 10(Supp 1): p. 17–24. (Ref. 107).

Srimal, R.C. and B.N. Dhawan, Pharmacology of diferuloyl methane (curcumin), a non–steroidal anti–inflammatory agent. J Pharm Pharmacol, 1973. 25(6): p. 447–52. (Ref. 108).

Satoskar, R.R., S.J. Shah, and S.G. Shenoy, Evaluation of anti–inflammatory property of curcumin (diferuloyl methane) in patients with postoperative inflammation. Int J Clin Pharmacol Ther Toxicol, 1986. 24(12): p. 651–4. (Ref. 109).

Tonnesen, H.H., Chemistry of curcumin and curcuminoids, in Phenolic Compounds in Food and their Effect of Health, C.–T. Ho, C.Y. Lee, and M.–T. Huang, Editors, 1992, American Chemical Society: Washington, DC. p. 143–153. (Ref. 110).

Sharma, O.P., Antioxidant activity of curcumin and related compounds. Biochem Pharmacol, 1976. 25(15): p. 1811–2. (Ref. 111).

Huang, M.T., et al., Inhibitory effect of curcumin, chlorogenic acid, caffeic acid, and ferulic acid on tumor promotion in mouse skin by 12–O–tetradecanoylphorbol–13–acetate. Cancer Res, 1988: 48(21): p. 5941–6. (Ref. 113).

Huang, M.T., et al., Inhibitory effects of curcumin on tumor initiation by benxo[a]pyrene and 7,12–dimethylbenz[a]anthracene. Carcinogenesis, 1992. 13(11): p. 2183–6. (Ref. 114).

Kawamori, T., et al., Chemopreventive effect of curcumin, a naturally occurring anti–inflammatory agent, during the promotion/progressin stages of colon cancer [In Process Citation]. Cancer Res, 1999. 59(3): p. 597–601. (Ref. 115).

Huang, M.T., et al., Effects of dietary curcumin and ascorbyl palmitate on azoxymethanol–induced colonic epithelial cell proliferation and focal areas of dysplasia. Cancer Lett, 1992. 64(2): p. 117–21. (Ref. 116).

Rao, C.V., B. Simi, and B.S. Reddy, Inhibition by dietary curcumin of azoxymethane–induced ornithine decarboxylase, tyrosine protein kinase, arachidonic acid metabolism and aberrant crypt foci formation in the rat colon. Carcinogenesis, 1993. 14(11): p. 2219–25. (Ref. 117).

Rao, C.V., et al., Chemopreventive of colon carcinogenesis by dietary curcumin, a naturally occurring plant phenolic compound. Cancer Res, 1995. 55(2): p. 259–66. (Ref. 118).

Pereira, M.A., et al., Effects of the phytochemicals, curcumin and quercetin, upon azoxymethane–induced colon cancer and 7,12–dimethylbenz[a]anthracene–induced mammary cancer in rats. Carcinogenesis, 1996. 17(6): p. 1305–11. (Ref. 119).

Nagano, T., et al., New curcuminoids isolated from Zingiber cassumunar protect cells suffering from oxidative stress: a flow–cytometric study using rat thymocytes and H202. Jpn J Pharmacol, 1997. 75(4): p. 363–70. (Ref. 121).

Shih, C.A. and J.K. Lin, Inhibition of 8–hydroxydeoxyguanosine by curcumin in mouse fibroblast cells. Carcinogenesis, 1993. 14(4): p. 709–712. (Ref. 122).

Tonnesen, H.H. and J.V. Greenhill, Studies on curcumin and curcuminoids. XXII: Curcumin as a reducing agent and as a radical scavenger. Int J Pharmaceut, 1992. 87: p. 79–87. (Ref. 123).

Kunchandy, E., Oxygen radical scavenging activity of curcumin. Int J Pharmaceut, 1990. 58: p. 237–240. (Ref. 124).

Zhao, B.L., et al., Scavenging effects of extracts of green tea and natural antioxidants on active oxygen radicals. Cell Biophys, 1989. 14(2): p. 175–185. (Ref. 125).

Reddy, A.C. and B.R. Lokesh, Studies on the inhibitory effects of curcumin and eugenol on the formation of reactive oxygen species and the oxidation of ferrous iron. Mol Cell Biochem, 1994. 137(1): p. 1–8. (Ref. 126).

Srivastava, R., Inhibition of neutrophil response by curcumin. Agents Actions, 1989. 28(3–4): p. 298–303. (Ref 127).

Subramanian, M., et al., Diminution of singlet oxygen–induced DNA damage by curcumin and related antioxidants. Mutat Res, 1994. 311(2): p. 249–255. (Ref. 128).

Donatus, I.A., Sardjoko, and N.P. Vermeulen, Cytotoxic and cytoprotective activities of curcumin. Effects on paracetamol–induced cytotoxicity, lipid peroxidation and glutathione depletion in rat hepatocytes. Biochem Pharmacol, 1990. 39(12): p. 1869–75. (Ref. 129).

Sharma, S.C., et al., Lipid peroxide formation in experimental inflammation. Biochem Pharmacol, 1972. 21(8): p. 1210–1214. (Ref. 130).

Soudamini, K.K., et al., Inhibition of lipid peroxidation and cholesterol levels in mice by curcumin. Indian J Physiol Pharmacol, 1992. 36(4): p. 239–243. (Ref. 132).

Rao, S. and N.N.A. Rao, Curcumin inhibits iron–dependent lipid peroxidation. Int J Pharmaceut, 1993. 100: p. 93–97. (Ref. 133).

Rao, S. and M.N.A. Rao, Curcuminoids as potent inhibitors of lipid peroxidation. J Pharm Pharmacol, 1994. 46: p. 1013–1016. (Ref. 134).

Reddy, A.C. and B.R. Lokesh, Studies on spice principles as antioxidants in the inhibition of lipid peroxidation of rat liver microsomes. Mol Cell Biochem, 1992. 111(1–2): p. 117–124. (Ref. 135).

Reddy, A.C. and B.R. Lokesh, Alterations in lipid peroxides in rat liver by dietary n–3 fatty acids: Modulation of antioxidant enzymes by curcumin, eugenol, and vitamin E, J Nutr Biochem, 1994. 5: p. 181–188. (Ref. 136).

Rajakumar, D.V. and M.N. Rao, Antioxidant properties of dehydrozingerone an curcumin in rat brain homogenates. Mol Cell Biochem, 1994. 140(1): p. 73–79. (Ref. 137).

Unnikrishnan, M.K. and M.N. Rao, Curcumin inhibits nitrogen dioxide induced oxidation of hemoglobin. Mol Cell Biochem, 1995. 146(1): p. 35–37. (Ref. 138).

Chan, M.M., C.T. Ho, and H.I. Huang, Effects of three dietary phytochemicals from tea, rosemary and turmeric on inflammation–induced nitrite production. Cancer Lett, 1995. 96(1): p. 23–29. (Ref. 139).

Joe, B. and B.R. Lokesh, Role of capsaicin, curcumin and dietary n–3 fatty acids in lowering the generation of reactive oxygen species in rat peritoneal macrophages. Biochim Biophys Acta, 1994. 1224(2): p. 255–263.

Reddy, B.S., et al., Inhibitory effect of aspirin on azoxymethane–induced colon carcinogenesis in F344 rats. Carcinogenesis, 1993. 14(8): p. 1493–1497. (Ref. 141).

Rao, C.V., et al., Chemoprevention of colon carcinogenesis by sulindac, a nonsteroidal anti–inflammatory agent. Cancer Res, 1995. 55(7): p. 1464–1472. (Ref. 142).

Boolbol, S.K., et al., Cyclooxgenase–2 overexpression and tumor formation are blocked by sulindac in a murine model of familial adenomatous polyposis. Cancer Res, 1996. 56(11): p. 2556–2560. (Ref. 143).

Cook–Mozaffari, P.J., et al., Oesophageal cancer studies in the Caspian Littoral on Iran: results of a case–control study. Br J Cancer, 1979. 39(3): p. 293–309. (Ref. 211).

Zhang, S., et al., Measurement of retinoids and cartenoids in breast adipose tissue and a comparison of concentrations in breast cancer cases and control subjects. Am J Clin Nutr, 1997. 66(3): p. 626–32. (Ref. 212).

Giovannucci, E., Tomatoes, tomato–based products, lycopene, and cancer: review of the epidomiologic literature. J Natl Cancer Inst, 1999. 91(4): p. 317–331. (Ref. 213).

Erdman, J.W., Jr., T.L. Bierer, and E.T. Gugger, Absorption and transport of carotenoids. Ann N Y Acad Sci, 1993. 691: p. 76–85. (Ref. 214).

Parker, R.S., Absorption, metabolism, and transport of carotenoids. Faseb J, 1996. 10(5): p. 542–551. (Ref. 215).

Bierer, T.L., N.R. Merchen, and J.W. Erdman, Jr., Comparative absorption and transport of five common carotenoids in preruminant calves. J Nutr, 1995. 125(6): p. 1569–1577. (Ref. 216).

Clinton, S.K., Lycopene: chemistry, biology, and implications for human health and disease. Nutr Rev, 1998. 56(2 Pt 1): p. 35–51. (Ref. 217).

Fand, I. and W.P. McNally, Whole–body localization of 14C–tocopheryl acetate in the rat following oral administration. Arch Int Pharmacodyn Ther, 1981. 250(1): p. 4–17. (Ref. 218).

Bendich, A. and L.J. Machlin, Safety of oral intake of vitamin E Am J Clin Nutr, 1988. 48(3): p. 612–619. (Ref. 219).

Traber, M.G., et al., Impaired ability of patients with familial isolated vitamin E deficiency to incorporate alpha–tocopherol into lipoproteins secreted by the liver. J Clin Invest, 1990. 85(2): p. 397–407. (Ref. 221).

Traber, M.G., et al., RRR–and SRR–alpha–tocopherols are secreted without discrimination in human chylomicrons, but RRR–alpha–tocopherol is preferentially secreted in very low density lipoproteins. J Lipid Res, 1990. 31(4): p. 675–685. (Ref 222).

Traber, M.G., et al., Impaired discrimination between stereoisomers of alpha–tocopherol in patients with familial isolated vitamin E deficiency. J Lipid Res, 1993. 34(2): p. 201–210. (Ref. 223).

Traber, M.G., A. Elsner, and R. Brigelius–Flohe, Synthetic as compared with natural vitamin E is preferentially excreted as alpha–CEHC in human urine: studies using deuterated alpha–tocopheryl acetates. FEBS Lett, 1998. 437(1–2): p. 145–148. (Ref. 224).

Helzlsouer, K.J., et al., Summary of the round table discussion on strategies for cancer prevention: diet, food, additives, supplements, and drugs. Cancer Res, 1994. 54(7 Suppl): p. 2044s–2051s. (Ref. 225).

McEvoy, G.K., Vitamin E, in AHFS Drug Information 94. 1994, American Society of Hospital Pharmacists: Bethesda, p. 2415–2417. (Ref. 226).

Vitamin E, in USP DI–vol. III. Approved Drug Products and Legal Requirements, I. United States Pharmacopeia Convention, Editor. 1994, Rand McNally: Taunton, p. 485–486. (Ref. 227).

Kappus, H. and A.T. Diplock, Tolerance and safety of vitamin E: a toxocological position report. Free Radic Biol Med, 1992. 13(1): p. 55–74. (Ref. 228).

Doba, T., G.W. Burton, and K.U. Ingold, Antioxidant and co–antioxidant activity of vitamin C. The effect of vitamin C, either alone or in the presence of vitamin E or a water–soluble vitamin E analogue, upon the peroxidation of aqueous multilamellar phospholipid liposomes. Biochem Biophys Acta, 1985. 835(2): p. 298–303. (Ref. 230).

Stevenson N.R. and M.K. Brush, Existence and characteristics of Na positive–dependent active transport of ascorbic acid in guinea pigs. Am J Clin Nutr, 1969. 22(3): p. 318–26. (Ref. 231).

Kallner, A., D. Hartmann, and D. Horning, On the absorption of ascorbic acid in man. Int J Vitam Nutr Res, 1977. 47(4): p. 383–8. (Ref. 232).

Swanson, C.A., et al., Human [74Se]selenomethionine metabolism: a kinetic model. Am J Clin Nutr, 1991. 54(5): p. 917–26. (Ref. 234).

McGuire, M.K., et al., Selenium status of infants is influenced by supplementation of formula or maternal diets. Am J Clin Nutr, 1993. 58(5): p. 643–8. (Ref. 235).

Deagan, J.T., et al., Effects of dietary selenite, selenocystine and selonomethionine on selenocysteine lyase and glutathione peroxidase activities and on selenium levels in rat tissues. J Nutr, 1987. 117(1): p. 91–8. (Ref. 236).

Franke, K.W., New toxicant occuring natrually in certain samples of plant foodstuffs: results obtained in preliminary feeding trials. J Nutr, 1934. 8: p. 597–603. (Ref. 237).

Ip, C., Differential effect of dietary methionine on the biopotency of selenomethionine and selenite in cancer chemoprevention. J Natl Cancer Inst, 1988. 80(4): p. 258–62. (Ref. 239).

Olsson, B., et al., Pharmacokinetics and bioavailability of reduced and oxidized N–acetylcysteine. Eur J Clin Pharmacol, 1988. 34(1): p. 77–82. (Ref. 240).

Borgstrom, L., B., Kagedal, O. Paulsen, Pharmacokinetics of N–acetylcysteine in man. Eur J Clin Pharmacol, 1986. 31(2): p. 217–22. (Ref. 241).

De Caro, L., et al., Pharmacokinetics and bioavailability of oral acetylcysteine in healthy volunteers. Arzneimittelforschung, 1989. 39(3): p. 382–6. (Ref. 242).

Sjodin, K., et al., Metabolism of N–acetyl–L–cysteine. Some structural requirements for the deacetylation and consequences for the oral bioavailability. Biochem Pharmacol, 1989. 38(22): p. 3981–5. (Ref. 243).

Jones, A.L., et al., Pharmacokinetics of N–acetylcysteine are altered in patients with chronic liver disease. Aliment Pharmacol Ther, 1997. 11(4): p. 787–91. (Ref. 244).

Anonymous, Clinical development plan: curcumin. J Cell Biochem Suppl, 1996. 26: p. 72–85. (Ref. 245).

Shoba, G., et al., Influence of piperine on the pharmacokinetics of curcumin in animals and human volunteers. Planta Med, 1998. 64(4): p. 353–6. (Ref. 246).

Anonymous, Clinical Development Plan: tea extracts green tea polyphenols epigallocetechin gullate. Journal of Cellular Biochemistry, 1996. 26s: p. 236–257. (Ref. 247).

Stahl, W. and H. Sies, Uptake of lycopene and its geometrical isomers is greater from heat–processed than from unprocessed tomato juice in humans. J Nutr, 1992. 122(11): p. 2161–6. (Ref. 249).

Koonsvitsky, B.P., et al., Olestra affects serum concentrations of alpha–tocopherol and carotenoids but not vitamin D or vitamin K status in free–living subjects. J Nutr, 1997. 127(8 Suppl): p. 1636S–1645S. (Ref. 250).

Cooper, D.A., D.R. Webb, and J.C. Peters, Evaluation of the potential for olestra to affect the availability of dietary phytochemicals. J Nutr, 1997. 127(8 Suppl): p. 1699S–1709S. (Ref. 251).

Schlagheck, T.G., et al., Olestra dose response on fat–soluble and water–soluble nutrients in humans. J Nutr, 1997. 127(8 Suppl): p. 1646S–1665S. (Ref. 252).

Kelloff, G.J., et al., Clinical development plan: beta–carotene and other carotenoids. J Cell Biochem Suppl, 1994. 20: p. 110–140. (Ref. 254).

Hill MJ., M.B., and Bussey HJR, Aetiology of adenoma–carcinoma sequence in large bowel. Lancet, 1978. 1: p. 245–7. (Ref. 255).

Potter, J.D., Colorectal cancer: molecules and populations. J Nat Cancer Inst, 1999. 91(11): p. 916–932. (Ref. 256).

World Cancer Research Fund Panel, J. Potte–Chair, Chapter 4.10 Colon, Rectum, in Diet, Nutrition, and the Prevention of Cancer: a Global Perspective. 1997, WCRF/AICR. p. 216–251. (Ref. 258).

Haenszel, W., Cancer Mortality among the foreign born in the United States. J Natl Cancer Inst, 1961. 26: p. 37–132. (Ref. 259).

McMichael, A.J. and G.G. Giles, Cancer in migrants to Australia: extending the descriptive epidemiologica data. Cancer Res, 1988. 48(3): p. 751–6. (Ref. 260).

Nelson, N.J., Is chemoprevention overrated or underfunded. J Natl Cancer Inst, 1996. 88: p. 947–9. (Ref. 261).

Lynch, H.T. and T. Smyrk, Hereditary nonpolyposis colorectal cancer (Lynch syndrome). An updated review. Cancer, 1996. 78(6): p. 1149–67. (Ref. 262).

Winawe, S.J., et al., Colorectal cancer screening: clinical guidelines and rationale. Gastroenterology, 1997. 112(2): p. 594–642. (Ref. 263).

Turesky, R.J., et al., Metabolic activation of carcinogenic heterocyclic aromatic amines by human liver and colon. Carcinogenesis, 1991. 12(10): p. 1839–45. (Ref. 264).

Kadlubar, F.F., et al., Polymorphisms for aromatic amine metabolism in humans: relevance for human carcinogenesis. Environ Health Perspect, 1992. 98: p. 69–74. (Ref. 265).

Freudenheim, J.L., et al., Folate intake and carcinogenesis of the colon and rectum. Int J Epidemiol, 1991. 20(2): p. 368–74. (Ref. 266).

Giovannucci, E., et al., Alcohol, low–methionine—low–folate diets, and risk of colon cancer in men. J Natl Cancer Inst, 1995. 87(4): p. 265–73. (Ref. 267).

Giovannucci, E., et al., Folate; methionine, and alcohol intake and risk of colorectal adenoma. J Natl Cancer Inst, 1993. 85(11): p. 875–84. (Ref. 268).

Slattery, M.L., et al., Are dietary factors involved in DNA methylation associated with colon cancer? Nutr Cancer, 1997. 28(1): p. 52–62. (Ref. 269).

Ulrich, C.M., et al., Colorectal Adenomas and the C677 MTCHR Polymorphism: Evidence for gene–environment interaction? Cancer Epi Biomark Prev, 1999. 8: p. 659–668. (Ref. 270).

Tomeo, C.A., et al., Harvard Report on Cancer Prevention. vol. 3: prevention of colon cancer in the United States. Cancer Causes Control, 1999. 10(3): p. 167–80. (Ref. 271).

International Agency for Research on Cancer World Health Organization and International Association of Cancer Registries. Eds. Parkin, D.M., Whelan, S.L., Ferlay, J., Raymond, L. Young, J. Cancer Incidence in Five Continents vol. VII IARC Sci Publ 143, 1982. (Ref. 272).

World Cancer Research Fund Panel, J. Potter–Chair, Chapter 2 Diet and the cancer process, in Diet, Nutrition, and the Prevention of Cancer: a Global Perspective. 1997, WCRF/AICR, p. 54–71. (Ref. 273).

Potter, J., et al., Colon cancer: a review of the epidemiology. Epidemiol Rev, 1993. 15: p. 499–545. (Ref. 274).

Trock, B., E. Lanza, and P. Greenwald, Dietary fiber, vegetables, and colon cancer: crtical review and meta–analyses of the epidemiologic evidence. J Natl Cancer Inst, 1990. 82(8): p. 650–61. (Ref. 275).

Ma, J., et al., Methylenetetrahydrofolate reductase polymorphism, dietary interactions, and risk of colorectal cancer. Cancer Res, 1997. 57(6): p. 1098–102. (Ref. 276).

Chen, J., et al., A methylenetetrahydrofolate reductase polymorphism and the risk of colorectal cancer. Cancer Res, 1996. 56(21): p. 4862–4. (Ref. 277).

Vane, J.R., R.J. Flower, and R.M. Botting, History of aspirin and its mechanism of action. Stroke, 1990. 21(12 Suppl): p. IV12–23. (Ref. 278).

Wright, F., Historical overview of NSAIDs. Eur J Rheumatol Inflamm, 1993. 13(1): p. 4–6. (Ref. 279).

Lewis, W.H. and M.P.F. Elvin–Lewis, in Medical Botany: Plants Affecting Man's Health. 1977. John Wiley & Sons: New York, p. 150–152. (Ref. 280).

Insel, P., Chapter 27 Analgesic–Antipyretic and Antiinflammatory Agents and Drugs Employed in the Treatment of Gout, in Goodman & Gillman's The Pharmacological Basis of Therapeutics, Ninth Edition, J.G. Hardman, Limbird, L.E., Molinoff, P.B., Ruddon, R.W. and Gillman, A.G., Editor. 1996. McGraw–Hill: New York. p. 617–657. (Ref. 281).

Kune, G.A., S. Kune, and L.F. Watson, Colorectal cancer risk, chronic illnesses, operations, and medications: case control results from the Melbourne Colorectal Cancer Study. Cancer Res, 1988. 48(15): p. 4399–404. (Ref. 282).

Rosenberg, L., et al., A hypothesis: nonsteroidal anti–inflammatory drugs reduce the incidence of large–bowel cancer. J Natl Cancer Inst, 1991. 83(5): p. 355–8. (Ref. 283).

Rosenberg, L., C. Louik, and S. Shapiro, Nonsteroidal antiinflammatory drug use and reduced risk of large bowel carcinoma. Cancer, 1998. 82(12): p. 2326–33. (Ref. 284).

Suh, O., C. Mettlin, and N.J. Petrelli, Aspirin use, cancer, and polyps of the large bowel. Cancer, 1993. 72(4): p. 1171–7. (Ref. 285).

Peleg, II, et al., Aspirin and nonsteroidal anti–inflammatory drug use and the risk of subsequent colorectal cancer. Arch Intern Med, 1994. 154(4): p. 394–9. (Ref. 286).

Muscat, J.E., S.D. Stellman, and E.L. Wynder, Nonsteroidal antiinflammatory drugs and colorectal cancer. Cancer, 1994. 74(7): p. 1847–54. (Ref. 287).

La Vecchia, C., et al., Aspirin and colorectal cancer. Br J Cancer, 1997. 76(5): p. 675–7. (Ref. 288).

Schreinemachers, D.M and R.B. Everson, Aspirin use and lung, colon, and breast cancer incidence in a prospective study. Epidemiology, 1994. 5(2): p. 138–46. (Ref. 289).

Giovannucci, E., et al., Aspirin use and the risk of colorectal cancer and adenoma in male health professionals Ann Intern Med, 1994. 121(4): p. 241–6. (Ref. 290).

Giovannucci, E., et al., Aspirin and the risk of colorectal cancer in women. N Engl J Med, 1995. 333(10): p. 609–14. (Ref. 291).

Paganini–Hill, A., et al., Aspirin use and chronic diseases: a cohort study of the elderly. BMJ, 1989. 299(6710): p. 1247–50. (Ref. 292).

Gann, P.H., et al., Low–dose aspirin and incidence of colorectal tumors in a randomized trial. J Natl Cancer Inst, 1993. 85(15): p. 1220–4. (Ref. 293).

Sturner, T., et al., Aspirin use and colorectal cancer: post–trial follow–up data from the Physicians' Health Study. Ann Intern Med, 1998. 128(9): p. 713–20. (Ref. 294).

Logan, R.F., et al., Effect of aspirin and non–steroidal anti–inflammatory drugs on colorectal adenomas: case–control study of subjects participating in the Nottingham faecal occult blood screening programme. BMJ, 1993. 307(6899): p. 285–9. (Ref. 295).

Greenberg, E.R., et al., Reduced risk of large–bowel adenomas aspirin users. The Polyp Prevention Study Group. J Natl Cancer Inst, 1993. 85(11): p. 912–6. (Ref. 296).

Giardiello, F.M., et al., Treatment of colonic and rectal adenomas with sulindac in familial adenomatous polyposis. N Engl J Med, 1993. 328(18): p. 1313–6. (Ref. 297).

Ruschoff, J., et al., Aspirin suppresses the mutator phenotype associated with hereditary nonpolyposis colorectal cancer by genetic selection. Proc Natl Acad Sci U S A, 1998. 95(19): p. 11301–6. (Ref. 298).

Isomaki, H.A., T. Hakulinen, and U. Joutsenlahti, Excess risk of lymphomas, leukemia and myeloma in patients with rheumatoid arthritis. J Chronic Dis, 1978. 31(11): p. 691–6. (Ref. 299).

Laakso, M., et al., Cancer mortality in patients with rheumatoid arthritis. J Rheumatol, 1986. 13(3): p. 522–6. (Ref. 300).

Gridley, G., et al., Incidence of cancer among patients with rheumatoid arthritis. J Natl Cancer Inst, 1993. 85(4): p. 307–11. (Ref. 301).

Pollard, M. and P.H. Luckert, Indomethacin treatment of rats with dimethylhydrazine–induced intestinal tumors. Cancer Treat Rep, 1980. 64(12): p. 1323–7. (Ref. 302).

Narisawa, T., et al., Inhibition of development of methylnitrosourea–induced rat colon tumors by indomethacin treatment. Cancer Res, 1981. 41(5): p. 1954–7. (Ref. 303).

Pollard, M. and P.H. Luckert, Effect of indomethacin on intestinal tumors induced in rats by the acetate derivative of dimethylnitrosamine. Science, 1981. 214(4520): p. 558–9. (Ref. 304).

Pollard, M., P.H. Luckert, and M.A. Schmidt, The suppressive effect of piroxicam on autochthonous intestinal tumors in the rat. Cancer Lett, 1983. 21(1): p. 57–61. (Ref. 305).

Pollard, M. and P.H. Luckert, Prolonged antitumor effect of indomethacin on autochthonous intestinal tumors in rats. J Natl Cancer Inst, 1983. 70(6): p. 1103–5. (Ref. 306).

Narisawa, T., et al., Inhibition of initiatin and promotion by N–methylnitrosourea–induced colon carcinogenesis in rats by non–steroid anti–inflammatory agent indomethacin. Carcinogenesis, 1983. 4(10): p. 1225–7. (Ref. 307).

Pollard, M. and P.H. Luckert, Effect of piroxicam on primary intestinal tumors induced in rats by N–methylnitrosourea. Cancer Lett, 1984. 25(2): p. 117–21. (Ref. 308).

Reddy, B.S., H. Maruyama, and G. Kelloff, Dose–related inhibition of colon carcinogenesis by dietary piroxicam. a nonsteroidal antiinflammatory drug, during different stages of rat colon tumor development. Cancer Res, 1987. 47(20): p. 5340–6. (Ref. 309).

Moorghen, M., et al., A protective effect of sulindac against chemically–induced primary colonic tumours in mice. J Pathol, 1988. 156(4): p. 341–7. (Ref. 310).

Muto, T., Bussey, H.J.R., and Morson, B.C. The evolution of cancer of the colon and rectum. Cancer, 1975. 36: p. 2251–2270. (Ref. 311).

Kawamori, T., et al., Chemopreventive activity of celecoxib, a specific cyclooxygenase–2 inhibitor, against colon carcinogenesis. Cancer Res, 1998. 58(3): p. 409–12. (Ref. 312).

IARC, General Remarks, in Non–Steroidal Anti–Inflammatory Drugs, I.A.R.C., Editor. 1997, International Agency for Cance Research: Lyon, France. p. 15–39. (Ref. 313).

Loll, P.J., D., Picot, and R.M. Garavito, The structural basis of aspirin activity inferred from the crystal structure of inactivated prostaglandin H2 synthase H2 synthase. Nat Struct Biol, 1995. 2(8): p. 637–43. (Ref. 314).

Picot, D., P.J. Loll, and R.M. Garavito, The x–ray crystal structure of the membrane protein prostaglandin H2 synthase–1. Nature, 1994. 367(6460): p. 243–9. (Ref. 315).

Loll, P.J., et al., Synthesis and use of iodinated nonsteroidal antiinflammatory drugs analogs as crystallographic probes of the prostaglandin H2 synthase cyclooxygenase active site. Biochemistry, 1996. 35(23): p. 7330–40. (Ref. 316).

Marnett, L.J., Aspirin and the potential role of prostaglandins in colon cancer. Cancer Res, 1992. 52(20): p. 5575–89. (Ref. 317).

Kalgutkar, A.S., et al., Aspirin–like molecules that covalently inactivate cyclooxygenase–2. Science, 1998. 280(5367): p. 1268–70. (Ref. 318).

Barnes, C.J., et al., Non–steroidal anti–inflammatory drug effect on crypt cell proliferation and apoptosis during initiation of rat colon carcinogenesis. Br J Cancer, 1998. 77(4): p. 573–80. (Ref. 319).

Tsujii, M., et al., Cyclooxygenase regulates angiogenesis induced by colon cancer cells. Cell, 1998. 93(5): p. 705–16. (Ref. 320).

Ciolino, H.P., et al., Effect of curcumin on the aryl hydrocarbon receptor and cytochrome P450 1A1 in MCF–7 human breast carcinoma cells. Biochem Pharmacol, 1998. 56(2): p. 197–206. (Ref. 322).

Zhang, F., et al., Curcumin inhibits cyclooxygenase–2 transcription in bile acid–and phorbol ester–treated human gastrointestinal epithelial cells. Carcinogenesis, 1999. 20(3): p. 445–51. (Ref. 323).

Deodhar, S.D., R. Sethi, and R.C. Srimal, Preliminary study on antirheumatic activity of curcumin (diferuloyl methane). Indian J Med Res, 1980. 71: p. 632–4. (Ref. 324).

Srimal, R.C., Curcumin. Drugs Future, 1987. 12: p. 331–333. (Ref. 325).

Potter, J.D., Risk factors for colon neoplasia–epidemiology and biology. Eur J Cancer, 1995. 31A(7–8): p. 1033–8. (Ref. 326).

Wu, A.H., Paganini–Hill A., Ross, R.K., and Henderson, B.E., Alcohol, physical activity, and other risk factors for colorectal cancer: A prospective study. Br J Cancer, 1987. 55: p. 687–694. (Ref. 327).

Willett, W.C., et al., Relation of meat, fat, and fiber intake to the risk of colon cancer in a prospective study among women. N Engl J Med, 1990. 323(24): p. 1664–72. (Ref. 328).

Stemmermann, G.N., A. Nomura, and P.H. Chyou, The influence of dairy and nondairy calcium on subsite large––bowel cancer risk. Dis Colon Rectum, 1990. 33(3): p. 190–4. (Ref. 329).

Kampman, E., et al., Fermented dairy products, calcium, and colorectal cancer in The Netherlands Cohort Study. Cancer Res, 1994. 54(12): p. 3186–90. (Ref. 330).

Kearney, J., et al., Calcium, vitamin D, and dairy foods and the occurence of colon cancer in men. Am J Epidemiol. 1996. 143(9): p. 907–17. (Ref. 331).

Heilbrun, L.K., et al., Colon cancer and dietary fat, phosphorus, and calcium in Hawaiian–Japanese men. Am J Clin Nutr, 1986. 43(2): p. 306–9. (Ref. 332).

Garland, C., et al., Dietary vitamin D and calcium and risk of colorectal cancer: a 19–year prospective study in men. Lancet, 1985. 1(8424): p. 307–9. (Ref. 333).

Bostick, R.M., et al., Calcium and colorectal epithelial cell proliferation: a preliminary randomized, double–blinded, placebo–controlled clinical trial. J Natl Cancer Inst, 1993. 85(2): p. 132–41. (Ref. 334).

Zaridze, D., Filipchenko, V., Kustov, V., et al., Diet and colorectal cancer: results of two case–control studies in Russia. Eur J Cancer, 1993. 29A: p. 112–115. (Ref. 335).

Arbman, G., et al., Cereal fiber, calcium, and colorectal cancer. Cancer, 1992. 69(8): p. 2042–8. (Ref. 336).

Benito, E., et al., A population–based case–control study of colorectal cancer in Majorca. I. Dietary factors. Int J Cancer, 1990. 45(1): p. 69–76. (Ref. 337).

Graham, S., et al., Dietary epidemiology of cancer of the colon in western New York. Am J Epidemiol, 1988. 128(3): p. 490–503. (Ref. 338).

Freudenheim, J.L., et al., A case–control study of diet and rectal cancer in western New York. Am J Epidemiol, 1990. 131(4): p. 612–24. (Ref. 339).

Kune, G.A. and S. Kune, The nutritional causes of colorectal cancer: an introduction to the Melbourne study. Nutr Cancer, 1987. 9(1): p. 1–4. (Ref. 340).

Macquart–Moulin, G., et al., Case–control study on colorectal cancer and diet in Marseilles. Int J Cancer, 1986. 38(2): p. 183–91. (Ref. 341).

Slattery, M.L., A.W. Sorenson, and M.H. Ford, Dietary calcium intake as a mitigating factor in colon cancer. Am J Epidemiol, 1988. 128(3): p. 504–14. (Ref. 342).

Lee, H.P., et al., Colorectal cancer and diet in an Asian population—a case–control study among Singapore Chinese. Int J Cancer, 1989. 43(6): p. 1007–16. (Ref. 343).

Whittemore, A.S., et al., Diet, physical activity, and colorectal cancer among Chinese in North America and China. J Natl Cancer Inst, 1990. 82(11): p. 915–26. (Ref. 344).

Peters, R.K., et al., Diet and colon cancer in Los Angeles County, California. Cancer Causes Control, 1992. 3(5): p. 457–73. (Ref. 345).

Meyer, F. and E. White, Alcohol and nutrients in relation to colon cance in middle–aged adults. Am J Epidemiol, 1993. 138(4): p. 225–36. (Ref. 346).

Tuyns, A.J., M. Haelterman, and R. Kaaks, Colorectal cancer and the intake of nutrients: oligosaccharides are a risk factor, fats are not. A case–control study in Belgium. Nutr Cancer, 1987. 10(4): p. 181–96. (Ref. 347).

Negri, E., et al., Calcium, dairy products, and colorectal cancer, Nutr Cancer, 1990. 13(4): p. 255–62. (Ref. 348).

Bergsma–Kadijk, J.A., et al., Calcium does not protect against colorectal neoplasia. Epidemiology, 1996. 7(6): p. 590–7. (Ref. 349).

Baron, J.A., et al., Calcium supplements for the prevention of colorectal adenomas. Calcium Polyp Prevention Study Group. N Engl J Med, 1999. 340(2): p. 101–7. (Ref. 350).

Lipkin, M. and H. Newmark, Effect of added dietary calcium on colonic epithelia–cell proliferation in subjects at high risk for familial colonic cancer. N Engl J Med, 1985. 313(22): p. 1381–4. (Ref. 351).

Lipkin, M., et al., Colonic epithelial cell proliferation in responders and nonresponders to supplemental dietary calcium. Cancer Res, 1989. 49(1): p. 248–54. (Ref. 352).

Wargovich, M.J., et al., Calcium supplementation decreases rectal epithelial cell proliferation in subjects with sporadic adenoma. Gastroenterology, 1992. 103(1): p. 92–7. (Ref. 353).

Bostick, R.M., et al., Calcium and colorectal epithelial cell proliferation in sporadic adenoma patients: a randomized, double–blinded, placebo–controlled clinical trial. J Natl Cancer Inst, 1995. 87(17): p. 1307–15. (Ref. 354).

Holt, P.R., et al., Modulation of abnormal colonic epithelial cell proliferation and differentiation by low–fat dairy foods: a randomized controlled trial. Jama, 1998. 280(12): p. 1074–9. (Ref. 355).

Pence, B.C. and F. Buddingh, Inhibition of dietary fat–promoted colon carcinogenesis in rats by supplemental calcium or vitamin D3. Carcinogenesis, 1988. 9(1): p. 187–90. (Ref. 356).

Wargovich, M.J., et al., Inhibition of the promotional phase of azomymethane–induced colon carcinogenesis in the F344 rat by calcium lactate: effect of stimulating two human nutrient density levels. Cancer Lett, 1990. 53(1): p. 17–25. (Ref. 357).

Lipkin, M. and H. Newmark, Calcium and the prevention of colon cancer. J Cell Biochem Suppl, 1995. 22: p. 65–73. (Ref. 358).

Buset, M., Lipkin, M., Winawer, S., et al., Inhibition of human colonic epithelial cell proliferation in vivo and in vitro by calcium. Cancer Res, 1987: 46: p. 5426–5430. (Ref. 359).

Arlow, F.L., et al., Attenuation of azoxymethane–induced colonic mucosal ornithine decarboxylase and tyrosine kinase activity by calcium in rats. Cancer Res, 1989. 49(21): p. 5884–8. (Ref. 360).

Wargovich, M.J., et al., Calcium ameliorates the toxic effect of deoxycholic acid on colonic epithelium. Carcinogenesis, 1983. 4(9): p. 1205–7. (Ref. 361).

Vogel, V.G. and R.S. McPherson, Dietary epidemiology of colon cancer. Hematol Oncol Clin North Am, 1989. 3(1): p. 35–63. (Ref. 362).

Garland, C.F. and F.C. Garland, Do sunlight and vitamin D reduce the likelihood for colon cancer? Int J Epidemiol, 1980. 9(3): p. 227–31. (Ref. 364).

Gorham, E.D., C.F. Garland, F.C. Garland, Acid haze air pollution and breast and colon cancer mortality in 20 Canadian cities. Can J Public Health, 1989. 80(2): p. 96–100. (Ref. 365).

Emerson, J.C. and N.S. Weiss, Colorectal cancer and solar radiation. Cancer Causes Control, 1992. 3(1): p. 95–9. (Ref. 366).

Bostick, R.M., et al., Relation of calcium, vitamin D, and dairy food intake to influence of colon cancer among older women. The Iowa Women's Health Study. Am J Epidemiol, 1993. 137(12): p. 1302–17. (Ref. 367).

Martinez, M.E., et al., Calcium, vitamin D, and the occurrence of colorectal cancer among women. J Natl Cancer Inst, 1996. 88(19): p. 1375–82. (Ref. 368).

Zheng, W., et al., A prospective cohort study of intake of calcium, vitamin D, and other micronutrients in relation to incidence of rectal cancer among postmenopausal women. Cancer Epidemiol Biomarkers Prev, 1998. 7(3): p. 221–5. (Ref. 369).

Benito, E., et al., Nutritional factors in colorectal cancer risk: a case–control study in Majorca. Int J Cancer, 1991. 49(2): p. 161–7. (Ref. 370).

Boutron, M.C., et al., Calcium, phosphorus, vitamin D, dairy products and colorectal carcinogenesis: a French case—control study. Br J Cancer, 1996. 74(1): p. 145–51. (Ref. 371).

Pritchard, R.S., J.A. Baron, and M. Gerhardsson de Verdier, Dietary calcium, vitamin D, and the risk of colorectal cancer in Stockholm, Sweden. Cancer Epidemiol Biomarkers Prev, 1996. 5(11): p. 788–93. (Ref. 373).

Marcus, P.M. and P.A. Newcomb, The association of calcium and vitamin D, and colon and rectal cancer in Wisconsin women. Int J Epidemiol, 1998. 27(5): p. 788–93. (Ref. 373).

Garland, C.F., et al., Serum 25–hydroxyvitamin D and colon cancer: eight–year prospective study. Lancet, 1989. 2(8673): p. 1176–8. (Ref. 374).

Tangrea, J., et al., Serum levels of vitamin D metabolites and the subsequent risk of colon and rectal cancer in Finnish men. Cancer Causes Control, 1997. 8(4): p. 615–25. (Ref. 375).

Niv, Y., et al., In colorectal carcinoma patients, serum vitamin D levels vary according to stage of the carcinoma. Cancer, 1999. 86(3): p. 391–7. (Ref. 376).

Ferraroni, M., et al., Selected micronutrient intake and the risk of colorectal cancer, Br J Cancer, 1994. 70(6): p. 1150–5. (Ref. 377).

Neugut, A.J., et al., The effect of calcium and vitamin supplements on the incidence and recurrence of colorectal adenomatous polyps. Cancer, 1996. 78(4): p. 723–8. (Ref. 378).

Shabahang, M., et al., Growth inhibition of HT–29 human colon cancer cells by analogues of 1,25–dihydroxyvitamin D3. Cancer Res, 1994. 54(15): p. 4057–64. (Ref. 379).

Zhao. X. and D. Feldman, Regulation of vitamin D receptor abundance and responsiveness during differentiation of HT–29 human colon cancer cells. Endocrinology, 1993. 132(4): p. 1808–14. (Ref. 380).

Sitrin, M.D., et al., Dietary calcium and vitamin D modulate 1,2–dimethylhydrazine–induced colonic carcinogenesis in the rat. Cancer Res, 1991. 51(20): p. 5608–13. (Ref. 381).

Cross, H.S., et al., Growth control of human colon cancer cells by vitamin D and calcium in vitro. J Natl Cancer Inst, 1992. 84(17): p. 1355–7. (Ref. 382).

DeLuca, H.F. and V. Ostrem, The relationship between the vitamin D system and cancer. Adv Exp Med Biol, 1986, 206: p. 413–29. (Ref. 383).

Wargovich, M.J. and P.H. Lointier, Calcium and vitamin D modulate mouse colon epithelial proliferation and growth characteristics of a human colon tumor cell line. Can J Physiol Pharmacol, 1987. 65(3): p. 472–7. (Ref. 384).

Brenner, R.V., et al., The antiproliferative effect of vitamin D analogs on MCF–7 human breast cancer cells. Cancer Lett, 1995. 92(1): p. 77–82. (Ref. 385).

Frampton, R.J., et al., Presence of 1,25–hydroxyvitamin D3 receptors in established human cancer cell lines in culture. Cancer Res, 1982. 42(3): p. 1116–9. (Ref. 386).

Thomas, M.G., et al., Vitamin D receptor expression in colorectal cancer. J Clin Pathol, 1999. 52(3): p. 181–3. (Ref. 387).

Belleli, A., et al., A protective role of 1,25–dihydroxyvitamin D3 in chemically induced rat colon carcinogenesis. Carcinogenesis, 1992. 13(12): p. 2293–8. (Ref. 388).

Lointier, P., et al., The role of vitamin D3 in the proliferatin of a human colon cancer cell line in vitro. Anticancer Res, 1987. 7(4B): p. 817–21. (Ref. 389).

Cross, H.S., C. Huber, and M. Peterlik, Antiproliferative effect of 1,25–dihydroxyvitamin D3 and its analogs on human colon adenocarcinoma cells (CaCo–2): influence of extracellular calcium. Biochem Biophys Res Commun, 1991. 179(1): p. 57–62. (Ref. 390).

Colston, K.W., et al., Effects of synthetic vitamin D analogues of 1 alpha,25–dihydroxyvitamin D3: differential effects of leukemic cell growth, differentiation, and intestinal calcium absorption. Cancer Res, 1990. 50(21): p. 6857–64. (Ref. 392).

Reitsma, P.H., et al., Regulation of myc gene expression in HL–60 leukemia cells by a vitamin D metabolite. Nature, 1983. 306(5942): p. 492–4. (Ref. 393).

Koizumi, T., et al., Suppression of c–myc mRNA expression by steroid hormones in HTLV–1–infected T–cell line, KH–2. Int J Cancer, 1989. 44(4): p. 701–6. (Ref. 394).

Brelvi, Z.S. and G.P. Studzinski, Inhibition of DNA synthesis by an inducer of differentiation of leukemic cells, I alpha, 25 dihydroxy vitamin D3, precedes down regulation of the c–myc gene. J Cell Physiol, 1986. 128(2): p. 171–9. (Ref. 395).

Karmali, R., et al., 1,25(OH)2D3 regulates c–myc mRNA levels in tonsillar T lymphocytes. Immunology, 1991. 74)4): p. 589–93. (Ref. 396).

Tu–Yu, A.H., R.C. Morris, and H.E. Ives, Differential modulation of fos and jun gene expression by 1,25–dihydroxyvitamin D3. Biochem Biophys Res Commun, 1993. 193(1): p. 161–6. (Ref. 397).

Wiseman, H., Vitamin D is a membrane antioxidant. Ability to inhibit iron–dependent lipid peroxidation in liposomes compared to cholesterol, ergosterol and tamoxifen and relevance to anticancer action. FEBS Lett, 1993. 326(1–3): p. 285–8. (Ref. 398).

Oikawa, T., et al., Inhibition of angiongenesis by vitamin D3 analogues. Eur J Pharmacol, 1990. 178(2): p. 247–50. (Ref. 399).

Colston, K. W., U. Berger, and R.C. Coombes, Possible role for vitamin D in controlling breast cancer cell proliferation. Lancet, 1989. 1(8631): p. 188–91. (Ref. 400).

DeLuca, H.F., New concepts of vitamin D functions. Ann N Y Acad Sci, 1992. 669: p. 59–68; discussion 68–9. (Ref. 401).

Abe, E., Miyaura, C., Sakagami, H., Takeda, M., et al., Differential of mouse myeloid leukemia cells induced by 1–alpha,25–hydroxyvitamin D3. Proc. Natl. Acad. Sci. USA, 1981. 78: p. 4990–4994. (Ref. 402).

Petkovich, P.M., et al., 1,25–Dihydroxyvitamin D3 increases epidermal growth factor receptors and transforming growth factor beta–like activity in a bone–derived cell line. J Biol Chem, 1987. 262(28): p. 13424–8. (Ref. 403).

Naveilhan, P., et al., Induction of glioma cell death by 1,25(OH)2 vitamin D3: towards an endocrine therapy of brain tumors? J Neurosci Res, 1994. 37(2): p. 271–7. (Ref. 404).

James, S.J., A.G. Basnakian, and B.J. Miller, In vitro folate deficiency induces deoxynucleotide pool imbalance, apoptosis, and mutagenesis in Chinese hamster ovary cells. Cancer Res, 1994. 54(19): p. 5075–80. (Ref. 405).

Blount, B.C. and B.N. Ames, DNA damage in folate deficiency. Baillieres Clin Haematol, 1995. 8: p. 461–478. (Ref. 406).

Jennings, E., Folid acid as a cancer–preventing agent. Med. Hypotheses, 1995. 45: p. 297–303. (Ref. 407).

Pogribny, I.P., et al., Breaks in genomic DNA and within the p53 gene are associated with hypomethylation in livers of folate/methyl–deficient. Cancer Res, 1995. 55(9): p. 1894–901. (Ref. 408).

Wainfan, E. and L.A. Poirier, Methyl groups in carcinogenesis: effects on DNA methylation and gene expression. Cancer Res, 1992. 52(7 Suppl): p. 2071s–2077s. (Ref. 409).

Ahuja, N., et al., Association between CpG island methylation and microsatellite instability in colorectal cancer. Cancer Res, 1997. 57(16): p. 3370–4. (Ref. 410).

Lengauer, C., K.W. Kinzler, B. Vogelstein, Genetic instability in colorectal cancers. Nature, 1997. 386(6625): p. 623–7. (Ref. 411).

Lengauer, C., K.W. Kinzler, and B. Vogelstein, DNA methylation and genetic instability in colorectal cancer cells. Proc Natl Acad Sci U S A, 1997. 94(6): p. 2545–50. (Ref. 412).

Gama–Sosa, M.S., Slagel, V.A., Trewyn, R.W., et al., The 5–methylcytosine content of DNA from human tumors. Nucleic Acids Res., 1990. 11: p. 6883–6894. (Ref. 413).

Laird, P.W. and R. Jaenisch, DNA methylation and cancer. Hum Mol Genet, 1994. 3(Spec No): p. 1487–95. (Ref. 414).

Vogelstein, B., et al., Genetic alterations during colorectal–tumor development. N Engl J Med, 1988. 319(9): p. 525–32. (Ref. 415).

Kim, Y.I., et al., Global DNA hypomethylation increases progressively in cervical dysplasia and carcinoma. Cancer, 1994. 74(3): p. 893–9. (Ref. 416).

Cooper, A.J., Biochemistry of sulfur–containing amino acids. Annu Rev Biochem, 1983. 52: p. 187–222. (Ref. 417).

Giovannucci, E., et al., Multivitamin use, folate, and colon cancer in women in the Nurses' Health Study. Ann Intern Med, 1998. 129(7): p. 517–24. (Ref. 418).

Baron, J.A., et al., Folate intake, alcohol consumption, cigarette smoking, and risk of colorectal adenomas. J Natl Cancer Inst, 1998. 90(1): p. 57–62. (Ref. 419).

Lashner, B.A., et al., Effect of folate supplementation on the incidence of dysplasia and cancer in chronic ulcerative colitis. A case–control study. Gastroenterology, 1989. 97(2): p. 255–9. (Ref. 420).

Benito, E., et al., Diet and colorectal adenomas: a case–control study in Majorca. Int J Cancer, 1993. 55(2): p. 213–9. (Ref. 421).

Bird, C.L., et al., Red cell and plasma folate, consumption, and the risk of colorectal adenomatous polyps. Cancer Epidemiol Biomarkers Prev, 1995. 4(7): p. 709–14. (Ref. 422).

Paspatis, G.A., et al., Folate status and adenomatous colonic polyps: A colonoscopically controlled study. Dis Colon Rectum, 1995. 38(1): p. 64–7; discussion 67–8. (Ref. 423).

Glynn, S.A., et al., Colorectal cancer and folate status: a nested case–control study among male smoker. Cancer Epidemiol Biomarkers Prev, 1996. 5(7): p. 487–94. (Ref. 424).

Tseng, M., et al., Micronutrients and the risk of colorectal adenomas. Am J Epidemiol, 1996. 144(11): p. 1005–14. (Ref. 425).

White, E., J.S. Shannon, and R.E. Patterson, Relationship between vitamin and calcium supplement use and colon cancer. Cancer Epidemiol Biomarkers Prev, 1997. 6(10): p. 769–74. (Ref. 426).

Kato, I., et al., Serum folate, homocysteine and colorectal cancer risk in women: a nested case–control study. Br J Cancer, 1999. 79(11–12): p. 1971–22. (Ref. 427).

Ma, J., et al., A polymorphism of the methionine synthase gene: association with plasma folate, vitamin B12, homocyst(e)ine, and colorectal cancer risk. Cancer Epidemiol Biomarkers Prev, 1999. 8(9): p. 825–9. (Ref. 428).

Slattery, M.L., et al., Methylenetetrahydrofolate reductase, diet, and risk of colon cancer. Cancer Epidemiol Biomarkers Prev, 1999. 8(6): p. 513–8. (Ref. 429).

Hillman, R.S., Chapter 53 Hematopoetic Agents: Growth Factors, Minerals and Vitamins, in Goodman & Gillman's The Pharmacological Basis of Therapeutics, Ninth Edition, J.G. Hardman, Limbird, L.E., Molinoff, P.B., Ruddon, R.W. and Gillman, A.G., Editor. 1996. McGraw–Hill: New York. p. 1311–1340. (Ref. 430).

Marcus, R.a.C., A.M., Chapter 62 Water–Soluble Vitamins, in Goodman & Gillman's The Pharmacological Basis of Therapeutics, Ninth Edition, J.G. Hardman, Limbird, L.E., Molinoff, P.B., Ruddon, R.W. and Gillman, A.G., Editor. 1996. McGraw–Hill: New York, p. 1555–1572. (Ref. 431).

National Cancer Institutes. DCPC, Clinical Development Plan: Folic Acid. J. Cell. Biochemistry, 1996. 26S: p. 100–113. (Ref. 432).

World Cancer Research Fund Panel, J. Potter–Chair, Diet, Nutrition, and the prevention of cancer: a global perspective, 1997, Washington D.C.: WCRF/AICR. (Ref. 433).

Hercberg, S., et al., The potential role of antioxidant vitamins in preventing cardiovascular diseases and cancers. Nutrition, 1998. 14(6): p. 513–20. (Ref. 434).

Slattery, M.L., et al., Diet diversity, diet composition, and risk of colon cancer (United States). Cancer Causes Control, 1997. 8(6): p. 872–82. (Ref. 435).

Slattery, M.L., et al., Eating patterns and risk of colon cancer. Am J Epidemiol, 1998. 148(1): p. 4–16. (Ref. 436).

Uchida, S., et al., Active oxygen free radicals are scavenged by condensed tannins. Prog Clin Biol Res, 1988. 280: p. 135–8. (Ref. 167).

Uchida, S., et al., Radioprotective effects of (–)–epigallocatechin 3–O–gallate (green–tea tannin) in mice. Life Sci, 1992. 50(2): p. 147–52. (Ref. 168).

Nanjo, F., et al., Effects of dietary tea catechins on alpha–tocopherol levels, lipid peroxidation, and erythrocyte deformability in rats fed on high palm oil and perilla oil diets. Biol Pharm Bull, 1993. 16(11): p. 1156–9. (Ref. 169).

Katiyar, S.K., R. Agarwal, and H. Mukhtar, Inhibtionof spontaneous and photo–enhanced lipid peroxidation in mouse epidermal microsomes by epicatechin derivatives from green tea. Cancer Lett, 1994. 79(1): p. 61–6. (Ref. 170).

Yen, G.–C. and H.–Y. Chen, Antioxidant activity of various tea extracts in relation to their antimutagenicity. J Agric Food Chem, 1995. 43: p. 27–32. (Ref. 171).

Klaunig, J.E., Chemopreventive effects of green tea components on hepatic carcinogenesis. Prev Med, 1992. 21(4): p. 510–9. (Ref. 172).

Sigler, G., C. Han, and J. Chen, Inhibition of oncogene expression by green tea and (–)–epigallocatechin gallate in mice. Nutr Cancer, 1995. 24(2): p. 203–9. (Ref. 174).

Lea, M.A., et al., Inhibitory effects of tea extracts and (–)–epigallocatechin gallate on DNA synthesis and proliferation of hepatoma and erythroleukemia cells. Cancer Lett, 1993. 68(2–3): p. 231–6. (Ref.175).

Stich, H.F., Teas and tea components as inhibitors of carcinogen formation in model systems and man. Prev Med, 1992. 21(3): p. 377–84. (Ref. 176).

Xu, G.P., P.J. Song, and P.I. Reed, Effects of fruit juices, processed vegetable juice, orange peel and green tea on endogenous formation of N–nitrosoproline in subjects from a high–risk area for gastric cancer in Moping County, China. Eur J Cancer Prev, 1993. 2(4): p. 327–35. (Ref. 177).

Demmig–Adams, B., A.M. Gilmore, and W.W.d. Adams, Carotenoids 3: in vivo function of carotenoids in higher plants. Faseb J, 1996. 10(4): p. 403–12. (Ref. 178).

Stahl, W. and H. Sies, Lycopene: a biologically important carotenoid for humans? Arch Biochem Biophys, 1996. 336(1): p. 1–9. (Ref. 179).

Gerster, H., The potential role of lycopene for human health. J Am Coll Nutr, 1997. 16(2): p 109–26. (Ref. 180).

Peto, R., et al., Can dietary beta–carotene materially reduce human cancer rates? Nature, 1981. 290(5803): p. 201–8. (Ref. 181).

Ziegler, R.G., A review of epidemiologic evidence that carotenoids reduce the risk of cancer. J Nutr, 1989. 119(1): p. 116–22. (Ref. 182).

Britton, G., Structure and properties of carotenoids in relation to function. Faseb J, 1995. 9(15): p. 1551–8. (Ref. 183).

Olson, J.A. and N.I. Krinsky, Introduction: the colorful, fascinating world of the carotenoids: important physiologic modulators. Faseb J, 1995. 9(15): p. 1547–50. (Ref. 184).

Halevy, O. and D. Sklan, Inhibition of arachidonic acid oxidation by beta–carotene, retinol and alpha–tocopherol. Biochim Biophys Acta, 1987. 918(3): p. 304–7. (Ref. 185).

Burton, G.W., and K.U. Ingold, beta–Carotene: an unusual type of lipid antioxidant. Science, 1984. 224(4649): p. 569–73. (Ref. 186).

Di Mascio, P., S. Kaiser, and H. Sies, Lycopene as the most efficient biological carotenoid singlet oxygen quencher. Arch Biochem Biophys, 1989. 274(2): p. 532–8. (Ref. 187).

Chopra, M., R.L. Willson, and D.I. Thurnham, Free radical scavenging of lutein in vitro. Ann N Y Acad Sci, 1993. 691: p. 246–9. (Ref. 188).

Bors, W., M. Saran, and C. Michel, Radical intermediates involved in the bleaching of the carotenoid crocin. Hydroxyl radicals, superoxide anions and hydrated electrons. Int J Radiat Biol Relat Stud Phys Chem Med, 1982. 41(5); p. 493–501. (Ref. 189).

Rousseau, E.J., A.J. Davison, and B. Dunn, Protection by beta–carotene and related compounds against oxygen–mediated cytotoxicity and genotoxicity: implications for carcinogenesis and anticarcinogenesis. Free Radic Biol Med, 1992. 13(4): p. 407–33. (Ref. 190).

191. Bohm, F., et al., Cellular bound beta–carotene quenches singlet oxygen in man. J Photochem Photobiol B, 1993. 21(2–3): p. 219–21. (Ref. 191).

Khachik, F., et al., Identification, quantification, and relative concentrations of carotenoids and their metabolites in human milk and serum. Anal Chem, 1997. 69(10): p. 1873–81. (Ref. 192).

Shah, G.M., U.C. Goswami, and R.K. Bhattacharya, Action of some retinol derivatives and their provitamins on microsome–catalyzed formation of benzo[a]pyrene–DNA adduct. J Biochem Toxicol, 1992. 7(3): p. 177–81. (Ref. 193).

Hathcock, J.N., et al., Evaluation of vitamin A toxicity. Am J Clin Nutr, 1990. 52(2): p. 183–202. (Ref. 194).

Jyonouchi, H., et al., Beta–carotene and canthaxanthin inhibit chemically–and physically–induced neoplastic transformation in 10T1/2 cells. Carcinogenesis, 1988. 9(9): p. 1533–9. (Ref. 196).

Hazuka, M.B., et al., Beta–carotene induces morphological differentiation and decreases adenylate cyclase activity in melanoma cells in culture. J Am Coll Nutr, 1990. 9(2): p. 143–9. (Ref. 197).

Betram, J.S., et al., Diverse carotenoids protect against chemically induced neoplastic transformation. Carcinogenesis, 1991. 12(4): p. 671–8. (Ref. 198).

Zhang, L.X., R.V. Cooney, and J.S. Bertram, Carotenoids enhance gap junctional communication and inhibit lipid peroxidation in C3H/10T1/2 cells: relationship to their cancer chemopreventive action. Carcinogenesis, 1991. 12(11): p. 2109–14. (Ref. 199).

Kvale, G., E. Bjelke, and J.J. Gart, Dietary habits and lung cancer risk. Int J Cancer, 1983. 31(4): p. 397–405. (Ref. 200).

Forman, M.R., et al., The effect of dietary intake of fruits and vegetables on the odds ration of lung cancer among Yunnan tin miners. Int J Epidemiol, 1992. 21(3): p. 437–41. (Ref. 201).

Agudo, A., et al., Vegetable and fruit intake and the risk of lung cancer in women in Barcelona, Spain. Eur J Cancer, 1997. 33(8): p. 1256–61. (Ref. 202).

Modan, B., H. Cuckle, and F. Lubin, A note on the role of dietary retinol and carotene in human gastro–intestinal cancer. Int J Cancer, 1981. 28(4): p. 421–4. (Ref. 203).

Buiatti, E., et al., A case–control study of gastric cancer and diet in Italy. Int J Cancer, 1989. 44(4): p. 611–6. (Ref. 204).

Hansson, L.E., et al., Diet and risk of gastric cancer. A population–based case–control study in Sweden. Int J Cancer, 1993. 55(2): p. 181–9. (Ref. 205).

Franceschi, S., et al., Tomatoes and risk of digestive–tract cancers. Int J Cancer, 1994. 59(2): p. 181–4. (Ref. 206).

Hu, J.F., et al., Diet and cancer of the colon and rectum: a case–control study in China. Int J Epidemiol, 1991. 20(2): p. 362–7. (Ref. 207).

Burney, P.G., G.W. Comstock, and J.S. Morris, Serologic precursors of cancer: serum micronutrients and the subsequent risk of pancreatic cancer. Am J Clin Nutr, 1989. 49(5): p. 895–900. (Ref. 208).

Mills, P.K., et al., Cohort study of diet, lifestyle, and prostate cancer in Adventist men. Cancer, 1989. 64(3): p. 598–604. (Ref. 209).

Giovannucci, E., et al., Intake of carotenoids and retinol in relation to risk of prostate cancer. J Natl Cancer Inst, 1995. 87(23): p. 1767–76. (Ref. 210).

* cited by examiner

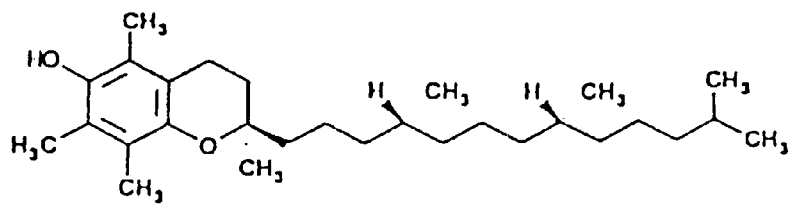
Figure 1. Structure of d-α-tocopherol.
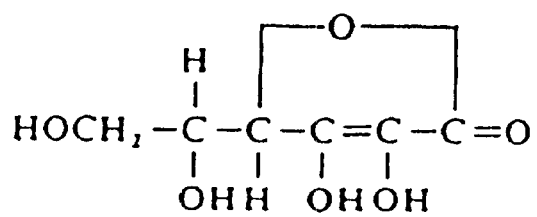
Figure 2. Structure of ascorbic acid.
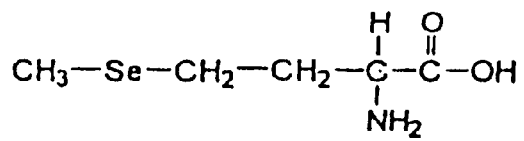
Figure 3. Structure of l-selenomethionine.

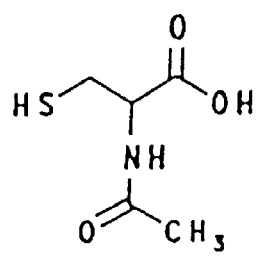
Figure 4. Structure of N-acetyl-l-cysteine.
Figure 5. Structure of curcumin.
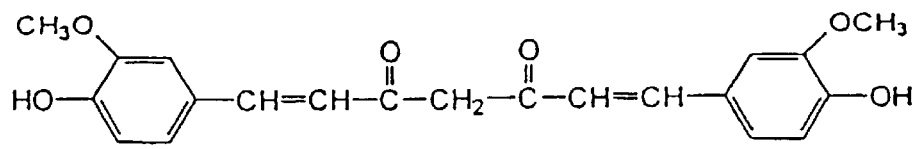
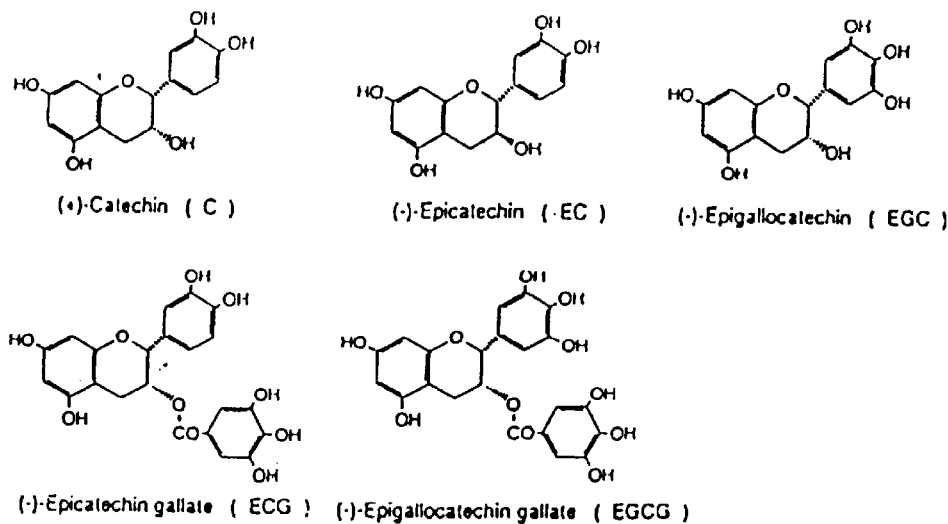
Figure 6. Structures of important polyphenols in green tea [27].

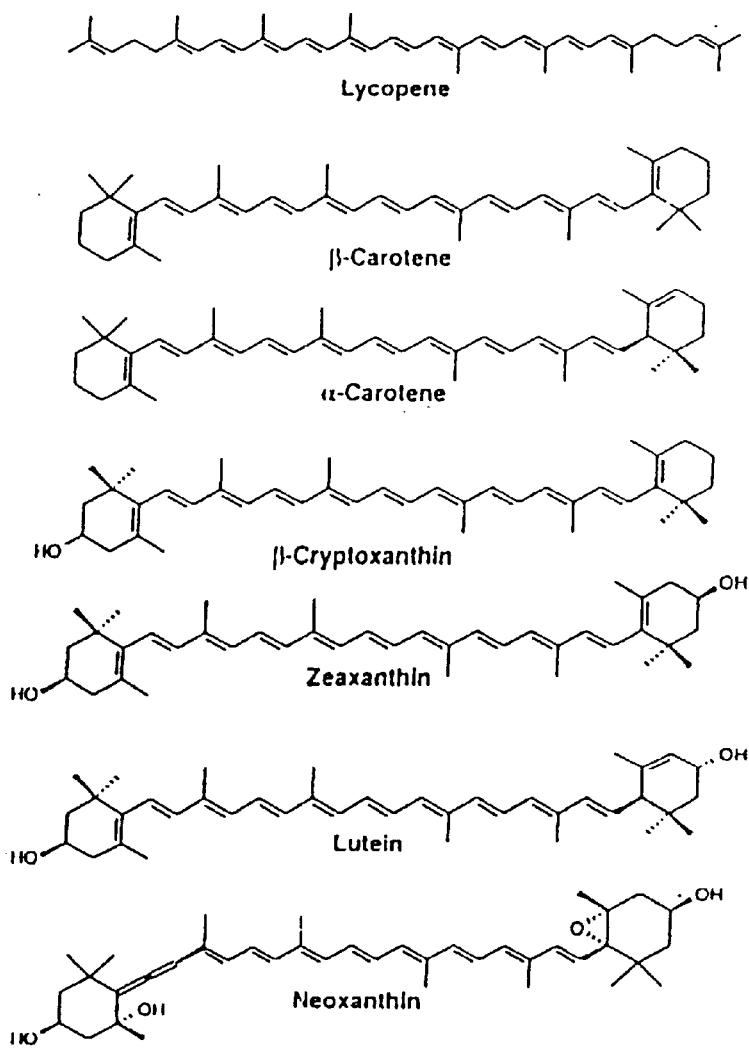
Figure 7. Structures of important carotenoids [29].
Figure 8. Structure of salicin.
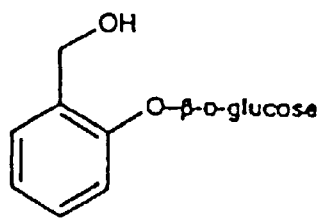

Figure 9. Structure of ergocalciferol.
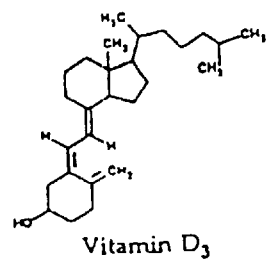
Figure 10. Structure of folic acid.
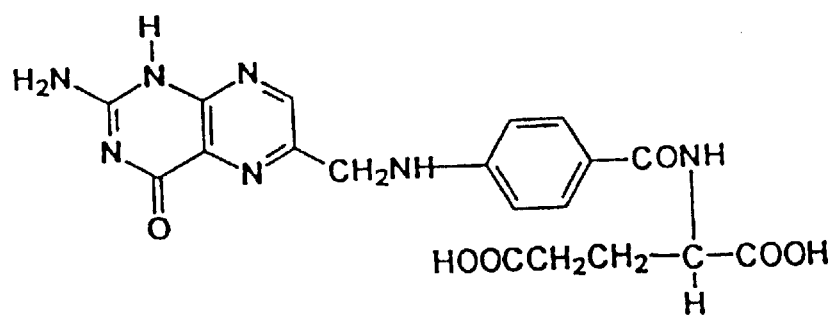

Figure 11. Structures of vitamin $B_6$.
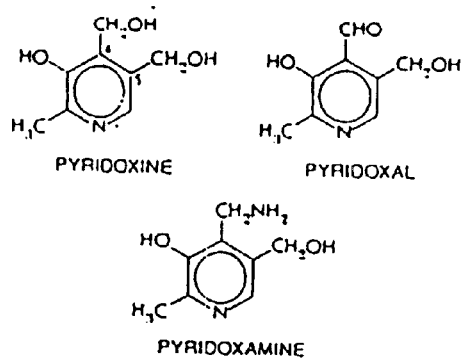
Figure 12. Structure of vitamin $B_{12}$.
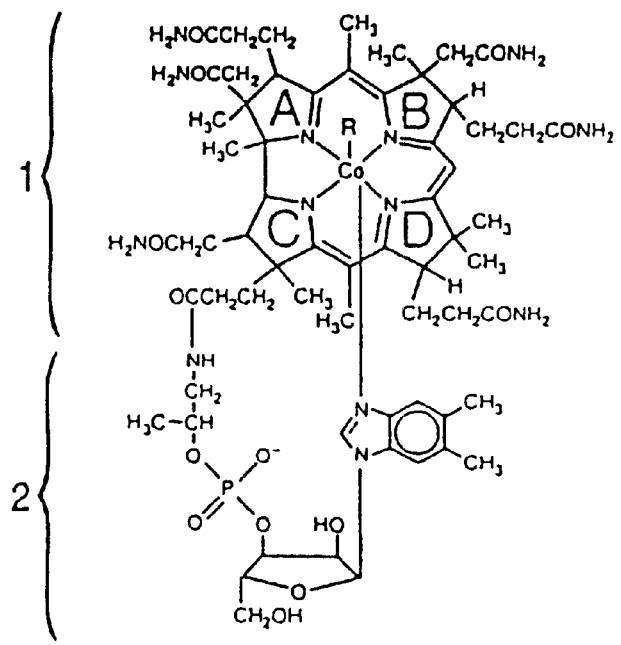

NUTRIENT FORMULATIONS FOR DISEASE REDUCTION

RELATED APPLICATIONS

This application claims the benefit of priority, under U.S. and international law, of U.S. Provisional Application No. 60/139,347, filed Jun. 15, 1999. The entire contents of that provisional application is incorporated herein by reference.

BACKGROUND OF THE INVENTION

Human studies demonstrate that cancer is largely a preventable disease and that 35–40% of cancer incidence and mortality worldwide can be substantially reduced by changes in the human diet. Specifically, there is compelling worldwide evidence of an association between fruit and vegetable consumption and cancer risk reduction. Other human and animal diseases, as well, are influenced by diet and can be substantially reduced by changes in diet. Examples include diabetes (especially type II diabetes), cardiovascular diseases, Alzheimers disease, osteoporosis, and many others. Likewise, other physical conditions that involve bodily attributes or performance issues, other than diseases, may be affected by diet. The present invention relates to nutrient formulations useful in reducing (including preventing, delaying, inhibiting and/or treating) cancers and other human and animal (especially mammalian) diseases and physical conditions, methods of using such formulations, and methods of identifying such formulations and the components (particularly nutrient ingredients) to be included in the formulations to achieve optimal disease reduction.

As one disease example, tumor development in cancers (carcinogenesis) proceeds through a series of multiple overlapping stages, including initiation (change in DNA), promotion (proliferation of cells with damaged DNA) and progression (growth of cells with cumulative genetic changes, including changes in key control genes that lead to malignant cells and to the emergence of a clinically detectable cancer). Since cancer development may take from 10–30 years, a preferred cancer risk reduction strategy is to insure optimum cellular and tissue health and to minimize cellular events involved in the tumor development process in healthy individuals (typically including those of ages 20–44 or younger) during the early phases of potential or actual carcinogenesis. In one aspect of the invention, this is achieved by the preferably regular, systematic and long-term administration of one or more formulations having multiple active components that, in combination, provide focused antioxidant protection and oxidative balance in the subject. These antioxidant/oxidative balance formulations of the invention provide a particularly useful approach in reducing the risk of cancer diseases generally. In another aspect of the invention, the nutrient formulation contains nutrient components specifically identified and selected to reduce or interfere with a particular disease or disease etiology (such that of a specific cancer disease, e.g. colorectal cancer as discussed below). The invention provides a method of screening and identifying useful components for such formulations. In still another aspect of the invention, the formulations, and the method of screening their components, are directed to the reduction of multiple individual diseases.

Additional protection against disease is required with age (e.g., 45–65, and over 65 years of age) and customized doses of the nutrient formulations of the invention will typically be recommended for high-risk populations (e.g., smokers, genetic risk, cancer survivors, etc.). In the case of cancer, many of these individuals will already have initiated cells, but both promotion and progression are targets for control according to the invention. Accordingly, the nutrient formulations (and their dosage components) are designed specifically for each of the various age groups and relative risk populations.

A comparison of regional human diets with worldwide patterns of cancer incidence strongly suggests that food and nutrition affect cancer incidence and mortality, and therefore cancer risk. Epidemiologic and ecologic evidence indicates that cancer incidence varies significantly between different regions and populations around the world. The observation that the patterns of cancer are sensitive to human migration and urbanization, and the lack of simple patterns of genetic inheritance for most human cancers, indicate that cancer rates are strongly influenced by environmental factors, especially diet. Individual-level epidemiological studies (particularly cohort and case-control studies) provide specific evidence for the identity of some of the dietary patterns and food that may alter risk. Thus, data support the hypothesis that cancer is largely a preventable disease and that the incidence of cancer can be substantially reduced by modifying dietary intake.

The results of a recent report commissioned by the executive officers of the World Cancer Research Fund and the American Institute for Cancer Research estimated that 30–40% of cancer cases throughout the world are preventable by modifications of diet and nutrition [1]. (The references cited herein by reference numeral are listed in the Appendix to this specification.) There is strong and consistent evidence of an association between fruit and vegetable consumption and cancer risk reduction on a worldwide basis [1–4]. In addition, low fruit and vegetable intake is associated with 1.5 to 2 times greater risk of cancer at many sites compared with high intake. Recent reviews have evaluated the large body of evidence concerning the relationship between fruit and vegetable intake and cancer incidence [5–9]. For all cancer sites, a statistically significant protective effect of fruit and vegetable consumption is found in 128 of the 156 dietary studies [3]. The evidence is strongest for lung cancer [5, 8]. In addition, fruit and vegetable consumption is associated with decreased risk for cancers of the pancreas, breast, stomach, colorectal, bladder, cervix, ovaries and endometrium [3].

Evidence now indicates that several types of cancer develop through the progressive acquisition and accumulation of mutations in multiple genes [10, 11]. Genetic mutations can be initiated via a variety of cellular events that are triggered by environmental factors. For example, genotoxic carcinogens or their metabolites act as mutagens by covalently modifying DNA, resulting in chemical changes in the genetic material. In addition, endogenously formed reactive oxygen species (ROS) and metabolites of nitrogen oxide also contribute to DNA damage.

Experimental studies have shown that tumor development proceeds through a series of multiple overlapping stages [12] defined as initiation (changes in DNA), promotion (expansion of numbers of cells with non-repaired or mis-repaired genes) and progression (growth of cells with accumulated genetic changes, some of which are in key genes that lead to cells that are aggressively malignant). In both experimental animal models and humans, there is a latency period between the original carcinogenic event and the development of a malignant tumor. This latency period may be due to several factors, including the complexity of the multistage tumor development process and/or the host's range of natural defenses against the carcinogenesis process.

This long latency period and the multi-stage tumor development process provide multiple opportunities for intervention to prevent and/or delay the development of malignant tumors (i.e., risk reduction).

Numerous scientific studies offer compelling evidence that formulations of mixtures of individual compounds acting at multiple stages of carcinogenesis are most likely to be optimal for cancer risk reduction. For example, epidemiologic studies have demonstrated that diet diversity or the overall pattern of dietary intake may have a greater impact on cancer risk than any one food [435, 436]. In addition, the administration of multiple agent formulations has been shown in some cases to result in synergistic effects, i.e., increased efficacy and potency over individual components, and generally to be significantly less toxic [13–20].

To take the example of colorectal cancer, the now widely accepted adenoma-to-carcinoma progression for colorectal cancer, originally proposed by Hill [255], provides multiple opportunities for intervention during carcinogenesis and makes this disease an excellent candidate for risk reduction strategies. Multiple molecular events are involved in colon carcinogenesis. Initially, the development of an adenoma requires that a stem cell must undergo a first "hit" (mutation), giving rise to a replicating population of abnormal cells, increasing the odds for additional "hits" and malignancy. Secondary to mucosal damage or as a result of high dietary energy intake, proliferation of abnormal colonic epithelial cells increases the opportunity for mutations to go unrepaired, resulting in the expansion of abnormal clones [256]. Based on these mechanisms, the colorectal cancer risk reduction strategy of the present invention is focused on both protecting cellular DNA from genetic alterations and enhancing endogenous mechanisms for regulating cell proliferation. Other examples of diseases susceptible to risk reduction according to the present invention include Type II diabetes, cardiovascular diseases, Alzheimers disease, osteoporosis, and many others. Likewise, other physical conditions that involve bodily attributes or performance issues, other than diseases, may be beneficially affected using the formulations and methods of the present invention.

SUMMARY OF THE INVENTION

In one aspect, the present invention includes a bidirectional, three-tiered screening process, which the inventors term "Ordered Research Information on Nutrients" (ORION), to identify and evaluate active components (i.e. nutrient ingredients) for use in the nutrient formulations of the invention. In the first tier of the screening process, ecologic and/or individual-based epidemiological data are examined to establish the patterns of association between diet and foods and disease. The disease under consideration may be a single specific disease, such as a particular form of cancer (e.g. colorectal cancer), or it may be a generalized disease class such as cancer diseases in general. Likewise, the disease under consideration may be a set of one or more specific diseases to be addressed in combination, such as colorectal cancer and lung cancer in combination, or lung cancer and a heart disease in combination. In the second screening tier, the principal (and preferably all) potentially active components from candidate foods and diets that may be implicated in delaying the onset of, or preventing or otherwise inhibiting, the disease (or the set or class of disease) in question are identified. In the third tier, data from studies on the active components are examined to determine their most likely mechanism(s) of action in the multiple pathways identified as important in potentially blocking some specific aspect of the disease process, for example the multi-phased carcinogenesis process. This process may driven from either and/or both directions, i.e., epidemiologic data may drive the process as summarized, or mechanistic evidence may be sufficiently compelling to move upwards to identify the active food ingredients in the target diet.

Because a plurality of active components will be identified as candidates for inclusion in the formulations of the invention, the chemical, pharmacological and toxicological interactions among such components (whether positive, negative or neutral in terms of ultimate therapeutic benefit), are resolved in arriving at the active components to be used in the final formulations of the invention. In addition, the candidate components for a particular disease under consideration may have therapeutically positive or negative cross-over effect(s) with respect to some other disease state. Such cross-over effects are likewise resolved in arriving at the active components to be used in the final formulations of the invention. In this manner, the screening method of the invention leads in a systematic fashion to nutrient formulations having a set of nutrient ingredients, contained in appropriate dosage amounts, that is optimally efficacious with respect to the individual disease or the entire disease set or disease class under consideration, while avoiding negative interactions and cross-over effects among different components and disease states.

Thus, the screening process of the invention utilizes evidence from the three tiers, optimizing the synergy and effectiveness of individual dietary supplements to maximize their integrated disease risk reduction potential in normal and high-risk populations. In selecting key ingredients for the formulations, mixtures of ingredients from target diets and/or mechanistic studies are chosen so as to maximize the synergistic effects, while avoiding or eliminating negative effects, across the spectrum of the disease (e.g. carcinogenesis) pathway(s), and physiologically relevant dosage levels for "normal" populations and more aggressive dosage levels for older and higher risk populations are selected. The formulations are preferably orally ingested by subjects, and are taken on a long-term, continuing and regular basis (especially daily or multiple times daily).

In another embodiment of the bidirectional, three-tiered screening process of the invention, a comprehensive analysis of findings from clinical and basic research is conducted in which geographic (preferably worldwide) disease incidence patterns and relevant dietary micronutrients are analyzed, followed by an in-depth evaluation of human dietary patterns associated with disease at specific organ or system site(s). Next, mechanistic studies of the candidate micronutrient in animals, cellular systems, and other "in vitro" models are analyzed and results are integrated for design and formulation decisions. The candidate compounds that are identified from this process are then considered relative to their efficacy in reducing the risk of a specific disease (or class or set of diseases) in relevant human studies and relative to factors such as their bioavailability and potential for synergy with other components. Based on such analysis and identification, final nutrient formulations are designed which optimize desired cellular protection and health synergies and product safety. In a related method, physical conditions influenced by elements of diet other than disease per se are considered according to the foregoing method, so as to screen for active components having:a beneficial effect on, for example, sports performance, beauty and cosmetic appearance, etc.

Still more particularly, the foregoing method may integrate global epidemiological and micronutrient data on cancer incidence and diet with a mechanistic understanding of human carcinogenesis to design organ-specific formulations for cancer risk reduction. Maximization of the synergistic effects of unique mixtures of ingredients is performed across all stages of the carcinogenesis process to optimize dosages based on risks. The method is employed to synthesize evidence from molecular and human epidemiologic studies to create a disease framework that describes the interplay between the molecular mechanisms and exogenous factors, including diet, that impact the carcinogenic process. Evaluation of the scientific literature within this framework results in the creation of an idealized chemoprevention list that includes a large collection of candidate risk reduction compounds that have demonstrated activity throughout the carcinogenic process. The candidate compound list is optimized for risk reduction at specific organ sites by evaluating both the carcinogenic processes unique to a given organ site and the bioavailability of a specific compound for that tissue type. The final product formulation is based on systematic evaluation of the scientific evidence for risk reduction in human populations.

In a related process of the invention, product design and development follows an iterated process that is divided into four rounds of development. In the first round of development, general knowledge regarding the regional distribution of cancer incidence, the unique diets or dietary patterns associated with regions of high and low incidence and the cellular mechanisms involved in disease development are reviewed. A list of candidate compounds for consideration generated. The next stage of product development focuses on a preliminary literature review to summarize current information and hypotheses regarding the development of organ specific cancers including disease etiology, detection, treatment and chemoprevention. A list of candidate compounds for the product formulation is thereby generated. In the third stage of product development, human, animal and in vitro data is evaluated for evidence of efficacy as chemopreventive agents. These investigations focus on mechanism of action, toxicity, safety, bioavailability, opportunities for synergy, formulation and dosage recommendations. The final product formulation is thereby established. In the final stage of product design, specific manufacturing specifications for the final product are ascertained.

In one preferred aspect of the invention, the formulation of the invention is a combination of nutrients useful in maintaining oxidative balance in a human or other mammalian subject, as described in more detail below. This formulation has balanced antioxidant properties and is particularly useful in reducing the risk of cancer diseases generally (i.e., as a disease class). Such a combination preferably comprises the nutrient ingredients specified below, wherein each nutrient ingredient is contained in a measured amount such that the proportional amount of each respective nutrient ingredient, relative to the other nutrient ingredient measured amounts in the combination, is as follows:

Vitamin E: 50–500 IU
Vitamin C: 60–500 mg
Selenium: 20–300 mcg
N-acetyl-l-cysteine: 500–2000 mg
Curcumin: 5–50 mg
Mixed Polyphenols: 500–1500 mg green tea extract, standardized to ≧60% polyphenols
Mixed Carotenoids: 500–2000 mg mixed vegetable extract, 1200 mg extract being equivalent in mixed carotenoid content to five vegetable servings.

Thus, in this preferred formulation the listed nutrient ingredient components are contained in the combination in relative amounts or ratios defined by the respective content ranges listed. It will be recognized that the absolute concentrations of the listed components may vary among different formulations of the combination, as for example between a dilute formulation and a more concentrated formulation, but the ratios (relative amounts) of the components will nevertheless remain as specified above.

As with other formulations and combinations of the present invention, some or all of the nutrient combination may be formulated in a unit dosage form, such as a pill, capsule or tablet form, or some or all of the combination may be in bulk form such as a powder or liquid (solution, suspension, emulsion, tincture, etc.) form. Preferably, the combination is formulated in a single unit dosage form (e.g. a pill), such that the subject can ingest one or more pills all of the same type according to the recommended administration schedule. Alternatively, depending on exigencies of formulation that are within the skill of the art given the present disclosure, the combination may be formulated in two or more discrete administration forms, preferably packaged together with instructions for use, that together constitute the described combination. For example, the combination may comprise two discrete unit dosage forms (e.g. a pill containing certain of the listed nutrient ingredient components and a capsule containing the remaining components; or a pill containing certain of the listed components and a liquid form containing the rest).

In a particularly preferred form of this oxidative balance formulation, the combination of nutrient ingredients is formulated in such a manner so as to allow the subject to receive daily dosages of the components in approximately the following amounts:

Vitamin E: 400 IU daily
Vitamin C: 500 mg daily
Selenium: 100 mcg daily
N-acetyl-l-cysteine: 1600 mg daily
Curcumin: 10 mg daily
Mixed Polyphenols: 1000 mg daily of green tea extract, standardized to ≧60% polyphenols
Mixed Carotenoids: 1200 mg daily of mixed vegetable extract equivalent in mixed carotenoid content to five vegetable servings.

It is preferred that the daily dosages of the specified components be within about ±20% of the amounts specified above, and more preferably within about ±10% of the amounts specified above. Such tolerance ranges for each of the separate components may be specified individually and need not all be the same.

With the exception of the two extract ingredients noted above, the masses specified in the right-hand column correspond to the masses of the specific components listed in the left-hand columns. In the case of selenium, for example, the specified dosage amount is approximately 100 mcg of the element selenium per se; this amount may be incorporated into the formulation in the form of (for example) l-selenomethonine which, of course, will weigh more than 100 mcg.

In this and other formulations of the invention, the components of the combination are preferably packaged together with instructions directing how the combination should be administered to the subject, including for example a timing schedule for administering the combination (e.g, the number of pills to be taken, the number of times each day they should be taken, etc.). Such instructions may also include information identifying the benefits and purposes of the formulation, indications for use, etc.

The above formulation and others of the invention may additionally include other active agents. For example, the formulation above may include one or more additional antioxidant agents beyond the antioxidant active components specified above. In another preferred embodiment, however, the active agents of the formulations (or more specifically, for example, the antioxidant active agents) will consist essentially of those specified in the present disclosure.

In another preferred aspect of the invention, the formulation of the invention is combination of nutrients useful in reducing colorectal cancer risk in a human or other mammalian subject, as described in more detail below. Such a combination preferably comprises the nutrient ingredients specified below, wherein each nutrient ingredient is contained in a measured amount such that the proportional amount of each-respective nutrient ingredient, relative to the other nutrient ingredient measured amounts in the combination, is as follows:

Salicin: 20–200 mg
Curcumin: 5–50 mg
Calcium: 200–2500 mg
Vitamin D: 100–1000 IU
Folic Acid: 200–1000 mcg
Vitamin $B_6$: 0.5–10 mg
Vitamin $B_{12}$: 0.1–100 mcg.

In a particularly preferred form of this colorectal health formulation, the combination of nutrient ingredients is formulated in such a manner so as to allow the subject to receive daily dosages of the components in approximately the following amounts:

Salicin: 120 mg daily
Curcumin: 10 mg daily
Calcium: 800 mg daily
Vitamin D: 400 IU daily
Folic Acid: 800 mcg daily
Vitamin $B_6$: 2 mg daily
Vitamin $B_{12}$: 6 mcg daily.

It is preferred that the daily dosages of the specified components be within about ±20% of the amounts specified above, and more preferably within about ±10% of the amounts specified above. Such tolerance ranges for each of the separate components may be specified individually and need not all be the same.

Other general aspects of this colorectal health formulation, as for example relative vs. absolute amounts of components and the quantitation thereof, the use of unit dosage and/or bulk forms, packaging and providing instructions for use, inclusion of additional active agents, etc., are as summarized above with respect to the oxidative balance nutrient formulation of the invention.

In still another aspect, the invention provides methods of reducing cancer risk generally, and methods of reducing colorectal cancer risk, comprising administering to a human or other mammalian subject a combination of nutrients as specified herein, preferably according to specified administration schedule.

Other aspects of the invention will become apparent from the detailed description below, and from the appended claims.

BRIEF DESCRIPTION OF THE DRAWINGS

FIG. 1 shows the chemical structure of vitamin E, in one preferred form.

FIG. 2 shows the chemical structure of vitamin C, in one preferred form.

FIG. 3 shows the chemical structure of a selenium nutrient ingredient, in one preferred form (l-selenomethionone).

FIG. 4 shows the chemical structure of NAC, in one preferred form (N-acetyl-l-cysteine).

FIG. 5 shows the chemical structure of curcumin.

FIG. 6 shows the chemical structure of several preferred green tea polyphenols.

FIG. 7 shows the chemical structure of several preferred vegetable/fruit carotenoids.

FIG. 8 shows the chemical structure of salicin.

FIG. 9 shows the chemical structure of vitamin D, in one preferred form.

FIG. 10 shows the chemical structure of folic acid.

FIG. 11 shows the chemical structures of vitamin $B_6$, including a preferred pyridoxine form.

FIG. 12 shows the chemical structure of vitamin $B_{12}$, in one preferred form.

DETAILED DESCRIPTION

Evidence is convincing that nutritional supplements containing a single component or vitamin are not effective in reducing the risk of cancer and numerous other diseases, but rather mixtures that capture several key nutritional elements of the diet function best in reducing, e.g., cancer risk [21]. Further, several specific components may optimize (and/or be required for) the anti-tumor or other disease reduction activity of another component.

For example, vegetables and fruits form a variable part of diets throughout the world and are rich in antioxidant compounds such as selenium, N-acetyl-l-cysteine and vitamins A, E, C, and carotenoids (beta-carotene, lycopene and others). In addition, specific plant materials, known as phytochemicals, also act as antioxidants in humans. Vitamin C is required to prevent the auto-oxidation of vitamin E, and vitamin E optimizes the role of selenium as an antioxidant. These synergies are critical in optimizing, for example, the cancer risk reduction potential of nutritional supplements. Based on this recognition, the screening process of the present invention includes, in one aspect, identifying and selecting a range of vitamins and active botanicals that act in specific phases of the carcinogenesis process. Thus, one guiding principle in the development of the formulations of the invention is to achieve a balance of multiple active component nutrients. Specifically in the context of cancer reduction, for example, antioxidant formulations are designed according to the invention to achieve an appropriate balance between antioxidants and pro-oxidants (i.e., an oxidative balance). Furthermore, formulations have been developed for specific risk and "normal" populations, and dosages reflect the general differential needs of these groups.

EXAMPLE 1

Antioxidant (Oxidative Balance) Formulations of the Invention

In one aspect, the scientific approach of the invention is based on utilizing evidence from the three screening tiers described above to optimize the synergy and effectiveness of individual dietary supplements to maximize their integrated cancer risk reduction potential in normal and high-risk populations. As an example, a preferred antioxidant formulation of the invention useful in cancer risk reduction is composed of seven key antioxidants that act at all phases of carcinogenesis to protect against DNA damage during initiation and/or injury to cell membranes and other vital structures during promotion and progression. All of the ingredients preferably represent natural forms of specific vitamins and nutrients and are selected to produce maximum synergy. The described antioxidant formulations provide for the maintenance and/or restoration of physiologic balance, i.e. oxidative balance, in all populations. Such antioxidant formulations are designed for the "normal" healthy adult population (20–40 years of age) and for all older and high-risk populations to maintain oxidant-antioxidant balance. The antioxidant formulations minimize cellular oxidative damage from free radicals and reactive oxygen species, while maintaining the benefits of oxidants and pro-oxidants in the cell. The antioxidant formulations are designed to maintain oxidative balance when taken over an extended period of years in all populations, with no concern for toxicity.

A natural consequence of aerobic metabolism is the production of highly reactive molecules called free radicals and a related subclass of molecules, reactive oxygen species (ROS). Although these reactive molecules are capable of causing cellular oxidative damage associated with carcinogenesis, some of them also play critical roles in stimulating important cellular functions. As a result of this dual biological function, cells utilize a system of free radical scavengers and enzymes to maintain a balance of free radical formation and removal. Maintaining oxidative balance is important for minimizing oxidative damage to cells and tissues (cancer risk) while preserving the important signaling properties associated with these some of these reactive molecules.

Plants have developed extensive systems of protection against the free radicals and ROS that are generated as byproducts of oxidative metabolism. A plant-based diet provides humans with their major evolutionary protective advantage against cellular damage from life in an oxygen rich environment, specifically protection from free radicals and ROS. Many of the agents found in fruits and vegetables are still the best source of protection against damage by free radicals and ROS, and ultimately against the development of cancer. Scientific evidence has demonstrated that antioxidants can inhibit oxidative damage to DNA to prevent initiation and protect cells and tissues from oxidants and pro-oxidants during the promotion and progression phases of carcinogenesis.

The metabolic production of ROS both directly and indirectly modulates cellular processes involved in carcinogenesis [22]. ROS are capable of damaging important cellular components such as DNA, proteins and lipids. ROS include hydroxyl radical, superoxide anion radical, hydrogen peroxide, singlet oxygen, hypochlorite, nitric oxide radical and peroxynitrite.

Antioxidants protect proteins, lipids and DNA from oxidative damage by neutralizing free radicals and ROS that are generated during normal cellular metabolism and during environmental exposure to carcinogens. For example, vitamin E is the major lipid soluble antioxidant that protects cell membranes against the destructive chain reactions associated with lipid peroxidation. Vitamin C acts by quenching ROS and can also regenerate the reduced antioxidant form of vitamin E. Trace minerals (such as selenium) can also act as antioxidants due to their incorporation into enzymes such as the glutathione peroxidases and superoxide dismutases, which act to convert ROS to less reactive components.

Since free radicals and ROS are a natural consequence of aerobic metabolism, cells utilize a system of free radical scavengers and enzymes to maintain the balance of free radical formation and removal. Maintaining oxidative balance is important for minimizing oxidative damage to cells and tissues while preserving the important signaling properties associate with ROS [23, 24]. The importance of oxidative balance for human health was first proposed by McCord, based on apparently conflicting observations with regard to the use of the antioxidant enzyme, superoxide dismutase, as a protective therapeutic agent [23, 24]. Experimental studies demonstrated that a balance between the production of superoxide radical and the amount of superoxide dismutase. present was critical for optimal cellular or organismal function. Thus, the oxidant/antioxidant balance represents an important cellular equilibrium that minimizes oxidative cellular damage while preserving important cellular and signaling functions associated with ROS.

The cellular oxidant-antioxidant balance is maintained by a series of enzymes including superoxide dismutases, glutathione peroxidases, catalases and several vitamins and micronutrients that modulate the kinetics of initiation, propagation and termination of free-radical mediated events. One approach to maintaining oxidative balance is to prevent the formation of the initiating radical species or facilitating its removal. Compounds and enzymes that effectively scavenge reactive oxygen and thus block the subsequent chain reaction can effectively inhibit propagation reactions that lead to the amplification of the initial radical-dependent event.

Based on the multi-stage model of carcinogenesis (initiation, promotion and progression), compounds that act at the initiation stage would provide a first line of defense for cancer risk reduction. Compounds in this class would include substances that reduce the synthesis of carcinogens in the body (e.g., vitamin C, which inhibits the formation of nitrosamines in the stomach); chemicals that inhibit the metabolic activation of carcinogens by Phase I enzymes or enhance their detoxification by Phase I or Phase II enzymes (e.g., indoles and carotenoids, cruciferous vegetables); antioxidants that scavenge free radicals (e.g., selenium and α-tocopherol); and chemicals that trap ultimate carcinogens, preventing their interactions with DNA.

Suppressing agents act to inhibit the carcinogenic process after initiation and appear to work through a variety of mechanisms. These include alterations in gene expression, cell proliferation and clonal expansion, as well as induction of differentiation, senescence or apoptosis. Vitamin E and many antioxidants in fruits and vegetables have demonstrated activity post-initiation. Vitamin E is especially important in maintaining the integrity of membranes and blocking lipid peroxidation. Experimental and epidemiological studies suggest in the context of the present invention that other substances, such as organo sulfur compounds (e.g., N-acetyl-l-cysteine (NAC), curcumin in turmeric/curry, polyphenols in green tea, and various protease inhibitors), may also be useful in preventing tumor formation at stages post-initiation. For example, NAC specifically acts as an intermediate in the formation of glutathione, a key cellular protective mechanism against oxidative damage.

As a result of screening investigations according to the present invention, antioxidant formulations have been identified adhering to the premise that a combination of compounds with a variety of antioxidant activities would provide optimal synergistic protection from oxidative damage and promote oxidative balance. It is believed that this concept offers the most promising approach to reduce overall cancer risk. The following represents the key summary rationale for inclusion of specific ingredients in the antioxidant formulations of the invention:

Vitamin E (as d-α-tocopherol succinate)—Vitamin E is a lipid soluble compound and the most significant antioxidant activity of vitamin E is localized to cellular membranes.

Vitamin E maintains oxidative balance by protecting cellular membranes from lipid peroxidation by terminating ROS initiated chain reactions and complementing the antioxidant activity of selenium.

Vitamin C (as calcium ascorbate)—Vitamin C is water-soluble, found in aqueous cellular compartments and is a first line of defense against direct free radical exposure (e.g., radiation, sunlight). Vitamin C maintains oxidative balance by effectively scavenging free radicals produced in the aqueous cellular cytoplasm and by recycling (protecting) vitamin E in cellular membranes.

Selenium (as l-selenomethionine)—Selenium is an essential nonmetallic trace element that functions as an essential component of antioxidant enzymes that maintain oxidative balance by removing DNA-damaging hydrogen peroxide and lipid hydroperoxides. These selenium-dependent enzymes, and glutathione are associated with both the cytosolic and membrane compartments of the cell.

N-acetyl-l-cysteine (NAC)—A water soluble organosulfur compound that promotes detoxification and is a precursor and stimulant of glutathione synthesis, a major defense mechanism in maintaining oxidative balance. The main antioxidant activity associated with NAC aside from detoxification is protection of DNA from oxidative damage.

Curcumin (from turmeric extract)—Maintains oxidative balance by acting as a general antioxidant scavenger of ROS and protects membranes from lipid peroxidation.

Mixed Polyphenols (from green tea extract)—Inhibit the formation of free radicals and reduce the level of lipid peroxidation by stimulating the production of Phase II detoxifying enzymes including glutathione reductase, glutathione peroxidase, glutathione S-transferase, catalase and quinone reductase to maintain oxidative balance.

Mixed Carotenoids (from mixed vegetable extract)—Maintain oxidative balance by providing membranes with a variety of scavengers of ROS. The chemical structure of carotenoids provides multiple sites for interaction with free radicals and ROS. The chemical diversity of this mixture of compounds optimizes the reactivity, uptake and tissue distribution in biological systems. Carotenoids are lipophilic and are localized to cellular membranes.

The preferred antioxidant formulation of the invention is composed of seven principal antioxidants (see Table 1 below), that act throughout the carcinogenesis process to maintain cellular oxidative balance. As explained above, the antioxidants protect proteins, lipids and DNA from oxidative damage by neutralizing free radicals and ROS that are generated during normal cellular metabolism and during environmental exposure to carcinogens. The key antioxidants in the present antioxidant formulation act to protect against DNA damage during initiation and/or injury to cell membranes and other vital structures during promotion and progression. All of the ingredients preferably represent natural forms of specific vitamins and nutrients and have been selected to produce maximum synergy.

The recommended daily amount is preferably taken in two divided doses. Dosage levels and timing of doses are recommended to maximize synergy of the individual components and insure their activity, as the half-life of most of the antioxidants is 6–12 hours. The composition and dosages are preferably formulated to approximate natural sources and to optimize the synergy of the components and interactions of the individual components.

The antioxidant formulation as exemplified below is intended as a general formulation for use by all populations, including especially individuals having low or normal risk to cancer. As indicated herein, dosages will typically be customized for individuals that have a higher risk of cancer, for example older individuals, those with a genetic predisposition to one or more cancer diseases, smokers, etc. Furthermore, it will be apparent given the present disclosure that dosages can readily be adjusted upward or downward for subjects having abnormally high or low body weight or extremes of diet.

TABLE 1

Antioxidant Formulation Composition for the General Population - Component Ranges and Recommended Dose.

| Compound (and preferred source form) | Component Ranges (Relative) | Daily Dose |
|---|---|---|
| Vitamin E (as d-α-tocopherol succinate) | 50–500 IU | 400 IU |
| Vitamin C (calcium ascorbate) | 60–500 mg | 500 mg |
| Selenium (as 1-selenomethionine) | 20–300 mcg | 100 mcg |
| N-acetyl-1-cysteine (NAC) | 500–2000 mg | 1600 mg |
| Curcumin (from turmeric extract, standardized to 95% curcuminoids) | 5–50 mg | 10 mg |
| Mixed Polyphenols (from green tea extract) | 500–1500 mg extract standardized to ≧60% polyphenols | 1000 mg extract standardized to ≧60% polyphenols |
| Mixed Carotenoids (from mixed vegetable extract) | 500–2000 mg mixed vegetable extract(s) | 1200 mg mixed vegetable extract(s), equivalent in mixed carotenoid content to that found in 5 servings of vegetables |

Abbreviations: IU, international unit; mcg, micrograms

It is preferred that the daily dosages of the specified components be within about ±20% of the amounts specified above, and more preferably within about ±10% of the amounts specified above. Such tolerance ranges for each of the separate components may be specified individually and need not all be the same.

As indicated above, it is preferred that the active components of the formulations of the invention be obtained from natural sources, if such are available, as for example the sources indicated in Table 1 above or elsewhere herein. It will be recognized in view of the present disclosure, however, that alternative sources of these and other active components may be utilized, including synthetic materials, components obtained from natural (especially plant, or yeast or bacterial) sources different from those mentioned herein, and mixtures of different sources whether natural or synthetic. For example, in the case of the Mixed Carotenoid component specified above, it is contemplated that some or all of the preferred carotenoids shown in FIG. 7 may be chemically synthesized and combined (optionally with one or more naturally-derived carotenoids) to form a "cocktail" that approximates the natural extract mixture specified above.

The antioxidant formulation exemplified above was identified by the present inventors using the three-tiered screening method described herein. The application of that method in the context of the exemplified antioxidant formulation will now be described in more detail.

Vitamin E

The chemical structure of the preferred form of vitamin E is shown in FIG. 1. The preferred form of vitamin E is as follows:

Form: as d-α-tocopherol
CAS Name (9CI): 3,4-Dihydro-2,5,7,8-tetramethyl-2-(4,8,12-trimethyltridecyl)-2H-1-benzopyran-6-ol Vitamin E is a lipid soluble antioxidant representing one of the body's primary defenses against cellular oxidative damage. All vitamin E in the human body is derived from the diet and includes multiple chemical forms. Major dietary sources of vitamin E are vegetable oils, margarine and shortening, with nuts, seeds, whole grains and wheat germ providing additional sources. "Vitamin E" includes eight different chemical forms: four tocopherols and four tocotrienols. The most biologically active form of vitamin E is α-tocopherol [30].

Vitamin E localizes in cellular membranes and is the major chain-breaking antioxidant to protect membranes against lipid peroxidation, especially reactions initiated by the very destructive hydroxyl radical (OH.) [31]. Vitamin E protects cell membranes at an early stage of free-radical attack via its ability to quench free-radical activity [32–34]. Epidemiologic studies indicate that vitamin E intake is associated with a reduced risk of cancer at multiple sites. A nutritional intervention trial in Linxian (China) found that nutritional doses of vitamin E in combination with β-carotene and selenium were associated with a 13% decrease in mortality from all cancers and a 21% decrease in mortality from stomach cancer [35]. Vitamin E intake has also been associated with a decreased incidence of colon cancer [36, 37] and 34% decrease in the incidence of prostate cancer [37].

In addition to vitamin E's antioxidant activity, increased vitamin E intake has also been shown to enhance immune function that may promote the body's defense against cancer. Other properties that may contribute to cancer risk reduction include the ability of vitamin E to inhibit nitrosamine formation [38].

Vitamin E, in combination with other antioxidants (e.g., sodium selenite and/or retinoids), has demonstrated enhanced chemopreventive activity. Vitamin E complements the antioxidant activity of selenium and is also known to have a sparing effect on β-carotene [39]. Thus, it has been suggested that the most effective strategy is to combine vitamin E with other antioxidants or retinoids [40].

Regarding pharmacology and toxicology, vitamin E has many of the characteristics that have been identified for optimal chemopreventive agents. Vitamin E has been shown to accumulate in many tissues including fat [218]. α-Tocopherol is carried by lipoproteins in the blood and levels of vitamin E in serum are directly related to dietary and supplemental intake [34]. In addition, vitamin E has extremely low toxicity, making it an excellent candidate for chemoprevention [219].

The bioavailability of natural forms of vitamin E is higher than that for synthetic forms. The discrimination between different forms of vitamin E is not due to differences in absorption but is due to the specificity of enzymes involved in vitamin E transfer between membranes [220–223]. Natural vitamin E, obtained from food sources, is a single steroisomer designated RRR-α-tocopherol or d-α-tocopherol. Synthetic vitamin E is produced commercially and contains a mixture of eight different steroisomers. The transfer proteins important for regulating plasma levels of vitamin E preferentially recognize d-α-tocopherol. Thus, natural vitamin E is more bioavailable and is retained in body tissues significantly longer than synthetic vitamin E [41, 224].

The most serious side effect related to vitamin E intake is antagonism of vitamin K activity, which has been demonstrated in both preclinical and clinical studies. A significant concern is bleeding in vitamin K-deficient patients after prolonged daily intake of >800 IU [225, 226]. Although high doses of vitamin E are required, this could represent a serious complication in combination with anticoagulant therapy or vitamin K malabsorption syndrome [40].

The US Pharmacopoeia monograph [227] has defined vitamin E for drug use as d- or d,l-α-tocopherol, d- or d,l-α-tocopherol succinate or d- or d,l-α-tocopherol acetate [226, 228]. The following compounds have GRAS status as food additives; d- or d,l-α-tocopherol and α-tocopherol acetate.

It has been demonstrated a-tocopherol and ascorbic acid synergistically inhibit the oxidation of liposomal membranes [229, 230].

Vitamin C

The chemical structure of Vitamin C is shown in FIG. 2. The preferred form of Vitamin C is as calcium ascorbate. The molecular weight of ascorbic acid is 176.14. The chemical core of vitamin C is composed of a five-membered lactone ring containing a bifunctional ene-diol group and an adjacent carbonyl group. Ascorbate is highly soluble in water (~1 g dissolves in 3 ml of water). It is insoluble in nonpolar organic solvents such as benzene, petroleum, ether, fats and their solvent [25].

The unusual chemical structure, thermodynamic redox potential and rapid reaction kinetics observed for ascorbate support its unique role as the terminal small molecule antioxidant in biological systems [41]. Ascorbic acid (ASC) exists in three different redox states in biological systems: ASC, semidehydroascorbate (SDA), and dehydroascorbate (DHA). DHA is formed as the result of two consecutive and reversible, one-electron oxidation processes. Because the unpaired electron is in a highly delocalized π-system, the ascorbate radical is relatively unreactive. Thus, the thermodynamics and kinetics of ascorbate chemistry make ASC a superior biological donor antioxidant [41]. SDA and DHA are recycled via reduction back to ascorbate by endogenous enzyme systems.

There is significant evidence demonstrating that ascorbate enhances the antioxidant action of vitamin E by reducing reduction of the tocopheroxyl radical [42–47]. The reactions between the tocopheroxyl radical and ascorbate provide a mechanism for exporting oxidative free radicals away from the cellular membranes. In essence, tocopherols protect membranes by stopping propagation reactions of lipid peroxy radicals and ascorbate acts by protecting the membrane against possible damage from the tocopheroxyl radical. Thus, ascorbate helps to maintain oxidative balance by scavenging free radicals and recycling the useful forms of other antioxidants, such as vitamin E.

Epidemiologic data suggest an inverse relationship between cancer risk and dietary vitamin C intake [1, 6, 8, 9]. Numerous observational studies have found that lung cancer risk was lower among people with highest levels of vitamin C intake. Similar observations were made concerning vitamin C intake and the risk of colorectal cancer, breast cancer, oral and esophageal cancer and stomach cancer [3].

Regarding pharmacology and toxocology, humans require dietary intake of ascorbic acid, and uptake is mediated by sodium-dependent transport mechanisms [231]. Absorption of dietary ascorbate is nearly complete [232], is half-maximal at about 1 mM and shows saturation characteristics. Evidence suggests that ascorbic acid is mostly free in the cytoplasm of cells and that cells have active uptake mechanisms to concentrate ascorbic acid in tissues. Vitamin C has low toxicity and relatively few side effects [233].

Selenium

The chemical structure of a preferred form of selenium is shown in FIG. 3. The preferred form of selenium is as follows:

Form: l-selenomethionine
CAS Name (9CI): (S)-2-Amino-4-(methylseleno) butanoic Acid
Molecular Weight: 196.1

The observation that the geographical distribution of selenium in forage crops was inversely associated with cancer mortality rates in the US indicated for the first time that selenium may be involved in cancer risk reduction [48]. It was subsequently demonstrated in multiple studies using a variety of populations that cancer mortality was inversely associated with selenium intake for cancers of the colon, rectum, breast, ovary and lung [49–51]. Scientific evidence also demonstrates that cancer patients are generally of lower selenium status than healthy controls supporting an association between selenium status and cancer risk [52, 53]. In addition, low serum selenium levels have been associated with increased cancer risk for multiple sites [54–60]. Thus, there is significant epidemiological evidence demonstrating an inverse association between nutritional selenium status and cancer risk, suggesting that low selenium status may contribute to cancer development.

Three sets of clinical intervention trials conducted in China have shown that selenium intake is associated with cancer risk reduction. Two studies evaluating the effect of supplemental selenium intake on liver cancer risk in individuals carrying the hepatitis surface-antigen found that selenium treatment eliminated liver cancer incidence among this group [61]. A third study demonstrated that selenium treatment had modest protective effects against total and stomach cancer mortality [35]. Finally in a decade long, double blind, placebo controlled, US trial, selenium supplementation was associated with lower incidences of total non-skin cancer, including cancer of the lung, colon-rectum and prostate as well as overall cancer mortality rate [62].

Animal and in vitro evidence suggests that selenium has two fundamental roles in cancer prevention: as an essential component of antioxidant enzymes and as an anticarcinogenic metabolite (reviewed in [63]). Selenium is an essential component of the catalytic reaction center of glutathione peroxidases [64]. These selenium-dependent enzymes function to maintain oxidative balance by removing DNA-damaging hydrogen peroxide and lipid hydroperoxides. Many proteins contain selenium in the form of selenocysteine, which is incorporated by the co-translational modification of transfer RNA-bound serine at certain loci encoded by specific uracil-guanine-adenine codons [65, 66].

In addition to antioxidant activities, selenium compounds have anti-initiation effects through altered carcinogen metabolism, as well as antiproliferative effects resulting from inhibition of DNA [67] and protein synthesis [68, 69] and altered immune function [70, 71].

Regarding pharmacology and toxicology, l-selenomethionine is readily absorbed from the gastrointestinal tract [234]. L-selenomethionine is better absorbed and has a slower whole-body turnover when compared to selenite (inorganic selenium) [234]. Multiple studies demonstrate that supplementation with l-selenomethionine results in increased plasma and tissue levels of selenium compared to other forms of selenium [235, 236].

The form of supplemental selenium may play a significant role in toxicity. For example, original research on the role of selenium in the diet focused on toxic effects at high does [237]. The most effective approach to reduce possible toxic effects of selenium is to use selenium in the form of seleno-organic compounds such as selenomethionine [238] that insures the secure binding of the selenium atom. The associated methionine aids in the safe metabolism of selenium [239] and it is this form that is preferred in the formulations of the present invention.

Selenium appears to have a 10-fold range of safety between physiological and toxic levels in humans. The human maximum tolerated dose (MTD) of dietary selenium is estimated to be 819 $\mu$g selenium/day or 15 times the RDA.

N-Acetyl-l-cysteine (NAC)

The chemical structure of NAC shown in FIG. 4. The preferred form of NAC is as follows:

Form: l-isomer of N-acetylcysteine
CAS Name (9CI): N-Acetyl-l-cysteine
Molecular weight: 163.2

N-Acetyl-l-cysteine (NAC) is a natural sulfur-containing amino acid derivative found in a variety of foods including fruits and vegetables. NAC is an acetylated variant of the amino acid L-cysteine that has free radical scavenging activity, stimulates glutathione (GSH) synthesis and promotes detoxification. Historically, NAC has been used as a mucolytic agent in a variety of respiratory illnesses and also improves conditions characterized by decreased GSH (acetaminophen overdose) and/or increased oxidative stress, such as HIV infection, cancer, heart disease and cigarette smoking.

The diverse array of pharmacological uses for NAC center on the nucleophilicity and redox interactions of the sulfhydryl group of the molecule. Oral administration of NAC supplies the cysteine required to replenish GSH. GSH is a ubiquitous tripeptide that provides the principal intracellular defense against oxidative stress [72] and participates in the detoxification of many molecules [73].

NAC has demonstrated both in vitro and in vivo antimutagenic [74] and anticarcinogenic activities. DNA adduct formation in rats was inhibited by NAC following acetylaminofluorene or benzo[a]pyrene administration [74, 75]. Orally administered NAC was also shown to depress the numbers of DNA adducts formed in rat tracheal epithelial cells after extended periods of exposure to tobacco smoke [76]. In addition to protecting DNA from damage, NAC is also able to protect the function of enzymes involved in DNA replication and repair [77]. Evidence demonstrates that in addition to exhibiting protective effects at the initiation stage of chemical carcinogenesis, NAC may also inhibit the invasiveness of malignant cells [78].

NAC has demonstrated anticarcinogenic activities in a variety of animal models. NAC has been shown to decrease the formation of lung tumors in urethane-treated mice [79], prevent the formation of AAF-[80] and hydrazine-[81] induced sebaceous squamocellular carcinomas of the symbol glands of rats, and inhibit azoxymethane induced colon cancer in rats [82]. Administration of NAC has also been shown to reduce the incidence of experimentally induced intestinal tumors [81]. A large multi-center clinical trial has been initiated to study the chemoprotective potential of NAC in the development of second primary tumors in patients treated for lung, larynx and oral cancer [83].

The main biological activity associated with NAC is its ability to promote oxidative balance by stimulating GSH synthesis, enhancing glutathione S-transferase activity, and promoting detoxification [84]. In vitro and in vivo studies have demonstrated that NAC is able to enhance the intracellular biosynthesis of GSH [85–89]. In humans, NAC administration was associated with elevated circulatory levels of GSH [90–92]. Cell culture experiments have also shown that NAC promotes the uptake of cystine from the culture medium for cellular GSH biosynthesis [85]. In vivo, NAC has been shown to increase intracellular GSH levels in erythrocytes, liver and lung cells, [86], and to replenish GSH stores following experimental depletion [87]. In humans, metabolism of acetaminophen is associated with an increased demand for GSH that can be offset by administration of NAC [92].

In addition to stimulating GSH synthesis and carcinogen detoxification, NAC is a powerful scavenger of hypochlorous acid, and is capable of reducing hydroxy radicals, hydrogen peroxide and the superoxide anion [93, 94]. NAC has been shown to reduce oxygen toxicity of the lung caused by prolonged administration of 100% oxygen in animal studies [95]. While the sulfhydryl group is responsible for a great deal of the metabolic activity, the acetyl-substituted amino group makes NAC more stable against oxidation [96].

Recently, NAC has been shown to affect gene regulation by redox-sensitive transcription factors [97–99]. This type of gene regulation has been shown to modulate cellular adaptation to oxidative imbalance as well as control cell differentiation and cell deletion by apoptosis [100–105].

Thus, based on its antioxidant and detoxifying properties, as well as apparent safety and lack of major side effects [106, 107], NAC has been determined to be important for the maintenance of oxidative balance.

Regarding pharmacology and toxicology, NAC is rapidly absorbed following an oral dose. Researchers have estimated the bioavailability of the intact NAC molecule to be only between 4–10% [240–242]. The low oral bioavailability of NAC may be due to sulfhydryl reactivity with proteins [242] and deacetylation in the intestinal mucosa and lumen [243]. Deacetylation of NAC is specific for the L-isomer, with the D-isomer being poorly metabolized in human tissues. Cysteine and inorganic sulfite appear to be the major metabolites of NAC found in the liver. The plasma half-life of free NAC is estimated to be about 2 hours with virtually no NAC detected 10–12 hours post-administration [242]. Following oral administration, plasma NAC concentrations peak in less than one hour [241, 242].

NAC has been traditionally utilized in a number of human diseases, is well tolerated and elicits few side effects. As with most agents, the pharmacokinetics of NAC is altered in patients with chronic liver disease. These compromised individuals exhibit increased serum concentrations of NAC due to a decreased ability to clear NAC from the blood stream following an intravenous dose [244].

The $LD_{50}$ of NAC is 7888 mg/kg in mice and greater than 6000 mg/kg in rats following oral doses. In animal fertility studies, no adverse effects were reported at does up to 250 mg/kg and no teratogenic effects were observed at does as high as 2000 mg/kg. In these same studies, NAC had no adverse effects on delivery, physical development or lactation.

Curcumin

The chemical structure of curcumin is shown in FIG. 5. Preferred forms of curcumin are as follows:
 Form: *Curcuma longa*, Aqueous Extract
  *Curcuma longa*, Acetone/Methanol Extract
  *Curcuma longa*, Volatile Oil
 CAS Name (9CI): (E,E)-1,7-Bis(4-hydroxy-3-methoxyphenyl)-1,6-heptadiene-3,5-dione
 Molecular weight: 368.4

Food-grade curcumin is composed three similar compounds, curcumin (69–77%), demethoxycurcumin (17%) and bis-demethoxycurcumin (3–6%) [26]. The pure form of curcumin (>98%) is equally effective as the food-grade in a rat colon model for carcinogenesis [26]. Particle size has been demonstrated to affect the bioavailability of curcumin. Pure curcumin is available in a defined homogeneous particle size from, for example, Gene Print, Inc. A preferred curcumin extract is one that is standardized to 95% curcuminoids).

Curcumin (diferuloyl methane) is a phenolic antioxidant identified as the major pigment in turmeric, curry and mustard. Turmeric, the powdered rhizome from the root of the plant *Curcuma longa*, contains approximately 1–5% curcumin. Turmeric and curcumin are used as spices in foods and turmeric has been used an herbal remedy in the treatment of inflammatory diseases. Curcumin has been shown to exhibit a wide range of biological activities including both anti-inflammatory [108–110] and antioxidant properties [111, 112].

There is significant evidence in animal studies demonstrating that curcumin can inhibit tumors in several organs [26, 113, 114]. In addition, curcumin has demonstrated chemopreventive activity in all three stages of carcinogenesis [115]. Curcumin has been shown to inhibit chemically induced carcinogenesis in the skin, forestomach and colon when it was administered during initiation and/or post initiation stages [26, 116–119]. Curcumin was also shown to be effective when administered during the promotion/ progression stage and suppressed the incidence and multiplicity of noninvasive adenocarcinomas and also strongly inhibited the multiplicity of invasive adenocarcinomas of the colon [115]. Thus, the chemopreventive activity of curcumin was observed when it was administered prior to, during and after carcinogen treatment as well as when it is given only during the promotion/progression phase of colon carcinogenesis [115].

Curcumin is the major antioxidant substance in turmeric. Curcumin exerts a protective activity on cells suffering from hydrogen peroxide ($H_2O_2$)-induced oxidative stress [120, 121]. Curcumin has been shown to scavenge ROS such as hydroxyl radical [122–126], superoxide anion [126, 127], and singlet oxygen [128]. Curcumin interferes with lipid peroxidation [122, 129–137] and nitrite/nitrogen oxide production [138, 139]. Curcumin is also an inhibitor of neutrophil responses [127] and of superoxide generation in macrophages [140].

In addition to antioxidant properties, curcumin has been shown to exhibit a diverse array of metabolic, cellular and molecular activities including inhibition of arachidonic acid formation and its further metabolism to eicosanoids [118, 141–143]. Evidence also suggests that curcumin acts on pathways that may inhibit cell proliferation [144] and enhance apoptosis [145]. Curcumin inhibits several mediators and enzymes involved in cell mitogenic signal transduction pathways [146] and activator protein-1 and nuclear factor κB activation [147–149].

Regarding pharmacology and toxicology, curcumin is generally recognized as safe (GRAS) for use as either the powder (1–5% curcumin) or as the oleoresin (organic extract containing 40–85% curcumin) [245]. Purified curcumin itself is not on the GRAS list, and has been given a temporary acceptable daily intake (ADI) level of 0.1 mg/kg-bw (0.27 μmole/kg-bw) by the Joint FAO/WHO Expert Committee on Food Additives pending the completion of carcinogenicity and reproductive toxicity studies [245].

Curcumin was shown to be safe in preclinical studies when administered orally [245]. In addition, curcumin is presumed to be safe due to a long history of human usage in Asia—up to an estimated 95 mg/day as the food additive turmeric [245]. Unlike synthetic NSAIDs which also exhibit COX inhibition, curcumin does not (in general) produce gastrointestinal toxicity, even at very high doses, which provides an advantage over synthetic agents [245]. Concomitant administration of piperine increased the bioavailability of curcumin by 2000%. Thus piperine enhances the serum concentration, extent of absorption and bioavailability of curcumin in both rats and humans with no adverse effects [246].

Additional details regarding curcumin are set forth below in the discussion of the colorectal health formulations of the present invention, and are incorporated into this discussion.

Green Tea Extract

Chemical structures for various polyphenols of green tree (e.g. *Camellea sinensis*) extract are shown in FIG. 6. The preferred form is as follows:

Form: Mixed Polyphenols

CAS Names (9CI): See FIG. 6.

Polyphenols represent a class of pharmacologically active antioxidant compounds present in green tea. FIG. 6 summarizes the structures of some of the important polyphenols (complex catechins) present in green tea [27]. The polyphenol content in tea leaves is dependent on the genetic makeup of the plant as well as environmental factors such as climate, light, rainfall, temperature, nutrient availability and leaf age. Polyphenols represent 30–35% of the dry leaf. Polyphenols are water soluble, colorless substances with an astringent taste. The preferred source of green tea is that used in numerous scientific studies to examine its effects on cancer risk.

Green tea is produced from the leaves of the tea plant, *Camellia sinensis*, an evergreen shrub in the family of Theaceae. Complex catechins represent the main antioxidant polyphenols found in tea leaves. Tea leaves also contain a polyphenol oxidase that is activated when the leaves of the plant are bruised during chopping and rolling at harvest. The polyphenol content of green tea is greater than that of black tea due to inactivation of the polyphenol oxidase by briefly heating or steaming the leaves prior to drying. Green tea is consumed primarily in Asian countries, such as Japan, China, and India and a few countries in North Africa and the Middle East [150, 151]. The concentration of tea is usually a 1–2% solution. Individuals drinking four or more cups of tea (extracted from 10 g tea) per day have the equivalent benefit of eating two fruits or vegetables [41].

Green tea contains polyphenols that act as powerful antioxidants. The four major catechins in green tea are (−)-epicatechin, (−)-epicatechin-3-gallate, (−)-epigallocatechin (EGC), and (−)-epigallocatechin-3-gallate (EGCG). EGCG is one of the most important compounds in green tea and it accounts for 40% of the polyphenolic mixture [150]. One cup of green tea usually contains about 300–400 mg of nontoxic polyphenols.

Epidemiological evidence demonstrates that increased consumption of green tea is associated with significant decreases in cancer risk at multiple sites [150, 152, 153]. Increased green tea consumption was inversely associated with cancers of the stomach and esophagus [154–158], lung [159], pancreas [160], colon and rectum [160, 161]. In one study, the inverse association between green tea intake and stomach cancer incidence did not depend on the age when habitual tea drinking started, suggesting that the components found in green tea may disrupt gastric carcinogenesis at the intermediate and late stages of carcinogenesis [156].

Although still under investigation, evidence indicates that the compounds in green tea are active at all three stages of cancer development including initiation, promotion and progression. Green tea and components of green tea extracts have been shown to inhibit initiating events by decreasing the metabolic formation of ROS and by repressing the catalytic activities of several P450 enzymes and increasing the levels of Phase II detoxifying enzymes [162–165]. For example, the levels of detoxifying enzymes (glutathione reductase, glutathione peroxidase, glutathione S-transferase, catalase and quinone reductase) were significantly increased in the lungs, liver and small intestines of mice that ingested a polyphenolic fragment isolated from green tea in the drinking water [162]. EGCG, the major component of green tea has also been associated with the inhibition of chemically induced lipid peroxidation and free radical formation [125, 139, 166–171].

Several mechanisms may be involved in the anti-initiation and anti-promotion activities of green tea. In addition to the antioxidant activity associate with green tea, research results indicate that components in green tea can inhibit growth and developmental aspects of transformed cells. These activities were associated with the inhibition of estrogen/receptor interactions [152], stabilization of gap junctions important for preserving intercellular communication [172, 173] and inhibition of PKC and cellular proliferation [152, 172, 174, 175]. Tea has also been shown to prevent the formation of nitrosamides that have been shown to induce stomach cancer in animal models [176, 177].

Regarding pharmacology and toxicology, There are no specific toxicity issues currently identified for green tea [247]. Given the prolonged consumption of green tea in Asian cultures, safety should not be an issue. It has been suggested, however, that the chemopreventive activities of the compounds found in green tea are sensitive to the source and manufacturing and storage techniques. Thus, it is preferred that standardized and well-characterized tea extracts be used in the practice of the present invention.

Mixed Carotenoids

Chemical structures for various carotenoids are shown in FIG. 7. The preferred form of the mixed carotenoids is as follows:

Form: Carotenoids

CAS Names (9CI): See FIG. 7.

Carotenoids represent a class of hydrocarbons and their oxygenated derivatives (reviewed in [29]). Structurally, carotenoids consist of eight isoprenoid units joined so that their arrangement is reversed at the center of the molecule. In general, carotenoids available in a normal human diet are extremely hydrophobic molecules that form aggregates or adhere nonspecifically to structural surfaces. In vivo, free (i.e., not aggregated) carotenoids are restricted to hydrophobic environments. FIG. 7 summarizes the structures of some important carotenoids.

Epidemiological studies have shown that cancer risk is inversely related to the consumption of fruits and vegetables. Carotenoids are natural pigments synthesized by plants and microorganisms that are thought to function as light absorbing pigments during photosynthesis and to protect cells from photosensitization [178]. Diets rich in carotenoid containing foods have been associated with a number of human health benefits including cancer risk reduction [179–182]. Carotenoids are hydrophobic molecules containing an extensive series of conjugated double bonds [183, 184] and based on their hydrophobicity are mostly associated with lipids and membranes.

It is the unique structure and hydrophobicity of carotenoids that form the basis for their biological antioxidant activity as scavengers of ROS. The chemical structure of carotenoids provides multiple sites for interaction with free radicals and ROS [185–191]. Analysis of human serum and breast milk has identified more than 20 dietary carotenoids from fruits and vegetables that may be absorbed and metabolized by humans [192]. The chemical diversity of carotenoids optimizes the reactivity, uptake and tissue distribution of these compounds in biological systems.

Carotenoids have demonstrated biological activities in addition to maintaining oxidative balance. Experimental evidence demonstrates that carotenoids modulate cytochrome P-450 metabolism [193], inhibit arachidonic acid metabolism [185], modulate the immune system [193–195] and induce differentiation and/or gap junction intercellular communication [196–199].

Most epidemiological studies evaluating the effects of carotenoids and cancer risk have focused on β-carotene and lycopene. Carotenoid intake is associated with cancer risk reduction at multiple sites. The most consistent data have been obtained evaluating the effects of carotenoid intake and reduction of lung cancer risk [200–202]. In addition, carotenoid intake has been associate with a reduced risk for cancer of the stomach [203–206], colon and rectum [206, 207], pancreas [208] and prostate [209, 210] in addition to other organ sites [211, 212]. These data are most compelling for prostate, lung and stomach cancer risk reduction [213].

Carotenoid structure strongly affects the physical properties,. chemical reactivity and biologic functions of these compounds. It has been suggested that the size, shape, hydrophobicity and polarity of individual carotenoids may dramatically affect the bioavailability, absorption, circulation, tissue and subcellular distribution and excretion in mammals [214–217]. A mixture of carotenoids provides the maximum broad-spectrum opportunity to control carcinogenesis at all stages.

Regarding pharmacology and toxicology, the bioavailability of β-carotene has been extensively studied, but much less is known about other carotenoids including lycopene. Following oral intake, carotenoids are solubilized by the bile acids present in the intestine and dissolved into lipid droplets within the stomach and duodenum [214, 215]. Evidence suggests that carotenoid transport in plasma is exclusively via lipoproteins [215, 248]. Thus, dietary lipids may play an important role in carotenoid dissolution and subsequent absorption [249–252]. In addition, decreases in lipid absorption due to either disease processes or drug interactions may also inhibit uptake. Carotenoids are not well absorbed (25–75%) and are found unchanged in the feces [253]. Carotenoids as a group have very low toxicity [41, 254].

EXAMPLE 2

Colorectal Health Formulations of the Invention

In another aspect, the invention utilizes evidence from the three screening tiers described herein to achieve a balance of multiple nutrients designed to treat specific forms of disease, such as particular cancers. As an example, one nutrient formulation of the invention useful in colorectal cancer risk reduction comprises seven active components as described in more detail below, which were identified specifically for colorectal health conditions using the tiered screening method of the invention. Such colorectal health formulations are designed to promote optimum colorectal health by minimizing alterations to genetic material (often involved in initiation) and to minimize the effects of inflammatory processes associated with modified cell proliferation, apoptosis and/or angiogenesis, often involved in later stages of tumor development (promotion and progression). As with other nutrient formulations of the invention, such colorectal health formulations have been developed for specific risk and "normal" populations, and dosages reflect the general needs of these groups.

Colorectal cancer is the fourth most common cancer in the world and it ranks second in terms of cancer deaths in the United States [257]. The incidence of colorectal cancer is similar for men and women except in high-incidence areas where rates for men exceed women by 20%. In addition, the incidence of rectal cancer is 1.5–2 times as likely in men as in women. Although the epidemiology is somewhat different for colon and rectal cancer, data suggest that dietary risk factors are similar [258].

Colorectal cancer incidence rates vary 20-fold across different regions and populations around the world [256]. Colorectal cancer incidence is lowest in India, Africa (all regions), South Eastern Asia, Melanesia, Micronesia/Polynesia, Eastern Asia (including China), Central America and the Tropical region of South America [258]. Epidemiologic evidence indicates that the incidence of colorectal cancer is generally increasing in developed countries and in urban areas of developing countries [258]. The observation that the patterns of colorectal cancer are sensitive to human migration [259, 260] and urbanization indicates that the incidence of colorectal cancer is strongly affected by environmental factors including diet. In fact, it has been estimated that 70–90% of colorectal cancer deaths can be linked to diet [261]. It is generally agreed that colorectal cancer risk can be significantly modified by food and nutrition [258].

There are multiple molecular pathways involved in the development of colorectal cancer and significant scientific efforts are focused on elucidating the interplay between environmental exposures and host susceptibilities and the development of the disease [256]. The molecular pathway to colorectal cancer is tightly coupled to the unique microarchitecture of the colon. Crypts that are approximately 50 cells deep characterize the colon and it is these colonic crypt epithelial cells that are involved in the initiation of colon carcinogenesis. Colorectal cancer begins when crypt epithelial cells accumulate genetic alterations that impact the control of cell growth and differentiation. As a result of these genetic changes, benign adenomatous polyps can arise in the colonic epithelium and if left undetected, some of these may transform into adenocarcinomas. On average this transformation process appears to take 10–15 years.

Molecular changes in the adenomatous polyposis coli (APC)-β-catenin-T-cell factor (Tcf) pathway and the DNA mismatch repair pathway have been associated with both inherited and sporadic cancers. Changes in the expression of key genes in these pathways can be the result of inherited or acquired mutations or the result of DNA hypermethylation.

Familial adenomatous polyposis (FAP) and hereditary nonpolyposis colorectal cancer (HNPCC) represent at least two familial syndromes that predispose individuals to colorectal cancer. Inherited mutations in DNA mismatch repair genes and the APC gene are responsible for the increased colorectal cancer incidence in these individuals [262]. Colorectal cancer expression occurs 15–20 years earlier in those with either syndrome compared to unaffected individuals [263]. Although these familial syndromes are rare and account for 2–3% of colorectal cancer cases, the molecular mechanisms involved in carcinogenesis are similar to those observed in sporadic adenocarcinomas. These similarities have enabled investigators to identify environmental factors including diet that may influence the carcinogenic processes associated with these genetic alterations [256].

Risk factors for colorectal cancer include a positive family history for the disease and environmental exposures such as smoking, alcohol and diets high in red meat. Although inconclusive, there is some evidence to suggest that iron intake may also be linked to increased colorectal cancer risk. Overall, epidemiologic and other evidence indicates that diets high in vegetables and regular physical exercise decrease the risk of colorectal cancer. Risk of developing colorectal cancer is also affected by several non-dietary factors including, genetic predisposition, ulcerative colitis, infection with *Schistosoma sinensis* and smoking tobacco [258].

The observation that consumption of heavily cooked meats containing high levels of heterocyclic amines (potential carcinogens) is associated with increased risk for colorectal cancer lead to the hypothesis that polymorphisms in the enzymes that metabolize heterocyclic amines may influence an individual's risk [264, 265]. The three relevant enzymes being investigated are N-acetyltransferases, NAT1 and NAT2, and the cytochrome P450 enzyme $CYP_{1A2}$. Experimental evidence suggests that molecular differences in the genes for these enzymes may modulate an individual's risk for colorectal cancer when combined with specific dietary patterns [256].

Folate is important for methyl group metabolism and may influence both DNA methylation and the available nucleotide pool for DNA replication and repair. Experimental studies suggest that adequate folate intake is associated with a reduced risk of colorectal cancer [266–269], which is consistent with epidemiological evidence supporting the association between vegetable intake and colorectal cancer risk reduction. Preliminary results suggest that polymorphisms of the enzyme methylenetetrahydrofolate reductase (MTHFR) may modulate the impact of folate on colorectal cancer risk [270]. Thus, evidence is growing to support the hypothesis that an individual's cancer risk is mediated by an interplay between diet and host response which can be mediated by genetic polymorphisms among genes involved in the metabolism of dietary components.

Analysis of dietary patterns and colorectal cancer incidence has been used to identify dietary factors that may influence both the development and prevention of this disease. As noted, meat consumption, smoking and alcohol consumption have been associated with an increased risk of colorectal cancer and vegetable consumption has been associated with a decreased risk [256, 433, 271]. In some regions of the world where colorectal cancer incidence is the lowest, for example in India [272], multiple dietary factors may contribute to the overall reduced risk such as a high intake of plant based foods coupled with a low intake of animal based foods.

Current knowledge continues to elucidate the interrelationships of food, nutrition and other factors and their effect throughout the various stages of the colorectal cancer process, from initiation through progression and metastasis [273]. Known dietary carcinogens, such as heterocyclic amines, polycyclic aromatic hydrocarbons and N-nitroso compounds may play a role in the earliest stages of the cancer development process by directly contributing to the body's carcinogen load. The quality of the diet may affect the extent to which such dietary carcinogens may initiate the cancer process. Diets high in vegetables provide a large number of bioactive compounds that induce detoxification enzymes and thus, plausibly reduce the body's DNA exposure to dietary carcinogens.

Epidemiologic studies have demonstrated a strong association between colorectal cancer risk and vegetable and fruit intake. Seventeen out of twenty one case-control studies found that the risk of colorectal cancer was reduced for individuals with a higher intake of vegetables and fruit [258, 274]. This observation has been particularly consistent for consumption of raw vegetables, green vegetables and cruciferous vegetables. In addition, a meta-analysis of six case-control studies found a 50% reduction in colorectal cancer incidence among individuals with the highest versus lowest consumption of vegetables [275].

In the intermediate stages of carcinogenesis, appropriate energy balance and normal cell turnover are critical to maintaining normal cell behavior versus allowing promotion of abnormal cells. Evidence suggests that obesity increases the risk of tumorigenesis. Hence, caloric intake and physical activity affect the likelihood of progression of carcinogenesis at this stage. DNA damage is again central to cancer development in the later stages of the process, where a number of dietary factors may play key roles in blocking progression of the disease. These include folate (central to appropriate DNA methylation patterns and to the integrity of the nucleotide pool), fiber (produces volatile fatty acids which may increase programmed cell death of abnormal cells); and antioxidants (reduces the generation of free radicals and reactive oxygen species (ROS) which further damage DNA).

Folate and vitamin $B_{12}$ are central to methyl group metabolism and may influence both DNA methylation and the available nucleotide pool for DNA replication and repair. There is a growing body of evidence that methylenetetrahydrofolate reductase (MTHFR) influences the association between low levels of folate and vitamin $B_{12}$ and the risk for colorectal cancer. Individuals with a specific MTHFR polymorphism, TT, and low levels of folate and vitamin $B_{12}$ appear to be at highest risk, but the risk is normalized with adequate intake of these vitamins [270, 276, 277].

Clinical and molecular investigations have identified multiple molecular pathways involved in colorectal carcinogenesis and preliminary results suggest that colorectal cancer risk may be modulated by a dynamic interplay between host susceptibility and dietary patterns. The risk reduction approach of the present invention has been to focus on providing an optimal formulation of components that effectively compensates for an individual's molecular risk factors and dietary intake.

The key micronutrients associated with lower colorectal cancer incidence have been determined using the screening methods of the present invention to include folate, fiber and antioxidants. Evidence from mechanistic and other studies suggest that calcium and vitamin D may also be effective in stopping and/or slowing colorectal cancer development. By integrating bidirectional data such as these—top-down from epidemiological studies and bottom-up from mechanistic studies—the present inventors have ascertained the improved colorectal cancer risk reduction formulations of the present invention. The selection of key ingredients is based on epidemiologic studies of dietary patterns, analysis of the specific dietary components, identification of mechanistic opportunities for intervention in colorectal cancer progression, and evidence from clinical, animal and in vitro studies. The colorectal cancer risk reduction product as exemplified below is formulated to provide balanced, synergistic and rational dietary supplementation that is designed to intervene at various stages and interrupt specific mechanisms of carcinogenesis.

The colorectal cancer risk reduction product is designed to provide both systemic and luminal exposure to selected compounds to optimize opportunities for intervention. Specifically, the ingredients include the following range of possible intervention targets: reducing the risk of genetic damage, via support of appropriate methylation of DNA and the integrity of the nucleotide pool; maintaining antioxidant/oxidant balance of the cell environment; directly blocking formation of ROS, thus decreasing the opportunity for inappropriate cell proliferation, secondary genetic hits, and generation and progression of dysplastic tissue formation; directly intervening in the cyclooxygenase pathway; and reducing and/or removing promoting chemicals from the cell environment.

Based on application of the three-tiered screening method of the present invention, the preferred colorectal health formulation of the invention includes six principal dietary ingredients and a natural anti-inflammatory agent. The components of the preferred colorectal cancer risk reduction product and their key mechanistic roles in the carcinogenic process include the following:

Salicin-Salicin's major role is as a cyclooxygenase inhibitor (both COX-1, constitutive form, and COX-2, inducible form), the enzyme responsible for biosynthesis of prostaglandins. This natural form of salicylic acid intervenes in prostaglandin synthesis pathways and cellular inflammatory processes that are clearly shown to be up-regulated in colon cancer cells. Salicin has been shown to modulate cell proliferation, apoptosis and angiogenesis, which often are involved in the later stages of tumor development (promotion and progression).

Curcumin-Curcumin, discussed above, has been shown to exhibit both anti-oxidant and anti-inflammatory activity (COX inhibition). Evidence also shows that curcumin stimulates cell differentiation and apoptosis, and its activity has been demonstrated in both the initiation and progression stages of the colorectal carcinogenesis.

Calcium-Calcium directly acts to reduce cell proliferation and reduce the potential promoting effects of bile acids and free fatty acids by conversion of these into insoluble calcium soaps in the large intestine.

Vitamin D-Vitamin D primarily enhances the absorption of calcium. In addition, evidence suggests that vitamin D: inhibits cell proliferation, DNA synthesis, induction of orthnithine decarboxylase (ODC), lipid peroxidation and angiogenesis; induces cell differentiation in colorectal cancer cells, TGF-β and possibly apoptosis; modulates signal transduction by calcium and protein kinase C; and alters the expression of various oncogenes.

Folic Acid-Folic acid is involved in the pathways necessary for normal methylation of DNA and the maintenance of the nucleotide pool, thus reducing the likelihood of uracil incorporation and maintaining DNA integrity.

Vitamin $B_6$-Vitamin $B_6$ is a cofactor in the conversion of methionine to cysteine and is involved in methylation pathways necessary for normal DNA formation, maintenance and repair.

Vitamin $B_{12}$-This B vitamin is a cofactor for methionine synthase and ultimately for the production of S-adenosyl-methionine, the key source of methyl groups.

Table 2 below summarizes a preferred formulation of one colorectal cancer risk reduction product of the invention. It is preferred that the product be taken as six tablets per day in two divided doses, morning and evening with food. Dosage levels and timing of doses are recommended to maximize synergy among the individual components and provide more constant physiological availability of the components. It is preferred that natural forms of the specific vitamins, phytochemicals and other active components described herein be used to obtain maximal efficacy in the formulations of the invention, although synthetic versions, isomers, and mixtures of synthetic and natural components and related compounds may be employed.

The colorectal health product as detailed below is intended as a general formulation for use by individuals having an elevated risk of colorectal cancer. As with other formulations discussed herein, dosages will typically be customized according to other risk factors or profile factors such as gender, history of smoking, etc. Furthermore, it will be apparent given the present disclosure that dosages can readily be adjusted upward or downward for subjects having abnormally high or low body weight or extremes of diet.

TABLE 2

Colorectal Product Composition - Recommended Dose.

| Compound (and preferred source form) | Component Ranges (Relative) | Daily Dose |
| --- | --- | --- |
| Salicin (as white willow bark extract, standardized to 15% salicin) | 20–200 mg | 120 mg |
| Curcumin (as 95% curcuminoid extract) | 5–50 mg | 10 mg |
| Calcium, elemental (as carbonate salt) | 200–2500 mg | 800 mg |
| Vitamin D (as Vitamin $D_3$) | 100–1000 IU | 400 IU |
| Folic Acid | 200–2000 mcg | 800 mcg |
| Vitamin $B_6$ (Pyridoxine HCl) | 0.5–10 mg | 2 mg |
| Vitamin $B_{12}$ (Cyanocobalamin) | 0.1–100 mcg | 6 mcg |

Abbreviations: IU, international unit; mcg, micrograms

It is preferred that the daily dosages of the specified components be within about ±20% of the amounts specified above, and more preferably within about ±10% of the amounts specified above. Such tolerance ranges for each of the separate components may be specified individually and need not all be the same.

The colorectal cancer formulation exemplified above was identified by the present inventors using the three-tiered screening method described above. The application of that method in the context of the exemplified antioxidant formulation will now be described in more detail.

Salicin

Salicin is the glucoside of salicyl alcohol. The chemical structure of salicin is shown in FIG. 8. The preferred form of salicin is as follows:

Form: White Willow Bark Extract standardized to 15% salicin

Chemical Name: 2-(Hydroxymethyl)phenyl-β-D-glucopyranoside

Other Names: salicoside; salicyl alcohol glucoside; saligenin-β-D-glucopyranoside Chemical Formula: $C_{13}H_{18}O_7$
Molecular Weight: 286.28
Source: Usually obtained by making hot water extracts from the ground bark of poplar (Populus) and willow (Salix); also found in the leaves and female flowers of the willow.

The history of non-steroidal anti-inflammatory drugs (NSAIDs) can be traced to ancient Egypt, where an extract of willow bark was used to treat inflammation [278, 279]. Throughout history, extracts of the bark and roots of several species of willow have been used to relieve pain, fight fever and treat gout. The active component of the extract was subsequently identified as the glucoside of salicyl alcohol. During the nineteenth century, salicin was first isolated from numerous species of Salix (e.g., S. alba, S. helix, S. pentandra, S. paraecox) [280]. The main commercial sources today are S. fragilis and S. purpurea which are native to Europe and/or Asia [280]. Hydrolysis of the carbohydrate moiety of salicin produces salicyl alcohol, which can be oxidized to salicylic acid, the actual anti-inflammatory agent [281].

Sodium salicylate was first used for treating rheumatic fever and as an antipyretic in 1875; its use as a uricosuric soon followed. Based on its success, acetylsalicylic acid (aspirin) was synthesized and first introduced in 1899, and soon displaced the more expensive compounds obtained from natural sources. Subsequently, a host of new agents, chemically heterogeneous but sharing anti-inflammatory, antipyretic and analgesic activity as well as side effects, have entered the marketplace and are frequently referred to as nonsteroidal anti-inflammatory drugs or NSAIDs. Salicin, therefore, represents a naturally occurring NSAID.

Epidemiologic studies have consistently identified an association between the consumption of NSAIDs, including aspirin and a decreased risk of colorectal cancer. Seven case-control and three cohort studies reported lower risks of colorectal cancer associated with aspirin intake [282–291] compared to one cohort study and one low-dose aspirin intervention study that showed no association between aspirin intake and colorectal cancer [292–294]. In addition, regular aspirin use has been associated with a decrease in the occurrence of adenomatous polyps [282, 284, 290, 295, 296]. Evidence indicates that NSAIDs may also be effective in reducing the risk of colorectal cancer in individuals with FAP [297] and HNPCC [298]. Studies of cancer occurrence in patients with rheumatoid arthritis in Finland [299, 300] and Sweden [301], motivated by a concern that NSAIDs might increase the risk of gastric cancer, did not demonstrate this to be the case. In fact, the incidence of colorectal cancer was reduced among individuals with rheumatoid arthritis presumably due to the intake of NSAIDs [301].

Backing up the human studies is an extensive literature on the inhibition of colorectal cancer by NSAIDs in rodent model systems [302–312].

NSAIDs are currently understood to function primarily through a reduction in prostaglandin synthesis by inhibiting the enzyme prostaglandin endoperoxide synthase. This polypeptide enzyme contains both cyclooxygenase and peroxidase activities and occurs as two isoforms which are referred to as cyclooxygenase (COX-1 and COX-2) [313]. COX catalyzes the biosynthesis of prostaglandins and thromboxanes, which are bioactive lipids that play a role in a broad range of physiological and pathophysiological processes. NSAIDs act by tightly binding the active site of the cyclooxygenase, preventing combination of the enzyme with arachidonic acid [314–316].

There is strong evidence that inhibition of COX (especially COX-2) contributes to the ability of NSAIDs to inhibit the development of colorectal cancer, however the mechanisms by which COX expression contributes to tumorigenesis are unclear. Prostaglandins and thromboxane, the products of arachidonic acid oxygenation via the cyclooxygenase pathway, have diverse biological effects, including stimulation of cell proliferation, suppression of the immune response and alteration of haemodynamic properties [317]. Each prostaglandin and thromboxane has a specific transmembrane, G-protein linked receptor coupled to an intracellular signaling pathway. Thus, there are multiple mechanisms by which the products formed from COX could enhance the growth of transformed colonic epithelial cells. For example, prostaglandin E2 has been associated with the promotion and spread of cancerous cells, the formation of ROS and suppression of the immune system and NSAIDs have been shown to inhibit or prevent these activities. In addition, the inhibition of COX-2 activity [318] by NSAIDs has been associated with changes in epithelial proliferation, apoptosis and angiogenesis [319, 320].

Salicin, as an extract of white willow bark, is generally absorbed more slowly than aspirin and some of the other NSAIDs, and typically has a longer duration of action in the body. It is thought to have fewer adverse effects, especially gastrointestinal upset, than aspirin. However, due to its COX-1 inhibitory activity, it also has the potential to cause gastrointestinal ulceration. It is typically taken in doses of 60 to 120 mg per day.

Salicin is included in the present colorectal risk reduction formulation based on the significant epidemiologic and animal evidence for an association between NSAID intake and colorectal cancer risk reduction combined with favorable bioavailability and decreased gastrointestinal complications.

Regarding pharmacology, the actions relevant to intervention via salicylates and NSAIDs in the colorectal cancer process are as follows:

Anti-Inflammatory—
    Reversible, competitive inhibition of cyclooxygenase-2 implicated in colorectal carcinogenesis
    Induces changes in nitric oxide production
Other Mechanisms—
    Induction of apoptosis (colon tumor cells, including cell lines that do not express COX or make prostaglandins)

Upon ingestion, the carbohydrate moiety of salicin is cleaved, producing salicyl alcohol, which is then oxidized to salicylic acid, the actual anti-inflammatory agent, in the stomach [281]. Orally ingested salicylates are absorbed rapidly, partly from the stomach but mostly from the upper small intestine. Significant plasma concentrations are found within 30 minutes and peak plasma concentrations are reached within about 2 hours and gradually decline [281]. Salicylic acid absorption occurs by passive diffusion across gastrointestinal membranes and is therefore influenced by pH. Salicylate is 80% to 90% bound to plasma proteins, especially albumin and competes with a variety of compounds for plasma protein binding sites.

Biotransformation of salicylate takes place in many tissues, but especially in the hepatic endoplasmic reticulum and mitochondria. The three primary metabolic products are salicyluric acid, the ether or phenolic glucuronide and the ester or acyl glucuronide. Salicylates are excreted in the urine as free salicylic acid (10%), salicyluric acid (75%), salicylic phenolic (10%) and acyl (5%) glucuronides.

Regarding toxicology, toxicity for salicin is similar to that seen for aspirin and non-aspirin NSAIDs, but natural salicin is a safer form for human use. The more commonly observed side effects and toxicities of salicylates are primarily associated with inhibition of COX-1 and include [281]:

increased risk of gastrointestinal ulceration and bleeding
potential renal toxicity in the at-risk patient decreased aggregation of platelets leading to an increased risk for bleeding The only contraindication to ingestion of salicin is hypersensitivity to salicylates. Patients should be cautioned about the use of the present colorectal cancer risk reduction product in conjunction with the use of other salicylates and NSAIDs.

A daily dose of 120 mg salicin, taken in two divided doses, has been selected for the colorectal cancer risk reduction product. This dose was chosen based on the clinical data for aspirin that supports that colorectal cancer chemoprevention at a minimum dose of one-half aspirin tablet per day, and equating the salicin dose on an equimolar basis.

The use of low dose, long term administration of salicin as a colorectal cancer chemopreventive is supported by strong epidemiological studies as well as animal and in vitro mechanistic cell data for aspirin and other NSAIDs [321]. Salicin, as a dietary supplement, is currently marketed as a natural product for arthritis and pain management. Hence, the inclusion of salicin in the colorectal cancer risk reduction product is unique and provides intervention in the colorectal cancer process possibly via both COX-2 dependent and independent pathways.

Curcumin

The chemical structure of curcumin is shown in FIG. 5. The preferred form of curcumin is discussed above, as are other features of this nutrient ingredient. Additional aspects of this ingredient are described below.

The initial rationale for investigating curcumin as a chemopreventive agent for colorectal cancer arose from the observation that India has one of the lowest incidences of colorectal cancer in the world [272] and one of the highest intakes of dietary curcumin. Dietary intake of curcumin among Indians has been estimated at 10–100 mg/day [26, 322]. The reduced risk of colorectal cancer observed among Indians may also be associated with multiple dietary factors including a high intake of plant based foods coupled with a low intake of animal based foods.

Animal studies have demonstrated that curcumin consumption is associated with the inhibition of tumorigenesis at several organ sites [26, 113, 114]. Using colon carcinogenesis as an example, curcumin has demonstrated chemopreventive activity in all three stages of carcinogenesis [115]. Curcumin has been shown to inhibit chemically induced carcinogenesis in the skin, forestomach and colon when it was administered during initiation and/or post-initiation stages [26, 116–119]. Curcumin suppressed the incidence and multiplicity of noninvasive adenocarcinomas, as well as the multiplicity of invasive adenocarcinomas of the colon, when administered during the promotion/progression phase [115]. Thus, administration of curcumin prior to, during and after carcinogen treatment as well as during the promotion/progression phases of colon carcinogenesis resulted in significant risk reduction [115].

As noted previously, curcumin has been shown to exhibit a wide range of biological activities including both anti-inflammatory [108, 109] and antioxidant properties [111]. Curcumin is the major antioxidant substance in turmeric. Curcumin protects cells against $H_2O_2$-induced oxidative stress [121]. Curcumin has been shown to scavenge reactive oxygen species such as the hydroxyl radical [122–126], superoxide [126] and singlet oxygen [128]. Curcumin also interferes with lipid peroxidation [122, 129–137] and nitrite/nitrogen oxide production [138, 139]. Curcumin is also an inhibitor of neutrophil response and of superoxide generation in macrophages [140].

In addition to antioxidant properties, curcumin exhibits a diverse array of metabolic, cellular and molecular activities including inhibition of arachidonic acid formation and its further metabolism to eicosanoids [118, 141–143]. Evidence also suggests that curcumin acts on pathways that may inhibit cell proliferation [144] and enhance apoptosis [145]. Curcumin inhibits several mediators and enzymes involved in cell mitogenic signal transduction pathways [146] and activator protein-1 and nuclear factor κB activation [148–149]. Curcumin has also been associated with the modulation of COX-2 enzyme levels and specific activity in a variety of cell types [117, 118, 323].

Curcumin is included in the present colorectal risk reduction formulation based on lack of toxicity, efficacy in inhibiting tumorigenesis in several animal models, its multiple mechanisms of action and its occurrence in the diets of individuals with low incidence of colorectal cancer.

Regarding pharmacology, curcumin has demonstrated a wide range of pharmacological properties throughout different stages of tumor development in a broad range of biological systems. In vitro studies have identified the following metabolic, cellular and molecular activities associated with the anticarcinogenic activity of curcumin:

Modulation of Phase I and Phase II enzymes

Antioxidant activity

Inhibition of arachidonic acid metabolism

Modulation of cellular signal transduction pathways

Inhibition of hormone and growth factor activity

Inhibition of oncogene activity

Curcumin exhibits a diverse array of metabolic, cellular and molecular activities, including inhibition of arachidonic acid formation and its further metabolism to eicosanoids [118, 141]. Evidence also suggests that curcumin acts on pathways that may inhibit cell proliferation [144] and enhance apoptosis [145]. Curcumin inhibits several mediators and enzymes involved in cell mitogenic signal transduction pathways [146] and activator protein-I and nuclear factor κB activation [148, 149, 147].

Early preclinical pharmacokinetics studies suggested that curcumin was poorly absorbed from the gastrointestinal tract. Subsequent studies with radiolabeled pigment showed that 60% of an oral dose was absorbed and appeared to be transported by the bile, metabolized and conjugated, and re-excreted into the gut. The primary route of excretion is via the feces.

Regarding toxicology, curcumin is presumed to be safe due to a long history of human use in Asia up to an estimated 95 mg/day as the food additive turmeric (3.8 g/day). Human studies investigating curcumin in rheumatoid arthritis or AIDS patients have reported that doses up to approximately 2000 mg four times a day for 18 weeks were tolerated without adverse effects [324, 325]. See also the discussion above regarding curcumin in connection with the oxidative balance formulations of the invention.

Based on the screening method of the present invention, curcumin is included in the present colorectal cancer risk reduction formulation based on its wide array of potential chemopreventive activities (anti-inflammatory, antioxidant, promotion of cell differentiation and apoptosis, etc.). Its anti-inflammatory activity is attributed to COX inhibition and, as such, is expected to be synergistic with salicin in the formulation. Hence, this allows daily administration of lower doses of each component, thereby reducing the potential for adverse effects, particularly gastrointestinal. The 10 mg per day dose selected for the present colorectal cancer risk reduction product is less than doses that are under consideration in initial clinical chemopreventive trials by the NCI (25 mg and upwards), but are deemed to be appropriate for chronic administration.

Calcium

The preferred for calcium for use in the present colorectal cancer product is as follows:

Form: Calcium carbonate

Molecular Weight: 40.08

Elemental calcium is available as a number of different salts for administration as a dietary supplement, as well as natural sources, such as oyster shell formulations. The calcium carbonate from is preferred for use in the present colorectal cancer risk reduction product for a number of reasons. First, evidence suggests that the salt form does not have a significant impact on the absorption characteristics of calcium, but apparently certain physical attributes of manufacturing that affect tablet disintegration and dosage form dissolution do have an effect. Scientific evidence indicates that it is desirable for some of the orally administered calcium to not be absorbed, but rather to be available locally in the large bowel to form insoluble complexes of calcium soaps with bile acids as a chemopreventive strategy for colorectal cancer [351, 361]. Such physical specifications will ensure maximum balance between bioavailability and topical delivery of calcium to the large bowel.

Second, the carbonate salt form of calcium provides the greatest concentration of elemental calcium in the least weight and bulk. This is important with regard to the number of dosage units and their practical size required for incorporating the selected daily dose of elemental calcium. Third, calcium carbonate, in addition to serving as the elemental calcium source, also functions as an antacid. The antacid feature is desirable in that it provides some protection against stomach irritation that could be associated with salicin in the formulation.

Epidemiological studies suggest that calcium may be an important chemoprotective in colorectal cancer. Cohort and case-control studies investigating calcium intake and colorectal cancer have provided evidence of either an inverse or null association [326]. Eight cohort studies examined calcium intake and colorectal cancer incidence [327–334]. Although only one of sixteen estimates of relative risk was statistically significantly less than 1.0, there was clear trend towards an inverse relationship between calcium intake and colorectal cancer risk. Fifteen case-control studies have also examined the relationship between calcium intake and colorectal cancer [330, 335–348]. Of the twenty-five odds ratios presented in these studies, six showed statistically significant reductions in risk, one showed a statistically significant increase and eighteen were null. A meta-analysis of twenty-four studies estimated a summary relative risk of 0.89 (0.79–1.01) for an inverse relationship between calcium intake and the risk of colorectal cancer [349]. In addition, a recent clinical study demonstrated that calcium supplementation was associated with a moderate but statistically significant reduction in the recurrence of colorectal adenomas [350].

It has been hypothesized that calcium may reduce colorectal cancer risk by normalizing crypt cell proliferation and kinetics. Abnormal cellular proliferation and differentiation of cells in the colonic epithelium has been associated with an increased susceptibility of colorectal cancer and has been observed in individuals with pervious familial and nonfamilial colon cancers, familial polyposis, sporadic adenomas and ulcerative colitis. Several studies have investigated whether calcium supplementation can attenuate hyperproliferation in individuals at increased risk for colorectal cancer. These studies have shown that calcium supplementation is associated with significant decreases in cellular proliferation and/or normalization of the distribution of proliferating cells within the colonic epithelium [351–354]. In addition, increases in dietary calcium, via increased consumption of low-fat dairy foods, were also associated with reductions in colonic cellular proliferation and normalization of additional biomarkers for cellular differentiation [355].

Similarly, animal and in vitro mechanistic studies have added to the body of evidence that increased calcium intake has a role in reducing the incidence of colorectal cancer. Animal studies, specifically, have demonstrated a beneficial effect of calcium on colonic epithelial cell proliferation [356–362].

Initially, calcium was thought to lower colorectal cancer through the formation of insoluble calcium soaps with free bile acids and unabsorbed fatty acids that are irritating and mitogenic to the colorectal epithelium [326, 358]. Subsequently, calcium salts have also been shown to modify biochemistry of differentiation- and proliferation-related activity in colon cancer cells [354].

Because of the physiological co-dependence between calcium and vitamin D in maintaining calcium homeostasis, some of the chemoprotective actions of calcium may also be attributable to vitamin D. However, further research regarding potential chemopreventive mechanisms now suggests that each of these supplements may have independent chemopreventive activities related to modulation of cellular proliferation and differentiation.

Calcium is included in the present colorectal risk reduction formulation based on human data demonstrating a consistent trend for colorectal cancer risk reduction associated with dietary and supplemental calcium intake and on human, animal and in vitro studies demonstrating an association between calcium and normalization of colonic epithelial cell proliferation.

Regarding pharmacology, $Ca^{2+}$ is the major extracellular divalent cation. Men and women have a total body load of approximately 1300 g and 1000 g of $Ca^{2+}$, respectively, of which more than 99% is in bone. $Ca^{2+}$ in intracellular fluids is present in its ionized state at about 0.1 $\mu M$ under basal conditions. In response to hormonal, electrical or mechanical stimuli, temporary increase in $Ca^{2+}$ flux raises the concentration toward 1 $\mu M$, permitting interactions with specific $Ca^{2+}$-binding proteins that activate numerous processes. Additionally, $Ca^{2+}$ serves as a second messenger for the actions of many hormones.

In human plasma, calcium circulates at a concentration of about 8.5 to 10.4 mg/dl, of which approximately 45% is bound to plasma proteins (primarily albumin) and about 10% is complexed to anionic buffers [363]. The remaining $Ca^{2+}$ fraction exerts the mineral's physiological effects. Regulation of extracellular calcium is under tight endocrine control that affects its entry via the intestine and its exit via the kidney that, in turn, regulates the large skeletal reserve.

In the U.S., about 75% of dietary calcium is obtained from milk and dairy products. $Ca^{2+}$ enters the body only through the intestine. Active vitamin D-dependent transport occurs in the proximal duodenum and facilitated diffusion takes place throughout the small intestine. There is a daily obligatory loss of calcium of about 150 mg/day associated with mucosal and biliary secretions and sloughed intestinal cells.

Calcium absorption is inversely related to calcium intake—a diet low in calcium leads to a compensatory increase in absorption related, in part, to activation of vitamin D [363]. This response, however, decreases with age. Urinary excretion of $Ca^{2+}$ is the net result of the quantity filtered and amount reabsorbed (approximately 98%), the latter of which is tightly regulated by parathyroid hormone.

Regarding toxicilogy, absorption of large quantities of $Ca^{2+}$ salt does not generally, by itself, cause hypercalcemia except in cases of hypothyroidism, in which $Ca^{2+}$ is absorbed with increased efficiency, and milk-alkali syndrome, in which concurrent ingestion of milk and alkalinizing powders results in impaired renal $Ca^{2+}$ excretion. Other causes of hypercalcemia are associated with various disease states, including primary hyperparathyroidism, familial benign hypercalcemia, systemic malignancy, and vitamin D excess.

The usual daily dose of elemental calcium used in cancer chemoprevention clinical trials has ranged from 1,250 to 2,000 mg per day. The inventors have identified a preferred daily supplement dose of elemental calcium of 800 mg per day, taking into consideration the scientific evidence and practical aspects of the consumer including dietary intake and product acceptability:

Supplement doses exceeding 800 mg per day are generally not well tolerated by individuals due to side effects associated with the gastrointestinal tract (distress, bloating, etc.).

Vitamin D is included in the present colorectal cancer risk reduction product for two primary reasons—its inherent chemoprevention activities and its role in enhancing calcium absorption and utilization. Due to the synergy in calcium effectiveness gained by its co-administration with vitamin D combined with the scientific literature, it is preferred in the practice of the invention to use 800 mg per day as an appropriate daily dose to reduce colorectal cancer risk.

Given natural dietary consumption, 800 mg is recommended for long term administration to achieve a daily target dose of 1250 mg.

Vitamin $D_3$

The chemical structure of vitamin $D_3$ is shown in FIG. 9. The preferred form of vitamin $D_3$ is as follows:

Form: Ergocalciferol

CAS Name (9CI): (3β,5Z,7E)-9,10-Secocholesta-5,7,10 (19)-triene-3-ol

Molecular Weight: 384.62

Vitamin D is the name applied to two related fat-soluble substances, cholecalciferol (vitamin $D_2$) and ergocalciferol (vitamin $D_3$). In humans, there is no practical difference between the two forms [363]. The present colorectal product preferably utilizes vitamin $D_3$, but vitamin $D_2$ or mixtures of the two forms may be used in the alternative.

The original idea that vitamin D may protect against colorectal cancer is based on observations from ecologic studies that support an inverse association between the level of solar radiation and colorectal cancer mortality and incidence [364–366]. These studies demonstrated that colorectal cancer incidence and mortality were highest in the areas of the US and elsewhere in the world that received the least amount of sunlight. Since most of the vitamin D in humans (up to 80%) is derived through sunlight-induced photobiosynthesis in the skin, it was hypothesized that vitamin D levels may modulate colorectal cancer risk.

In general, human studies have observed an inverse association between vitamin D intake and colorectal cancer incidence but most associations are not statistically significant. Of the six cohort studies investigating the association between vitamin D intake and colorectal cancer, one study demonstrated a statistically significant inverse association for colorectal cancer [333] while four additional studies demonstrated inverse associations that were not statistically significant [331, 367–369]. One study found no association between vitmain D intake and colorectal cancer [328].

Vitamin D was consistently associated with colorectal cancer risk reduction in a series of case-control studies. Seven out of ten studies found an inverse association for either vitamin D intake [370–373] or serum levels of vitamin D metabolites [374–376] and the incidence of adenomas or colorectal cancer. High levels of vitamin D intake from diet and/or supplements and increased serum levels of vitamin D metabolites were associated with lower incidence of colorectal cancer [370, 372–376] and adenomas [371]. These inverse associations were statistically significant among five of the seven studies evaluated [371, 372, 374–376]. The three remaining studies found that vitamin D intake was not associated with colorectal cancer incidence [345–377] or development of adenomas [378].

Human, animal and in vitro experimental results indicate that vitamin D and its metabolites may protect against colorectal cancer by reducing epithelial cell proliferation [379–382] and inducing differentiation [383, 384]. Vitamin D, as 1,25-dihydroxyvitamin $D_3$, regulates epithelial cell growth and differentiation and may be an important determinant of progression towards terminal differentiation [385]. These associations may be due to a direct effect of vitamin D through vitamin D receptors or an indirect effect by increasing calcium absorption. Experimental studies have demonstrated that vitamin D receptors are expressed in cultured human colon cancer cell lines and colorectal cancer tissue [386, 387].

Research in rodents has shown a chemopreventive role for vitamin D related to reduced proliferation of colonic epithelial cells [356, 388]. In vitro studies with human colon cell lines have also demonstrated vitamin D's effectiveness in reducing cell proliferation and DNA synthesis [389–392], modulation of signal transduction by calcium and protein kinase C, modulation of c-myc, c-fos, and c-jun oncogene expression [393–397], lipid peroxidation [398] and angiogenesis [399] and induction of differentiation [382, 400–402], TGF-β expression [403] and, possibly, apoptosis [404].

Vitamin D is included in the present colorectal risk reduction formulation based on human evidence for a modest effect on colorectal risk reduction and on mechanistic studies demonstrating an inhibition of cellular proliferation and an induction of cellular differentiation. The roles of calcium and vitamin D are closely linked because calcium bioavailability is tightly coupled to adequate vitamin D levels. Synergistic activity between vitamin D and calcium (discussed above) has been shown with vitamin D as a facilitator for the expression of a chemopreventive function of calcium. Additionally, evidence suggests that calcium and vitamin D exert chemopreventive roles in colorectal carcinogenesis through different pathways.

A key differentiating point in the present colorectal cancer risk reduction product is providing a balanced intake of calcium and vitamin D, thereby achieving maximum colorectal cancer chemoprevention. Large excesses of either supplement can be counterproductive to colorectal cancer risk reduction.

Regarding pharmacology, vitamin D requires activation to become biologically active. The primary active metabolite is calcitriol (1,25-dihydroxyvitamin D), the product of two successive hydroxylations of vitamin D. The initial hydroxylation (25-hydroxylation, 25-OHD) is achieved by an hepatic enzyme system associated with the microsomal and mitochondrial fractions and requires NADPH and molecular oxygen. After production in the liver, 25-OHD enters the circulation where it is carried by vitamin D-binding globulin. Final activation to calcitriol occurs primarily in the kidney by a mixed function oxidase enzyme system associated with mitochondria in the proximal tubules that requires NADPH and oxygen as cofactors. This latter conversion is subject to tight control of systems associated with maintaining optimal calcium homeostasis.

Vitamin D, once thought to have a passive role in calcium metabolism, is now recognized as a hormone that, together with parathyroid hormone, is a major positive regulator of the concentration of $Ca^{2+}$ in plasma. Important in the cancer process, vitamin D binds to specific receptors in target tissues, resulting in an increased concentration of plasma $Ca^{2+}$. Additionally, the vitamin D receptors mediate a variety of actions that are unrelated to $Ca^{2+}$ homeostasis.

Receptors for calcitriol are widely distributed throughout the body. Among the effects of vitamin D beyond calcium homeostasis maintenance are:

Influence on maturation and differentiation of mononuclear cells and cytokine production Other effects on the immune system Inhibition of proliferation and induction of differentiation of malignant cells Inhibition of epidermal proliferation and promotion of epidermal differentiation More specifically, among vitamin D's activities that are thought to be relevant to intervention in the colorectal cancer process include the inhibition of: cell proliferation; DNA synthesis; ornithine decarboxylase induction; lipid peroxidation; and angiogenesis [389–392, 398, 399]. In addition, vitamin D plays a role in inducing the differentiation of certain cancer cells (human leukemia, human prostate, skin, breast and colon cancers), TGF-β expression and possibly apoptosis; and modulates signal transduction by calcium and protein kinase C and c-myc, c-fos and c-jun oncogene expression.

Intestinal absorption of vitamin D is generally adequate under most conditions. Both vitamins $D_2$ and $D_3$ are absorbed from the small intestine, although evidence suggests that vitamin $D_3$ absorption is more efficient. Following absorption, vitamin D appears first within chylomicrons in lymph.

Bile, particularly deoxycholic acid, is essential for adequate absorption of vitamin D. Absorbed vitamin D circulates in the blood in association with vitamin D-binding protein, a specific α-globulin. The half-life from disappearance from the plasma is 19 to 25 hours from which it is then stored in fat depots for prolonged periods.

Regarding toxicology, the amount of vitamin D necessary to cause hypervitaminosis varies widely among individuals. In general, continuous ingestion of 50,000 units or more daily by an individual with normal parathyroid function and vitamin D sensitivity will begin to exhibit signs of hypervitaminosis including: hypercalcemia, weight loss and tissue calcification and some evidence for embryo toxicity and teratogenicity [363].

The RDA for vitamin D is 400 IU, and is the preferred daily dosage selected for inclusion in the present colorectal cancer risk reduction product.

Calcitriol's utility as a dietary supplement chemopreventive for colorectal cancer is limited by its hypercalcemic effects. The possibility of dissociating its actions on cell differentiation from its hypercalcemic effects has stimulated the search for analogs that might be useful in cancer chemoprevention and treatment, the results of which appear to be encouraging. Until such time as vitamin D analogs can make it through the traditional drug regulatory model for use as potential chemopreventives (a 10-plus year process), supplementation with 400 IU of vitamin D as in the present colorectal cancer risk reduction product is safe, rational and scientifically supported by the literature. Beyond its own inherent chemopreventive activities listed above, vitamin D's inclusion in the colorectal risk reduction product provides synergy with calcium, thereby enhancing the absorption of this mineral and its own inherent chemopreventive role in this disease. Supplementation of dietary and natural sources of vitamin D is further supported as synthesis of vitamin D secondary to exposure to ultraviolet radiation has decreased with the increased use of sunscreens and greater avoidance of sun exposure. Additionally, there is evidence that the absorption and effectiveness of vitamin D diminishes as people age.

Folic Acid

The chemical structure of folic acid is shown in FIG. 10 The preferred form of folic acid is as follows:

Form: pteroylglutamic acid, the common pharmaceutical form of folic acid

CAS Name (9CI): N-[4-[[**(2-Amino-1,4-dihydro-4-oxo-6-pteridinyl)methyl]amino]benzoyl]-L-glutamic Acid Molecular Weight: 441.40

Pteroylglutamic acid is the common pharmaceutical form of folic acid, a water-soluble B complex vitamin, which can be absorbed unchanged in the small intestine. The principal folate congeners in food are generally polyglutamates from which all but one glutamate residue must be removed by intestinal conjugases prior to absorption. The major portions of the folate molecule include a pteridine ring linked by a methylene bridge to paraaminobenzoic acid, which is joined by an amide linkage to glutamic acid [430].

Folic acid is one of the nutrients found in vegetables that has been hypothesized to contribute to the reduced risk of colorectal cancer associated with high vegetable intake [433, 266]. Folate is an essential dietary component involved in maintaining the availability of methyl groups important for the normal synthesis and metabolism of amino acids, nucleotides and lipids. It is also a cofactor in the production of S-adenosylmethionine (SAM), the primary methyl donor in the body. Folate deficiencies may impact cancer risk by altering DNA methylation or by affecting the available nucleotide pool important for DNA replication and repair [405, 406].

The specific role of folates in DNA replication results in preservation of the methylation pattern of newly synthesized DNA strands. DNA methylation is important for modulating gene expression and failure to maintain the methylation pattern in nascent DNA may either facilitate the aberrant expression of oncogenes [407–409] or inhibit the expression of tumor suppressor genes, thereby contributing to cancer progression.

Alterations in DNA methylation patterns are common in colorectal cancer and are clearly related to genetic instability [410–412]. Scientific evidence now links DNA hypomethylation as an early event in colon cancer [413, 414] and has been shown to increase during the histopathologic progression of the disease [415, 416]. One study has demonstrated that rectal mucosa tissue from patients with colon cancer is globally hypomethylated compared with tissue from controls, and that folic acid supplementation significantly reduces hypomethylation [413]. Since hypomethylation may be initiated by inadequate cellular levels of SAM [417], and production of SAM is dependent on both methionine and folate, dietary patterns that provide inadequate levels of these factors may contribute to imbalances in DNA methylation and hence an increased risk of colorectal cancer.

Folate is also important for maintenance of deoxynucleotide pools involved in DNA synthesis. Because folate is required for the conversion of deoxyuridylate to thymidylate, depletion of folate has been associated with increased accumulation of deoxyuridylate in DNA. Removal of this abnormal base may be associated with chromosome breaks commonly observed in colorectal cancer.

Several lines of epidemiologic evidence suggest that folate and methyl group metabolism are associated with the risk of colorectal cancer. To date, the inventors have identified 22 human studies investigating associations between folate and the risk of colorectal cancer [266–270, 276, 277, 346, 370, 377, 418–429]. Among ten of these studies, colorectal cancer risk was associated with dietary and supplemental folate intake (e.g., increased risk was associated with low levels of folate intake and colorectal cancer risk was reduced among individuals with high levels of folate intake) [266–268, 346, 370, 377, 418, 421, 425, 426]. Additional studies have examined the association between specific dietary patterns and colorectal cancer risk. Alcohol modulates folate availability by decreasing its absorption, altering its metabolism and increasing its excretion. Thus, diets low in folate, particularly in combination with substantial alcohol intake are associated with increased risks of colorectal cancer [267, 276, 277, 424, 427, 429]. Preliminary evidence suggests that folate from multivitamin supplements may be more strongly associated with risk reduction [418]. The stronger association observed in these studies may be related to the enhanced bioavailability of folate from dietary supplements vs. food sources. In addition, the risk reduction associated with folate intake is also supported by studies that demonstrate an association between high serum/plasma levels of folate and reduced colorectal cancer incidence [276, 422, 423, 427].

Patients with chronic ulcerative colitis are at an increased risk for developing colorectal cancer compared with the general public. These patients commonly have decreased folate levels due to impaired folate absorption caused by medications used for disease management. In these patients, folate supplementation was associated with a 62% lower incidence of colon cancer compared to individuals not receiving supplementation [420].

Although several studies have demonstrated an association between colorectal cancer risk and folate status, four studies did not identify an association between folate intake or folate status and colorectal cancer risk [269, 276, 420] or recurrence of large bowel adenomas [419]. Variable associations between folate status and cancer risk may be the result of an individual's ability to regulate methyl group metabolism. Recently, several genetic polymorphisms in gene products important for methyl group metabolism have been investigated for their contribution to colorectal cancer risk. These studies have demonstrated that polymorphisms that contribute to changes in methyl group availability when combined with low folate intake and/or high alcohol intake are associated with significant increases in colorectal cancer risk [270, 276, 277, 429].

Based on the three-tiered screening method of the present invention as applied to empirical evidence, together with a suspected biological role for methyl donors in the cancer development process, folate is included in the present colorectal risk reduction formulation.

Regarding pharmacology, folic acid, in conjunction with vitamin $B_{12}$, is an essential dietary element. A deficiency in either vitamin results in defective DNA synthesis in any cell in which chromosomal replication and division are taking place. Hence, tissues with the greatest rate of cell turnover (e.g., hematopoetic system epithelium including colon, rectum, etc.) are subject to the most dramatic impact from a deficiency. Vitamin $B_6$ is also a necessary cofactor in the folate metabolic pathway [431]. Folic acid is important for the conversion of homocysteine to methionine and the synthesis of purine nucleotides. More specifically, as a chemopreventive, folic acid is responsible for:

Maintenance of the methylation pattern of nascent DNA

Reversal/prevention of DNA hypomethylation

Pyrimidine and purine synthesis

More recent research has shown that neither vitamin $B_{12}$ nor folic acid as purified from foodstuffs is the active coenzyme for human beings [430]. During extraction procedures, the active, labile forms are converted to stable congeners of vitamin $B_{12}$ and folic acid—cyanocobalamin and pteroylglutamic acid, respectively. These congeners must then be modified in vivo to be effective. The function of these vitamins as cofactors is an ongoing area of investigation.

Following absorption, pteroylglutamic acid is rapidly reduced at the 5, 6, 7 and 8 positions to tetrahydrofolic acid, which then acts as an acceptor of a number of one-carbon units which are attached at either the 5 or 10 position of the pteridine ring or may bridge these atoms to form a new five-membered ring [430]. The most important forms of folate include methyltetrahydrofolate, folinic acid, 10-formyltetrahydrofolate, 5,10-methenyltetrahydrofolate, 5,10-methylenetetrahydrofolate, formiminotetrahydrofolate and hydroxymethyltetrahydrofolate, each of which plays a specific role in intracellular metabolism.

Folates present in food are primarily reduced polyglutamates. Most folate absorption occurs in the proximal portion of the small intestine. Absorption requires transport and pteroyl-γ-glutamyl carboxypeptidase associated with mucosal cell membranes. The mucosa in the duodenum and upper jejunum are rich in dihydrofolate reductase and are capable of methylating the reduced folate that is absorbed. Once absorbed, folate is rapidly transported to tissues as methyltetrahydrofolate. Certain plasma proteins will bind folate derivatives, but generally have a greater affinity for the non-methylated analogs [430]. The role of such binding proteins in folate homeostasis remains unclear, although increased binding capacity is noted in folate deficiency.

A constant supply of methyltetrahydrofolate is maintained by food and by enterohepatic cycling of the vitamin. The liver actively reduces and methylates pteroylglutamic acid and then transports methyltetrahydrofolate into bile for reabsorption by the gut and subsequent delivery to tissues. Up to 200 μg or more of folic acid may be provided for recirculation to tissues. Following uptake of methyltetrahydrofolate into cells, it acts as a methyl donor for the formation of methylcobalamin and as a source of tetrahydrofolic acid and other folate congeners.

Regarding toxicology, folic acid is generally considered to be non-toxic in humans. No adverse human effects were seen with 10 mg/d for 4 months or 15 mg/d (duration not stated). A few cases of allergic reactions to folate have been noted. Folic acid has the potential to mask vitamin $B_{12}$ deficiency that, if left untreated, can have significant untoward consequences. In very high doses (>20 mg/d), folic acid may cause convulsions in persons whose epilepsy is in continuous control by phenytoin, phenobarbital or primidone [432]. Additionally, high doses of folic acid for long periods may interfere with zinc absorption.

Food sources rich in folates include fresh green vegetables, liver, yeast and some fruits. Up to 90% of folate can be destroyed by lengthy cooking. The standard U.S. diet typically provides 50 to 500 μg of absorbable folate per day; with high fresh vegetable and meat intake, this can approach 2 mg per day. The minimal daily adult requirement is 50 μg, whereas pregnant or lactating women or individuals with high cell rate turnover require 100 to 200 μg per day.

Clinical trials of folic acid as a cancer chemopreventive have been conducted at daily doses ranging from less that 1 mg up to 10 mg. There is some evidence that folic acid, in excess of the daily maintenance requirement, may function physiologically in other pathways or processes that enhance its role as a chemopreventive. The present formulation preferably provides a daily dose of 800 μg (400 μg administered twice daily) as the rational supplemental dose for long term cancer risk reduction, based on current scientific evidence.

Vitamin $B_6$

The chemical structures of vitamin $B_6$, which includes three forms, are shown in FIG. 12. The preferred form of vitamin $B_6$ is as follows:

Form: Pyridoxine HCl
Chemical Name: Vitamin $B_6$ (as pyridoxine HCl)
Molecular Weight: 205.64 (as HCl salt)

The three forms of vitamin $B_6$ (pyridoxine, pyridoxal and pyridoxamine) differ in the nature of the substituent on the carbon atom in position 4 of the pyridine nucleus: a primary alcohol group (pyridoxine), the corresponding aldehyde (pyridoxal), an aminoethyl group (pyridoxamine). Each of the compounds can be utilized readily by mammals following conversion to pyridoxal 5' phosphate, the active form of the vitamin, in the liver [431]. Pyridoxine is the preferred form of vitamin $B_6$ for use in the present invention, but the other forms of the vitamin may be used additionally or in the alternative.

Vitamin $B_6$ is an important cofactor in a variety of metabolic transformations of amino acids, including decarboxylation, transamination and racemization, as well as in enzymatic steps in the metabolism of sulfur-containing and hydroxy-amino acids. Vitamin $B_6$ is one of several dietary components important for optimization of cellular folate metabolism involved in colorectal cancer risk reduction. Vitamin $B_6$ is a cofactor in the conversion of methionine to cysteine and is involved in methylation pathways necessary for normal DNA formation, maintenance and repair.

Human epidemiologic studies have suggested that vitamin $B_6$ intake may be related to colorectal cancer risk. These studies have found that increased intake of vitamin $B_6$ is associated with decreased risk for colorectal cancer [269, 347] and colorectal polyps [341]. In a study investigating the association between colon cancer risk and specific MTHFR polymorphisms (an enzyme important in folate metabolism) found that high intakes of vitamin $B_6$ were associated with decreased risk of colon cancer [429].

The inclusion of vitamin $B_6$ in the present colorectal cancer risk reduction product is to optimize availability of this important dietary factor to support its role in metabolic folate pathways involved in DNA methylation, synthesis, maintenance and repair. Support for the role of folate in colorectal cancer risk reduction is discussed above.

Regarding pharmacology, as a coenzyme, pyridoxal phosphate is involved in several metabolic transformations of amino acids, including decarboxylation, transamination and racemization, as well as in enzymatic steps in the metabolism of sulfur-containing and hydroxy-amino acids. Particularly relevant to its synergistic role in the colorectal cancer product is its activity as a cofactor in the conversion of methionine to cysteine [430].

Vitamin $B_6$ is supplied by meat, liver, whole-grain breads and cereals, soybeans and vegetables. However, substantial losses occur during cooking as well as ultraviolet light exposure and oxidation.

The three different forms of vitamin $B_6$ are readily absorbed from the gastrointestinal tract following hydrolysis of their phosphorylated derivatives. Pyridoxal phosphate accounts for at least 60% of circulating vitamin $B_6$. Pyridoxal is thought to be the primary form that crosses cell membranes. 4-pyridoxic acid is the principal form excreted in humans, formed by the action of hepatic aldehyde oxidase on free pyridoxal.

Vitamin $B_6$ has low acute toxicity and elicits no outstanding pharmacodynamic actions after oral administration. Neurotoxicity may develop after prolonged ingestion of 200 mg of vitamin $B_6$ per day, and symptoms of dependency have been noted in adults given 200 mg daily.

The requirement for vitamin $B_6$ increases with the amount of protein in the diet. The average adult minimal requirement for vitamin $B_6$ is 1.5 mg per day in individuals ingesting 100 g of protein on a daily basis. To allow for a reasonable margin of safety and for protein intake in excess of 100 g, the RDA of vitamin $B_6$ for men is 2.0 mg and for women is 1.6 mg. Due to its wide margin of safety, the inventors have identified a preferred daily dose of 2.0 mg for inclusion in the colorectal cancer risk reduction product to ensure sufficient availability of vitamin $B_6$.

Vitamin $B_{12}$

The chemical structure of vitamin $B_{12}$ is shown in FIG. 13. The preferred form of vitamin $B_{12}$ is as follows:

Form: Cyanocobalamin
Chemical Name: Vitamin $B_{12}$
Molecular Weight: 1355.38

There are three major portions to the molecule:

A planar group or corrin nucleus—a porphyrin-like ring structure with four reduced pyrrole rings linked to the center cobalt atom and extensively substituted with methyl, acetamide and proprionamide residues.

A 5,6-dimethyulbenzimidazolyl nucleotide, which links at nearly right angles to the corrin nucleus with bonds to the cobalt atom and to the propionate side chain of the fourth pyrrole ring.

A variable R group—the most important of which are found in the stable compounds, cyanocobalamin and hydroxocobalamin, and the active coenzymes, methylcobalamin and 5-deoxyadenosylcobalamin [430].

The terms, vitamin $B_{12}$ and cyanocobalamin, are used interchangeably for all of the cobamides active in humans. Dietary supplements use either cyanocobalamin or hydroxocobalamin since they remain stable and active during storage [430].

Vitamin $B_{12}$ is a cofactor for methionine synthase, an enzyme important for maintaining adequate levels of intracellular methionine and folate. Deficiencies in either $B_{12}$ or folate can lead to decreased synthesis of methionine and SAM and can interfere with protein and polyamine biosynthesis. In addition, deficiencies can lead to a modification of folate metabolic pathways to promote methylation reactions at the expense of nucleic acid synthesis, which can lead to imbalances in deoxynucleotide pools. Nucleotide imbalance can lead to accumulation of deoxyuridylate in DNA and is associated with DNA strand breaks commonly seen in colorectal cancers.

The inclusion of vitamin $B_{12}$ in the present colorectal cancer risk reduction product is to ensure adequate availability of this cofactor to optimize folate metabolism and methyl group availability. Support for the role of folate in colorectal cancer risk reduction is discussed above.

Regarding pharmacology, intracellular vitamin $B_{12}$ is maintained as two active coenzymes, methylcobalamin and deoxyadenosylcobalamin (deoxyadenosyl $B_{12}$). It is methylcobalamin that supports the methionine synthase reaction, which is essential for normal metabolism of folate [430]. Methyl groups contributed by methyltetrahydrofolate are used to form methylcobalamin, which then acts as a methyl group donor for the conversion of homocysteine to methionine. This folate-cobalamin interaction is pivotal for normal synthesis of purines and pyrimidines and, therefore, of DNA. The methionine synthase reaction is largely responsible for the control of the recycling of folate cofactors, the maintenance of intracellular concentrations of folylpolyglutamates and, through the synthesis of methionine and its product, S-adenosylmethionine, the maintenance of a number of methylation reactions.

Humans are dependent upon exogenous sources of vitamin $B_{12}$. Primary sources in nature include certain microorganisms that grow in soil, sewage, water or in the intestinal lumen of animals and that synthesize the vitamin. Vegetables are free of vitamin $B_{12}$ unless they are contaminated with such microorganisms. The daily nutritional requirement of 3 to 5 $\mu g$ must be obtained from animal byproducts. Additionally, a certain amount of vitamin $B_{12}$ is available from legumes that are contaminated with vitamin $B_{12}$-producing bacteria.

Dietary vitamin $B_{12}$ is released from salivary binding protein in the presence of gastric acid and pancreatic proteases. It is subsequently immediately bound to intrinsic factor, a glycoprotein. The vitamin $B_{12}$-intrinsic factor complex then reaches the ileum where it interacts with a specific receptor on ileal mucosal cells and is transported to the circulation. Hence, vitamin $B_{12}$ deficiency is generally the result of a defect in some aspect of the gastrointestinal tract necessary for its absorption to occur.

Once absorbed, vitamin $B_{12}$ binds to transcobalamin II, a plasma $\beta$-globulin, for transport to tissues. This complex is rapidly cleared from the plasma and is preferentially distributed to hepatic parenchymal cells. As much as 90% of the body's stores of vitamin $B_{12}$, from 1 to 10 mg, is in the liver, where it is stored as the active coenzyme with a turnover rate of 0.5 to 8 $\mu g$ per day, depending on the size of the body's stores.

Approximately 3 $\mu g$ of cobalamins are secreted into the bile each day, 50% to 60% of which represents cobalamin analogs that are not reabsorbed. Interference with the 40% to 50% reabsorption via the enterohepatic cycle can result in depletion of the hepatic store.

Regarding toxicology, no toxicity or safety issues were noted for vitamin $B_{12}$.

The present colorectal cancer risk reduction product preferably includes 6 $\mu g$ of vitamin $B_{12}$. The rationale for its inclusion relates to its synergistic role as a cofactor in the folate pathway and the scientific evidence for the role of folic acid as a colorectal cancer chemopreventive [256, 430, 432]. Additionally, since the primary dietary source of vitamin $B_{12}$ is animal byproducts and/or microorganism "contamination" of vegetables, vegetarians are at risk for deficiency of this vitamin. Its presence in the formulation, therefore, ensures adequate availability of vitamin $B_{12}$ to ensure the effectiveness of folic acid in methylation reactions.

Inclusion of vitamin $B_{12}$ in the present colorectal cancer risk reduction product is based upon its key role as a cofactor for folic acid in the body. Its presence, therefore is synergistic with folic acid, and thereby ensures that folic acid can be available for maximal chemopreventive activities.

FORM OF FINAL PRODUCTS FOR ADMINISTRATION

As explained above, the final form of the present nutrient formulations may take a variety of forms, such as pills, capsules, tablets, liquids, powders, etc. Such forms are particularly suited for oral administration, and it is within the skill of the art given the present disclosure to arrive as suitable forms for such final products. The formulations may also be designed for topical application to the skin or mucous membranes where appropriate, as for example for administration to rectal mucous membrane tissue. Preparation of such topical products is likewise within the skill in the art given the present disclosure. It will be recognized, for example, that inactive ingredients such as solid or liquid carriers (include aqueous, organic or lipid-based carriers), diluents, excipients, sustained-release materials or matrices, penetration enhancing agents, delivery vehicles such as liposomal structures, and other similar ingredients may usefully be incorporated into the final products in order to facilitate the desired mode of administration. Examples of such materials, and others that may be incorporated into the final products, are discussed in detail in, for example, standard texts such as Martin (ed.), *Remington's Pharmaceutical Sciences, Martindale—The Extra Pharmacopoeia* (Pharmaceutical Press, London 1993), and others.

The foregoing description and examples are not intended to limit the scope of the present invention, which is set forth in the appended claims. In addition, various equivalents will be recognized by those skilled in the art in view of the foregoing disclosure, and all such equivalents are contemplated to be within the lawful scope of the invention.

APPENDIX—REFERENCES CITED

1. World Cancer Research Fund (WCRF), *Food, Nutrition and the Prevention of Cancer: a Global Perspective*. 1997, Menasha: American Institute for Cancer Research. 426.
2. Steinmetz, K. A. and J. D. Potter, *Vegetables, fruit, and cancer prevention: a review*. J Am Diet Assoc, 1996. 96(10): p. 1027–39.
3. Hercberg, S., et al., *Background and rationale behind the SU.VI.MAX Study, a prevention trial using nutritional doses of a combination of antioxidant vitamins and minerals to reduce cardiovascular diseases and cancers. SUpplementation en VItamines et Mineraux AntioXydants Study*. Int J Vitam Nutr Res, 1998. 68(1): p. 3–20.
4. *Free radicals, lipidperoxidation and cancer*, ed. D. C. H. McBrien and T. F. Slater. 1982, London: Academic Press.
5. Block, G., B. Patterson, and A. Subar, *Fruit, vegetables, and cancer prevention: a review of the epidemiological evidence*. Nutr Cancer, 1992. 18(1): p. 1–29.
6. Byers, T. and N. Guerrero, *Epidemiologic evidence for vitamin C and vitamin E in cancer prevention*. Am J Clin Nutr, 1995. 62(6 Suppl): p. 1385S–1392S.
7. van Poppel, G. and R. A. Goldbohm, *Epidemiologic evidence for beta-carotene and cancer prevention*. Am J Clin Nutr, 1995. 62(6 Suppl): p. 1393S–1402S.
8. Block, G., *Vitamin C and cancer prevention: the epidemiologic evidence* [see comments]. Am J Clin Nutr, 1991. 53(1 Suppl): p. 270S–282S.

9. Greenwald, P., *NCI Cancer prevention and control research*. Preventive Med, 1993. 22: p. 642–660.
10. Nowell, P. C., *The clonal evolution of tumor cell populations*. Science, 1976. 194(4260): p. 23–8.
11. Weinstein, I. B., et al., *Molecular mechanisms of mutagenesis and multistage carcinogenesis*, in *The Molecular Basis of Cancer*, J. Mendelsohn, et al., Editors. 1995, W. B. Saunders: Philadelphia. p. 59–85.
12. Foulds, L., *Neoplastic Development*. 1969, New York: Academic Press.
13. Anzano, M. A., et al., *Prevention of breast cancer in the rat with 9-cis-retinoic acid as a single agent and in combination with tamoxifen*. Cancer Res, 1994. 54(17): p. 4614–7.
14. Anzano, M. A., et al., *Chemoprevention of mammary carcinogenesis in the rat: combined use of raloxifene and 9-cis-retinoic acid*. J Natl Cancer Inst, 1996. 88(2): p. 123–5.
15. Ratko, T. A., et al., *Chemopreventive efficacy of combined retinoid and tamoxifen treatment following surgical excision of a primary mammary cancer in female rats*. Cancer Res, 1989. 49(16): p. 4472–6.
16. Moon, R. C., et al., *Chemoprevention of MNU-induced mammary tumors in the mature rat by 4-HPR and tamoxifen*. Anticancer Res, 1992. 12(4): p. 1147–53.
17. Lucia, M. S., et al., *Chemopreventive activity of tamoxifen, N-(4-hydroxyphenyl)retinamide, and the vitamin D analogue Ro24-5531 for androgen-promoted carcinomas of the rat seminal vesicle and prostate*. Cancer Res, 1995. 55(23): p. 5621–7.
18. Reddy, B. S., et al., *Chemoprevention of colon carcinogenesis by concurrent administration of piroxicam, a nonsteroidal antiinflammatory drug with D,L-alpha-difluoromethylornithine, an ornithine decarboxylase inhibitor, in diet*. Cancer Res, 1990. 50(9): p. 2562–8.
19. Kelloff, G. J., et al., *Mechanistic considerations in chemopreventive drug development*. J Cell Biochem Suppl, 1994.20: p. 1–24.
20. Kelloff, G. J., et al., *Inhibition of chemical carcinogenesis*, in *Chemical Induction of Cancer. Modulation and Combination Effects*, J. C. Arcos, M. F. Argus, and Y. Woo, Editors. 1995, Birkhauser: Boston. p. 73–122.
21. Prasad, K. N., W. Cole, and P. Hovland, *Cancer prevention studies: past, present, and future directions*. Nutrition, 1998. 14(2): p. 197–210; discussion 237–8.
22. *Free Radicals in Biology and Medicine*. 2nd ed, ed. B. Halliwell and J. M. C. Gutteridge. 1989, Oxford, UK: Clarendon Press.
23. McCord, J. M., *Human disease, free radicals, and the oxidant/antioxidant balance*. Clin Biochem, 1993. 26(5): p. 351–7.
24. McCord, J., *The Importance of Oxidant-Antioxidant Balance*, in *Oxidative Stress, Cancer, AIDS, and Neurogenerative Diseases*, L. Montagnier, R. Olivier, and C. Pasquier, Editors. 1996, Marcel Dekker: New York. p. 1–6.
25. Jacob, R. A., *Vitamin C*, in *Modern Nutrition in Health and Disease*, M. E. Shils, J. A. Olson, and M. Shike, Editors. 1993, Lea and Febiger: Philadelphia. p. 432–48.
26. Huang, M. T., et al., *Inhibitory effects of dietary curcumin on forestomach, duodenal, and colon carcinogenesis in mice*. Cancer Res, 1994. 54(22): p. 5841–7.
27. Kuroda, Y. and Y. Hara, *Antimutagenic and anticarcinogenic activity of tea polyphenols*. Mutat Res, 1999. 436(1): p. 69–97.
28. Wang, Z. Y., et al., *Inhibitory effects of black tea, green tea, decaffeinated black tea, and decaffeinated green tea on ultraviolet B light-induced skin carcinogenesis in 7,12-dimethylbenz[a]anthracene-initiated SKH-1 mice*. Cancer Res, 1994. 54(13): p. 3428–35.
29. Organization, W. H. and I.A.f.R.o. Cancer, *Carotenoids*. IARC Handbooks of Cancer Prevention. Vol. 2. 1998, Lyon, France: International Agency for Research on Cancer. 326.
30. Bjomeboe, A., G. E. Bjorneboe, and C. A. Drevon, *Absorption, transport and distribution of vitamin E*. J Nutr, 1990. 120(3): p. 233–42.
31. Machlin, L. J. and A. Bendich, *Free radical tissue damage: protective role of antioxidant nutrients*. Faseb J, 1987. 1(6): p.441–5.
32. Tappel, A. L., *Vitamin E and selenium protection from in vivo lipid peroxidation*. Ann N Y Acad Sci, 1980. 355: p. 18–31.
33. Ames, B. N., *Dietary carcinogens and anticarcinogens. Oxygen radicals and degenerative diseases*. Science, 1983. 221(4617): p. 1256–64.
34. Knekt, P., *Role of vitamin E in the prophylaxis of cancer*. Ann Med, 1991. 23(1): p. 3–12.
35. Blot, W. J., et al., *Nutrition intervention trials in Linxian, China: supplementation with specific vitamin/mineral combinations, cancer incidence, and disease-specific mortality in the general population [see comments]*. J Natl Cancer Inst, 1993. 85(18): p. 1483–92.
36. Bostick, R. M., et al., *Reduced risk of colon cancer with high intake of vitamin E: the Iowa Women's Health Study*. Cancer Res, 1993. 53(18): p. 4230–7.
37. *The effect of vitamin E and beta carotene on the incidence of lung cancer and other cancers in male smokers. The Alpha-Tocopherol, Beta Carotene Cancer Prevention Study Group [see comments]*. N Engl J Med, 1994. 330(15): p. 1029–35.
38. Ohshima, H., J. C. Bereziat, and H. Bartsch, *Monitoring N-nitrosamino acids excreted in the urine and feces of rats as an index for endogenous nitrosation*. Carcinogenesis, 1982. 3(1): p. 115–20.
39. Hennekens, C. H., J. E. Buring, and R. Peto, *Antioxidant vitamins—benefits not yet proved [editorial; comment]*. N Engl J Med, 1994. 330(15): p. 1080–1.
40. Kelloff, G. J., et al., *Clinical development plan: vitamin E*. J Cell Biochem Suppl, 1994. 20: p. 282–99.
41. Cadenas, E. and L. Packer, *Handbook of antioxidants*. Antioxidants Health Dis, 1996. 3: p. 1–602.
42. Buettner, G. R., *The pecking order of free radicals and antioxidants: lipid peroxidation, alpha-tocopherol, and ascorbate*. Arch Biochem Biophys, 1993. 300(2): p. 535–43.
43. Niki, E., *Vitamin C as an antioxidant*. World Rev Nutr Diet, 1991. 64: p. 1–30.
44. Sharma, M. K. and G. R. Buettner, *Interaction of vitamin C and vitamin E during free radical stress in plasma: an ESR study*. Free Radic Biol Med, 1993. 14(6): p. 649–53.
45. Buettner, G. R. and B. A. Jurkiewicz, *Ascorbate free radical as a marker of oxidative stress: an EPR study*. Free Radic Biol Med, 1993. 14(1): p. 49–55.
46. Frei, B., et al., *Ascorbate: the most effective antioxidant in human blood plasma*, in *Antioxidants in therapy and preventive medicine*, I. Emerit and L. Packer, Editors. 1990, Plenum: New York.
47. Golumbic, C. and H. A. Mattill, *Antioxidants and the autoxidation of fats XIII: the antioxygenic action of ascorbic acid in association with tocopherols, hydroquinones, and related compounds*. J Am Chem Soc, 1941. 63: p. 1279–80.
48. Shamberger, R. J. and D. V. Frost, *Possible protective effect of selenium against human cancer*. Can Med Assoc J, 1969. 100(14): p. 682.

49. Shamberger, R. J. and C. E. Willis, *Selenium distribution and human cancer mortality.* CRC Crit Rev Clin Lab Sci, 1971. 2(2): p. 211–21.
50. Schrauzer, G. N., D. A. White, and C. J. Schneider, *Cancer mortality correlation studies—III: statistical associations with dietary selenium intakes.* Bioinorg Chem, 1977. 7(1): p. 23–31.
51. Yu, S. Y., et al., *Regional variation of cancer mortality incidence and its relation to selenium levels in China.* Biol Trace Elem Res, 1985. 7: p. 21–29.
52. Combs, G. F., Jr., *Selenium and cancer, in Antioxidants and Disease Prevention*, H. Garewal, Editor. 1997, CRC Press: New York. p. 97–113.
53. Clark, L. C., et al., *Plasma selenium concentration predicts the prevalence of colorectal adenomatous polyps.* Cancer Epidemiol Biomarkers Prev, 1993. 2(1): p. 41–6.
54. Salonen, J. T., et al., *Association between serum selenium and the risk of cancer.* Am J Epidemiol, 1984. 120(3): p. 342–9.
55. Willett, W. C., et al., *Prediagnostic serum selenium and risk of cancer.* Lancet, 1983. 2(8342): p. 130–4.
56. Helzlsouer, K. J., G. W. Comstock, and J. S. Morris, *Selenium, lycopene, alpha-tocopherol, beta-carotene, retinol, and subsequent bladder cancer.* Cancer Res, 1989. 49(21): p. 6144–8.
57. Kok, F. J., et al., *Is serum selenium a risk factor for cancer in men only?* [published erratum appears in Am J Epidemiol 1987 September; 126(3):559]. Am J Epidemiol, 1987. 125(1): p. 12–6.
58. van den Brandt, P. A., et al., *A prospective cohort study on toenail selenium levels and risk of gastrointestinal cancer.* J Natl Cancer Inst, 1993. 85(3): p. 224–9.
59. van den Brandt, P. A., et al., *A prospective cohort study on selenium status and the risk of lung cancer.* Cancer Res, 1993. 53(20): p. 4860–5.
60. Helzlsouer, K. J., et al., *Prospective study of serum micronutrients and ovarian cancer* [see comments]. J Natl Cancer Inst, 1996. 88(1): p. 32–7.
61. An, P., *Selenium and endemic cancer in China, in Environmental Bioinorganic Chemistry of Selenium*, P. M. Whanger, G. F. Combs, Jr., and J. Y. Yeh, Editors. 1995, Chinese Academy of Science: Beijing. p. 91–149.
62. Clark, L. C., et al., *Effects of selenium supplementation for cancer prevention in patients with carcinoma of the skin. A randomized controlled trial. Nutritional Prevention of Cancer Study Group* [see comments] [published erratum appears in JAMA 1997 May 21;277(19):1520]. Jama, 1996. 276(24): p. 1957–63.
63. Combs, G. F., Jr. and W. P. Gray, *Chemopreventive agents: selenium.* Pharmacol Ther, 1998. 79(3): p. 179–92.
64. Rotruck, J. T., et al., *Selenium: biochemical role as a component of glutathione peroxidase.* Science, 1973. 179 (73): p. 588–90.
65. Burk, R. F., *Molecular biology of selenium with implications for its metabolism.* Faseb J, 1991. 5(9): p. 2274–9.
66. Stadtman, T. C., *Selenocysteine.* Annu Rev Biochem, 1996. 65: p. 83–100.
67. Arthur, J. R. and G. J. Beckett, *New metabolic roles for selenium.* Proc Nutr Soc, 1994. 53(3): p. 615–24.
68. Sunde, R. A., *Molecular biology of selenoproteins.* Annu Rev Nutr, 1990. 10: p. 451–74.
69. Kohrle, J., *Thyroid hormone deiodination in target tissues—a regulatory role for the trace element selenium?* Exp Clin Endocrinol, 1994. 102(2): p. 63–89.
70. Taylor, E. W., *Selenium and cellular immunity. Evidence that selenoproteins may be encoded in the +1reading frame overlapping the human CD4, CD8, and HLA-DR genes.* Biol Trace Elem Res, 1995. 49(2–3): p. 85–95.
71. Roy, M., et al., *Supplementation with selenium restores age-related decline in immune cell function.* Proc Soc Exp Biol Med, 1995. 209(4): p. 369–75.
72. Shan, X. Q., T. Y. Aw, and D. P. Jones, *Glutathione-dependent protection against oxidative injury.* Pharmacol Ther, 1990. 47(1): p. 61–71.
73. Thomas, S. H., *Paracetamol (acetaminophen) poisoning.* Pharmacol Ther, 1993. 60(1): p. 91–120.
74. De Flora, S., et al., *Antioxidant activity and other mechanisms of thiols involved in chemoprevention of mutation and cancer.* Am J Med, 1991. 91(3C): p. 122S–130S.
75. De Flora, S., G. A. Rossi, and A. De Flora, *Metabolic, desmutagenic and anticarcinogenic effects of N-acetylcysteine.* Respiration, 1986. 50(Suppl 1): p. 43–9.
76. Izzotti, A., et al., *Inhibition by N-acetylcysteine of carcinogen-DNA adducts in the tracheal epithelium of rats exposed to cigarette smoke.* Carcinogenesis, 1995. 16(3): p. 669–72.
77. Cesarone, C. F., et al., *Differential assay and biological significance of poly(ADP-ribose) polymerase activity in isolated liver nuclei.* Mutat Res, 1990. 245(3): p. 157–63.
78. Albini, A., et al., *Inhibition of invasion, gelatinase activity, tumor take and metastasis of malignant cells by N-acetylcysteine.* Int J Cancer, 1995. 61(1): p. 121–9.
79. De Flora, S., et al., *Inhibition of urethan-induced lung tumors in mice by dietary N-acetylcysteine.* Cancer Lett, 1986. 32(3): p. 235–41.
80. Cesarone, C. F., et al., *Effects of aminothiols in 2-acetylaminofluorene-treated rats. I. Damage and repair of liver DNA, hyperplastic foci, and Zymbal gland tumors.* In Vivo, 1987. 1(2): p. 85–91.
81. Wilpart, M., A. Speder, and M. Roberfroid, *Anti-initiation activity of N-acetylcysteine in experimental colonic carcinogenesis.* Cancer Lett, 1986. 31(3): p. 319–24.
82. Reddy, B. S., et al., *Chemoprevention of colon carcinogenesis by organosulfur compounds.* Cancer Res, 1993. 53(15): p. 3493–8.
83. Cianfriglia, F., et al., [*The chemoprevention of oral carcinoma with vitamin A and/or N-acetylcysteine*]. Minerva Stomatol, 1994. 43(6): p. 255–61.
84. De Vries, N. and S. De Flora, *N-acetyl-l-cysteine.* J Cell Biochem Suppl, 1993: p. 270–7.
85. Issels, R. D., et al., *Promotion of cystine uptake and its utilization for glutathione biosynthesis induced by cysteamine and N-acetylcysteine.* Biochem Pharmacol, 1988. 37(5): p. 881–8.
86. De Flora, S., et al., *In vivo effects of N-acetylcysteine on glutathione metabolism and on the biotransformation of carcinogenic and/or mutagenic compounds.* Carcinogenesis, 1985. 6(12): p. 1735–45.
87. Nakata, K., et al., *Effects of age on levels of cysteine, glutathione and related enzyme activities in livers of mice and rats and an attempt to replenish hepatic glutathione level of mouse with cysteine derivatives.* Mech Ageing Dev, 1996. 90(3): p. 195–207.
88. Hoffer, E., et al., *N-acetylcysteine increases the glutathione content and protects rat alveolar type II cells against paraquat-induced cytotoxicity.* Toxicol Lett, 1996. 84(1): p. 7–12.
89. Corcoran, G. B. and B. K. Wong, *Role of glutathione in prevention of acetaminophen-induced hepatotoxicity by N-acetyl-L-cysteine in vivo: studies with N-acetyl-D-cysteine in mice.* J Pharnacol Exp Ther, 1986. 238(1): p. 54–61.

90. Cotgreave, I. A., et al., *No penetration of orally administered N-acetylcysteine into bronchoalveolar lavage fluid*. Eur J Respir Dis, 1987. 70(2): p. 73–7.
91. Bridgeman, M. M., et al., *Cysteine and glutathione concentrations in plasma and bronchoalveolar lavage fluid after treatment with N-acetylcysteine*. Thorax, 1991. 46(1): p. 39–42.
92. Burgunder, J. M., A. Varriale, and B. H. Lauterburg, *Effect of N-acetylcysteine on plasma cysteine and glutathione following paracetamol administration*. Eur J Clin Pharmacol, 1989. 36(2): p. 127–31.
93. Aruoma, O. I., et al., *The antioxidant action of N-acetylcysteine: its reaction with hydrogen peroxide, hydroxyl radical, superoxide, and hypochlorous acid*. Free Radic Biol Med, 1989. 6(6): p. 593–7.
94. Moldeus, P., I. A. Cotgreave, and M. Berggren, *Lung protection by a thiol-containing antioxidant: N-acetylcysteine*. Respiration, 1986. 50(Suppl 1): p. 31–42.
95. Wagner, P. D., et al., *Protection against pulmonary O2 toxicity by N-acetylcysteine*. Eur Respir J, 1989.2(2): p. 116–26.
96. Bonanomi, L. and A. Gazzaniga, *Toxicological, pharmacokinetic and metabolic studies on acetylcysteine*. Eur J Respir Dis Suppl, 1980. 111: p. 45–51.
97. Marui, N., et al., *Vascular cell adhesion molecule-1 (VCAM-1) gene transcription and expression are regulated through an antioxidant-sensitive mechanism in human vascular endothelial cells*. J Clin Invest, 1993. 92(4): p. 1866–74.
98. Weber, C., et al., *Antioxidants inhibit monocyte adhesion by suppressing nuclear factor-kappa B mobilization and induction of vascular cell adhesion molecule-1 in endothelial cells stimulated to generate radicals*. Arterioscler Thromb, 1994. 14(10): p. 1665–73.
99. Faruqi, R., C. de la Motte, and P. E. DiCorleto, *Alpha-tocopherol inhibits agonist-induced monocytic cell adhesion to cultured human endothelial cells*. J Clin Invest, 1994. 94(2): p. 592–600.
100. Ratan, R. R., T. H. Murphy, and J. M. Baraban, *Macromolecular synthesis inhibitors prevent oxidative stress-induced apoptosis in embryonic cortical neurons by shunting cysteine from protein synthesis to glutathione*. J Neurosci, 1994. 14(7): p. 4385–92.
101. Rothstein, J. D., et al., *Chronic inhibition of superoxide dismutase produces apoptotic death of spinal neurons*. Proc Natl Acad Sci USA, 1994. 91(10): p. 4155–9.
102. Talley, A. K., et al., *Tumor necrosis factor alpha-induced apoptosis in human neuronal cells: protection by the antioxidant N-acetylcysteine and the genes bcl-2 and crmA*. Mol Cell Biol, 1995. 15(5): p. 2359–66.
103. Abello, P. A., S. A. Fidler, and T. G. Buchman, *Thiol reducing agents modulate induced apoptosis in porcine endothelial cells*. Shock, 1994. 2(2): p. 79–83.
104. Zamzarni, N., et al., *Reduction in mitochondrial potential constitutes an early irreversible step of programmed lymphocyte death in vivo*. J Exp Med, 1995. 181(5): p. 1661–72.
105. Fang, W., et al., *Bcl-xL rescues WEHI 231 B lymphocytes from oxidant-mediated death following diverse apoptotic stimuli*. J Immunol, 1995. 155(1): p.66–75.
106. Miller, L. F. and B. H. Rumack, *Clinical safety of high oral doses of acetylcysteine*. Semin Oncol, 1983. 10(1 Suppl 1): p. 76–85.
107. Johnston, R. E., H. C. Hawkins, and J. H. Weikel, Jr., *The toxicity of N-acetylcysteine in laboratory animals*. Semin Oncol, 1983. 10(1 Suppl 1): p. 17–24.
108. Srimal, R. C. and B. N. Dhawan, *Pharmacology of diferuloyl methane (curcumin), a non-steroidal anti-inflammatory agent*. J Pharm Pharmacol, 1973. 25(6): p. 447–52.
109. Satoskar, R. R., S. J. Shah, and S. G. Shenoy, *Evaluation of anti-inflammatory property of curcumin (diferuloyl methane)in patients with postoperative inflammation*. Int J Clin Pharmacol Ther Toxicol, 1986. 24(12): p. 651–4.
110. Tonnesen, H. H., *Chemistry of curcumin and curcuminoids, in Phenolic Compounds in Food and their Effect of Health*, C.-T. Ho, C. Y. Lee, and M.-T. Haung, Editors. 1992, American Chemical Society: Washington, D.C. p. 143–153.
111. Sharma, O. P., *Antioxidant activity of curcumin and related compounds*. Biochem Pharmacol, 1976. 25(15): p. 1811–2.
112. Toda, S., et al., *Natural antioxidants. III. Antioxidative components isolated from rhizome of Curcuma longa L*. Chem Pharm Bull (Tokyo), 1985. 33(4): p. 1725–8.
113. Huang, M. T., et al., *Inhibitory effect of curcumin, chlorogenic acid, caffeic acid, and ferulic acid on tumor promotion in mouse skin by 12-O-tetradecanoylphorbol-13-acetate*. Cancer Res, 1988. 48(21): p. 5941–6.
114. Huang, M. T., et al., *Inhibitory effects of curcumin on tumor initiation by benzo[a]pyrene and 7,12-dimethylbenz[a]anthracene*. Carcinogenesis, 1992. 13(11): p. 2183–6.
115. Kawamori, T., et al., *Chemopreventive effect of curcumin, a naturally occurring anti-inflammatory agent, during the promotion/progression stages of colon cancer [In Process Citation]*. Cancer Res, 1999. 59(3): p. 597–601.
116. Huang, M. T., et al., *Effect of dietary curcumin and ascorbyl palmitate on azoxymethanol-induced colonic epithelial cell proliferation and focal areas of dysplasia*. Cancer Lett, 1992. 64(2): p. 117–21.
117. Rao, C. V., B. Simi, and B. S. Reddy, *Inhibition by dietary curcumin of azoxymethane-induced ornithine decarboxylase, tyrosine protein kinase, arachidonic acid metabolism and aberrant crypt foci formation in the rat colon*. Carcinogenesis, 1993. 14(11): p. 2219–25.
118. Rao, C. V., et al., *Chemoprevention of colon carcinogenesis by dietary curcumin, a naturally occurring plant phenolic compound*. Cancer Res, 1995. 55(2): p. 259–66.
119. Pereira, M. A., et al., *Effects of the phytochemicals, curcumin and quercetin, upon azoxymethane-induced colon cancer and 7,12-dimethylbenz[a]anthracene-induced mammary cancer in rats*. Carcinogenesis, 1996. 17(6): p. 1305–11.
120. Kanemaru, K., et al., *Protection of brain neurons suffering from oxidative stress by new curcuminoids isolated from Zingber sassumunar*. Natrual Sci Res, 1998. 11: p. 7–19.
121. Nagano, T., et al., *New curcuminoids isolated from Zingiber cassumunar protect cells suffering from oxidative stress: a flow-cytometric study using rat thymocytes and H2O2*. Jpn J Pharmacol, 1997. 75(4): p. 363–70.
122. Shih, C. A. and J. K. Lin, *Inhibition of 8-hydroxydeoxyguanosine formation by curcumin in mouse fibroblast cells*. Carcinogenesis, 1993. 14(4): p. 709–12.
123. Tonnesen, H. H. and J. V. Greenhill, *Studies on curcumin and curcuminoids. XXII: Curcumin as a reducing agent and as a radical scavenger*. Int J Pharmaceut, 1992. 87: p. 79–87.
124. Kunchandy, E., *Oxygen radical scavenging activity of curcumin*. Int J Pharmaceut, 1990. 58: p. 237–240.

125. Zhao, B. L., et al., *Scavenging effect of extracts of green tea and natural antioxidants on active oxygen radicals.* Cell Biophys, 1989. 14(2): p. 175–85.

126. Reddy, A. C. and B. R. Lokesh, *Studies on the inhibitory effects of curcumin and eugenol on the formation of reactive oxygen species and the oxidation of ferrous iron.* Mol Cell Biochem, 1994. 137(1): p. 1–8.

127. Srivastava, R., *Inhibition of neutrophil response by curcumin.* Agents Actions, 1989. 28(3–4): p. 298–303.

128. Subramanian, M., et al., *Diminution of singlet oxygen-induced DNA damage by curcumin and related antioxidants.* Mutat Res, 1994. 311(2): p. 249–55.

129. Donatus, I. A., Sardjoko, and N. P. Vermeulen, *Cytotoxic and cytoprotective activities of curcumin. Effects on paracetamol-induced cytotoxicity, lipid peroxidation and glutathione depletion in rat hepatocytes.* Biochem Pharmacol, 1990. 39(12): p. 1869–75.

130. Sharma, S. C., et al., *Lipid peroxide formation in experimental inflammation.* Biochem Pharmacol, 1972. 21(8): p. 1210–4.

131. Shalini, V. K. and L. Srinivas, *Lipidperoxide induced DNA damage: protection by turmeric (Curcuma longa).* Mol Cell Biochem, 1987. 77(1): p. 3–10.

132. Soudamini, K. K., et al., *Inhibition of lipidperoxidation and cholesterol levels in mice by curcumin.* Indian J Physiol Pharmacol, 1992. 36(4): p. 239–43.

133. Rao, S. and N. N. A. Rao, *Curcumin inhibits iron-dependent lipid peroxidation.* Int J Pharmaceut, 1993. 100: p. 93–97.

134. Rao, S. and M. N. A. Rao, *Curcuminoids as potent inhibitors of lipid peroxidation.* J Pharm Pharmacol, 1994. 46: p. 1013–1016.

135. Reddy, A. C. and B. R. Lokesh, *Studies on spice principles as antioxidants in the inhibition of lipid peroxidation of rat liver microsomes.* Mol Cell Biochem, 1992. 111(1–2): p. 117–24.

136. Reddy, A. C. and B. R. Lokesh, *Alterations in lipid peroxides in rat liver by dietary n-3 fatty acids: Modulation of antioxidant enzymes by curcumin, eugenol, and vitamin E.* J Nutr Biochem, 1994. 5: p. 181–188.

137. Rajakumar, D. V. and M. N. Rao, *Antioxidant properties of dehydrozingerone and curcumin in rat brain homogenates.* Mol Cell Biochem, 1994. 140(1): p. 73–9.

138. Unnikrishnan, M. K. and M. N. Rao, *Curcumin inhibits nitrogen dioxide induced oxidation of hemoglobin.* Mol Cell Biochem, 1995. 146(1): p. 35–7.

139. Chan, M. M., C. T. Ho, and H. I. Huang, *Effects of three dietary phytochemicals from tea, rosemary and turmeric on inflammation-induced nitrite production.* Cancer Lett, 1995. 96(1): p. 23–9.

140. Joe, B. and B. R. Lokesh, *Role of capsaicin, curcumin and dietary n-3 fatty acids in lowering the generation of reactive oxygen species in rat peritoneal macrophages.* Biochim Biophys Acta, 1994. 1224(2): p. 255–63.

141. Reddy, B. S., et al., *Inhibitory effect of aspirin on azoxymethane-induced colon carcinogenesis in F344 rats.* Carcinogenesis, 1993. 14(8): p. 1493–7.

142. Rao, C. V., et al., *Chemoprevention of colon carcinogenesis by sulindac, a nonsteroidal anti-inflammatory agent.* Cancer Res, 1995. 55(7): p. 1464–72.

143. Boolbol, S. K., et al., *Cyclooxygenase-2 overexpression and tumor formation are blocked by sulindac in a murine model of familial adenomatous polyposis.* Cancer Res, 1996. 56(11): p. 2556–60.

144. Hanif, R., et al., *Curcumin, a natural plant phenolic food additive, inhibits cell proliferation and induces cell cycle changes in colon adenocarcinoma cell lines by a prostaglandin-independent pathway [see comments].* J Lab Clin Med, 1997. 130(6): p. 576–84.

145. Samaha, H. S., et al., *The role of apoptosis in the modulation of colon carcinogenesis by dietary fat and by the organoselenium compound 1,4-phenylenebis(methylene)selenocyanate.* Cancer Epidemiol Biomarkers Prev, 1997. 6(9): p. 699–704.

146. Jiang, M. C., et al., *Curcumin induces apoptosis in immortalized NIH 3T3 and malignant cancer cell lines.* Nutr Cancer, 1996. 26(1): p. 111–20.

147. Xu, Y. X., et al., *Curcumin inhibits IL1 alpha and TNF-alpha induction of AP-1 and NF-κB DNA-binding activity in bone marrow stromal cells.* Hematopathol Mol Hematol, 1997. 11(1): p. 49–62.

148. Singh, S. and B. B. Aggarwal, *Activation of transcription factor NF-kappa B is suppressed by curcumin (diferuloylmethane)[corrected] [published erratum appears in J Biol Chem 1995 December 15;270(50):30235].* J Biol Chem, 1995. 270(42): p. 24995–5000.

149. Chan, M. M., *Inhibition of tumor necrosis factor by curcumin, a phytochemical.* Biochem Pharmacol, 1995. 49(11): p. 1551–6.

150. Stoner, G. D. and H. Mukhtar, *Polyphenols as cancer chemopreventive agents.* J Cell Biochem Suppl, 1995. 22: p. 169–80.

151. Graham, H. N., *Green tea composition, consumption, and polyphenol chemistry.* Prev Med, 1992. 21(3): p. 334–50.

152. Komori, A., et al., *Anticarcinogenic activity of green tea polyphenols.* Jpn J Clin Oncol, 1993. 23(3): p. 186–90.

153. Bushman, J. L., *Green tea and cancer in humans: a review of the literature.* Nutr Cancer, 1998. 31(3): p. 151–9.

154. Tajima, K. and S. Tominaga, *Dietary habits and gastrointestinal cancers: a comparative case-control study of stomach and large intestinal cancers in Nagoya, Japan.* Jpn J Cancer Res, 1985. 76(8): p. 705–16.

155. Yu, G. P. and C. C. Hsieh, *Risk factors for stomach cancer: a population-based case-control study in Shanghai.* Cancer Causes Control, 1991. 2(3): p. 169–74.

156. Yu, G. P., et al., *Green-tea consumption and risk of stomach cancer: a population-based case-control study in Shanghai, China.* Cancer Causes Control, 1995. 6(6): p. 532–8.

157. Ji, B. T., et al., *The influence of cigarette smoking, alcohol, and green tea consumption on the risk of carcinoma of the cardia and distal stomach in Shanghai, China [see comments].* Cancer, 1996. 77(12): p. 2449–57.

158. Gao, Y. T., et al., *Reduced risk of esophageal cancer associated with green tea consumption.* J Natl Cancer Inst, 1994. 86(11): p. 855–8.

159. Ohno, Y., et al., *Tea consumption and lung cancer risk: a case-control study in Okinawa, Japan.* Jpn J Cancer Res, 1995. 86(11): p. 1027–34.

160. Ji, B. T., et al., *Green tea consumption and the risk of pancreatic and colorectal cancers.* Int J Cancer, 1997. 70(3): p. 255–8.

161. Kato, I., et al., *A comparative case-control study of colorectal cancer and adenoma.* Jpn J Cancer Res, 1990. 81(11): p. 1101–8.

162. Khan, S. G., et al., *Enhancement of antioxidant and phase II enzymes by oral feeding of green tea polyphenols in drinking water to SKH-1 hairless mice: possible role in cancer chemoprevention.* Cancer Res, 1992. 52(14): p. 4050–2.

163. Bu-Abbas, A., et al., *Stimulation of rat hepatic UDP-glucuronosyl transferase activity following treatment with green tea.* Food Chem Toxicol, 1995. 33(1): p. 27–30.

164. Smith, T. J. and C. S. Yang, *Effects of food phytochemicals on xenobiotic metabolism and tumorigenesis*, in *Food Phytochemicals I: Fruits and Vegetables*, C.-T. Ho, et al., Editors. 1994, American Chemical Society: Washington D.C. p. 17–23.
165. Sohn, O. S., et al., *Effects of green and black tea on hepatic xenobiotic metabolizing systems in the male F344 rat*. Xenobiotica, 1994. 24(2): p. 119–27.
166. Lee, S. F., Y. C. Liang, and J. K. Lin, *Inhibition of 1,2,4-benzenetriol-generated active oxygen species and induction of phase II enzymes by green tea polyphenols*. Chem Biol Interact, 1995. 98(3): p. 283–301.
167. Uchida, S., et al., *Active oxygen free radicals are scavenged by condensed tannins*. Prog Clin Biol Res, 1988. 280: p. 135–8.
168. Uchida, S., et al., *Radioprotective effects of (-)-epigallocatechin 3-O-gallate(green-tea tannin) in mice*. Life Sci, 1992. 50(2): p. 147–52.
169. Nanjo, F., et al., *Effects of dietary tea catechins on alpha-tocopherol levels, lipid peroxidation, and erythrocyte deformability in rats fed on high palm oil and perilla oil diets*. Biol Pharm Bull, 1993. 16(11): p. 1156–9.
170. Katiyar, S. K., R. Agarwal, and H. Mukhtar, *Inhibition of spontaneous and photo-enhanced lipid peroxidation in mouse epidermal microsomes by epicatechin derivatives from green tea*. Cancer Lett, 1994. 79(1): p. 61–6.
171. Yen, G.-C. and H.-Y. Chen, *Antioxidant activity of various tea extracts in relation to their antimutagenicity*. J Agric Food Chem, 1995. 43: p. 27–32.
172. Klaunig, J. E., *Chemopreventive effects of green tea components on hepatic carcinogenesis*. Prev Med, 1992. 21(4): p. 510–9.
173. Sigler, K. and R. J. Ruch, *Enhancement of gap junctional intercellular communication in tumor promoter-treated cells by components of green tea*. Cancer Lett, 1993. 69(1): p. 15–9.
174. Hu, G., C. Han, and J. Chen, *Inhibition of oncogene expression by green tea and (-)-epigallocatechin gallate in mice*. Nutr Cancer, 1995. 24(2): p. 203–9.
175. Lea, M. A., et al., *Inhibitory effects of tea extracts and (-)-epigallocatechin gallate on DNA synthesis and proliferation of hepatoma and erythroleukemia cells*. Cancer Lett, 1993. 68(2–3): p. 231–6.
176. Stich, H. F., *Teas and tea components as inhibitors of carcinogen formation in model systems and man*. Prev Med, 1992. 21(3): p. 377–84.
177. Xu, G. P., P. J. Song, and P. I. Reed, *Effects of fruit juices, processed vegetable juice, orange peel and green tea on endogenous formation of N-nitrosoproline in subjects from a high-risk area for gastric cancer in Moping County, China*. Eur J Cancer Prev, 1993. 2(4): p. 327–35.
178. Demmig-Adams, B., A. M. Gilmore, and W. W. d. Adams, *Carotenoids 3: in vivo function of carotenoids in higher plants*. Faseb J, 1996. 10(4): p. 403–12.
179. Stahl, W. and H. Sies, *Lycopene: a biologically important carotenoid for humans?* Arch Biochem Biophys, 1996. 336(1): p. 1–9.
180. Gerster, H., *The potential role of lycopene for human health*. J Am Coll Nutr, 1997. 16(2): p. 109–26.
181. Peto, R., et al., *Can dietary beta-carotene materially reduce human cancer rates?* Nature, 1981. 290(5803): p. 201–8.
182. Ziegler, R. G., *A review of epidemiologic evidence that carotenoids reduce the risk of cancer*. J Nutr, 1989. 119(1): p. 116–22.
183. Britton, G., *Structure and properties of carotenoids in relation to function*. Faseb J, 1995. 9(15): p. 1551–8.
184. Olson, J. A. and N. I. Krinsky, *Introduction: the colorful, fascinating world of the carotenoids: important physiologic modulators*. Faseb J, 1995. 9(15): p. 1547–50.
185. Halevy, O. and D. Sklan, *Inhibition of arachidonic acid oxidation by beta-carotene, retinol and alpha-tocopherol*. Biochim Biophys Acta, 1987. 918(3): p. 304–7.
186. Burton, G. W. and K. U. Ingold, *beta-Carotene: an unusual type of lipid antioxidant*. Science, 1984. 224 (4649): p. 569–73.
187. Di Mascio, P., S. Kaiser, and H. Sies, *Lycopene as the most efficient biological carotenoid singlet oxygen quencher*. Arch Biochem Biophys, 1989. 274(2): p. 532–8.
188. Chopra, M., R. L. Willson, and D. I. Thurnham, *Free radical scavenging of lutein in vitro*. Ann N Y Acad Sci, 1993. 691: p. 246–9.
189. Bors, W., M. Saran, and C. Michel, *Radical intermediates involved in the bleaching of the carotenoid crocin. Hydroxyl radicals, superoxide anions and hydrated electrons*. Int J Radiat Biol Relat Stud Phys Chem Med, 1982. 41(5): p. 493–501.
190. Rousseau, E. J., A. J. Davison, and B. Dunn, *Protection by beta-carotene and related compounds against oxygen-mediated cytotoxicity and genotoxicity: implications for carcinogenesis and anticarcinogenesis*. Free Radic Biol Med, 1992. 13(4): p. 407–33.
191. Bohm, F., et al., *Cellular bound beta-carotene quenches singlet oxygen in man*. J Photochem Photobiol B, 1993. 21(2–3): p. 219–21.
192. Khachik, F., et al., *Identification, quantification, and relative concentrations of carotenoids and their metabolites in human milk and serum*. Anal Chem, 1997. 69(10): p. 1873–81.
193. Shah, G. M., U. C. Goswami, and R. K. Bhattacharya, *Action of some retinol derivatives and their provitamins on microsome-catalyzed formation of benzo[a]pyrene-DNA adduct*. J Biochem Toxicol, 1992. 7(3): p. 177–81.
194. Hathcock, J. N., et al., *Evaluation of vitamin A toxicity*. Am J Clin Nutr, 1990. 52(2): p. 183–202.
195. Jyonouchi, H., et al., *Immunomodulating actions of carotenoids: enhancement of in vivo and in vitro antibody production to T-dependent antigens*. Nutr Cancer, 1994. 21(1): p. 47–58.
196. Pung, A., et al., *Beta-carotene and canthaxanthin inhibit chemically- and physically-induced neoplastic transformation in 10T1/2 cells*. Carcinogenesis, 1988. 9(9): p. 1533–9.
197. Hazuka, M. B., et al., *Beta-carotene induces morphological differentiation and decreases adenylate cyclase activity in melanoma cells in culture*. J Am Coll Nutr, 1990. 9(2): p. 143–9.
198. Bertram, J. S., et al., *Diverse carotenoids protect against chemically induced neoplastic transformation*. Carcinogenesis, 1991. 12(4): p. 671–8.
199. Zhang, L. X., R. V. Cooney, and J. S. Bertram, *Carotenoids enhance gap junctional communication and inhibit lipid peroxidation in C3H/10T1/2 cells: relationship to their cancer chemopreventive action*. Carcinogenesis, 1991. 12(11): p. 2109–14.
200. Kvale, G., E. Bjelke, and J. J. Gart, *Dietary habits and lung cancer risk*. Int J Cancer, 1983. 31(4): p. 397–405.
201. Forman, M. R., et al., *The effect of dietary intake of fruits and vegetables on the odds ratio of lung cancer among Yunnan tin miners*. Int J Epidemiol, 1992. 21(3): p. 437–41.
202. Agudo, A., et al., *Vegetable and fruit intake and the risk of lung cancer in women in Barcelona, Spain*. Eur J Cancer, 1997. 33(8): p. 1256–61.

203. Modan, B., H. Cuckle, and F. Lubin, *A note on the role of dietary retinol and carotene in human gastro-intestinal cancer.* Int J Cancer, 1981. 28(4): p. 421–4.
204. Buiatti, E., et al., *A case-control study of gastric cancer and diet in Italy.* Int J Cancer, 1989. 44(4): p. 611–6.
205. Hansson, L. E., et al., *Diet and risk of gastric cancer. A population-based case-control study in Sweden.* Int J Cancer, 1993. 55(2): p. 181–9.
206. Franceschi, S., et al., *Tomatoes and risk of digestive-tract cancers.* Int J Cancer, 1994. 59(2): p. 181–4.
207. Hu, J. F., et al., *Diet and cancer of the colon and rectum: a case-control study in China.* Int J Epidemiol, 1991. 20(2): p. 362–7.
208. Burney, P. G., G. W. Comstock, and J. S. Morris, *Serologic precursors of cancer: serum micronutrients and the subsequent risk of pancreatic cancer.* Am J Clin Nutr, 1989. 49(5): p. 895–900.
209. Mills, P. K., et al., *Cohort study of diet, lifestyle, and prostate cancer in Adventist men.* Cancer, 1989. 64(3): p. 598–604.
210. Giovannucci, E., et al., *Intake of carotenoids and retinol in relation to risk of prostate cancer.* J Natl Cancer Inst, 1995. 87(23): p. 1767–76.
211. Cook-Mozaffari, P. J., et al., *Oesophageal cancer studies in the Caspian Littoral of Iran: results of a case-control study.* Br J Cancer, 1979. 39(3): p. 293–309.
212. Zhang, S., et al., *Measurement of retinoids and carotenoids in breast adipose tissue and a comparison of concentrations in breast cancer cases and control subjects.* Am J Clin Nutr, 1997. 66(3): p. 626–32.
213. Giovannucci, E., *Tomatoes, tomato-based products, lycopene, and cancer: review of the epidemiologic literature.* J Natl Cancer Inst, 1999. 91(4): p. 317–31.
214. Erdman, J. W., Jr., T. L. Bierer, and E. T. Gugger, *Absorption and transport of carotenoids.* Ann N Y Acad Sci, 1993. 691: p. 76–85.
215. Parker, R. S., *Absorption, metabolism, and transport of carotenoids.* Faseb J, 1996. 10(5): p. 542–51.
216. Bierer, T. L., N. R. Merchen, and J. W. Erdman, Jr., *Comparative absorption and transport of five common carotenoids in preruminant calves.* J Nutr, 1995. 125(6): p. 1569–77.
217. Clinton, S. K., *Lycopene: chemistry, biology, and implications for human health and disease.* Nutr Rev, 1998. 56(2 Pt 1): p. 35–51.
218. Fand, I. and W. P. McNally, *Whole-body localization of 14C-tocopheryl acetate in the rat following oral administration.* Arch Int Pharmacodyn Ther, 1981. 250(1): p. 4–17.
219. Bendich, A. and L. J. Machlin, *Safety of oral intake of vitamin E.* Am J Clin Nutr, 1988. 48(3): p. 612–9.
220. Traber, M. G., et al., *Discrimination between forms of vitamin E by humans with and without genetic abnormalities of lipoprotein metabolism.* J Lipid Res, 1992. 33(8): p. 1171–82.
221. Traber, M. G., et al., *Impaired ability of patients with familial isolated vitamin E deficiency to incorporate alpha-tocopherol into lipoproteins secreted by the liver.* J Clin Invest, 1990. 85(2): p. 397–407.
222. Traber, M. G., et al., *RRR- and SRR-alpha-tocopherols are secreted without discrimination in human chylomicrons, but RRR-alpha-tocopherol is preferentially secreted in very low density lipoproteins.* J Lipid Res, 1990. 31(4): p. 675–85.
223. Traber, M. G., et al., *Impaired discrimination between stereoisomers of alpha-tocopherol in patients with familial isolated vitamin E deficiency.* J Lipid Res, 1993. 34(2): p. 201–10.
224. Traber, M. G., A. Elsner, and R. Brigelius-Flohe, *Synthetic as compared with natural vitamin E is preferentially excreted as alpha-CEHC in human urine: studies using deuterated alpha-tocopheryl acetates.* FEBS Lett, 1998. 437(1–2): p. 145–8.
225. Helzlsouer, K. J., et al., *Summary of the round table discussion on strategies for cancer prevention: diet, food, additives, supplements, and drugs.* Cancer Res, 1994. 54(7 Suppl): p. 2044s–2051s.
226. McEvoy, G. K., *Vitamin E, in AHFS Drug Information 94.* 1994, American Society of Hospital Pharmacists: Bethesda. p. 2415–2417.
227. *Vitamin E, in USP DI-Volume III. Approved Drug Products and Legal Requirements*, I. United States Pharmacopeia Convention, Editor. 1994, Rand McNally: Taunton. p. 485–486.
228. Kappus, H. and A. T. Diplock, *Tolerance and safety of vitamin E: a toxicological position report.* Free Radic Biol Med, 1992. 13(1): p. 55–74.
229. Niki, E., et al, *Synergistic inhibition of oxidation of phosphatidylcholine liposome in aqueous dispersion by vitamin E and vitamin C.* Bull Chem Soc Jpn, 1985.58: p.1971.
230. Doba, T., G. W. Burton, and K. U. Ingold, *Antioxidant and co-antioxidant activity of vitamin C. The effect of vitamin C, either alone or in the presence of vitamin E or a water-soluble vitamin E analogue, upon the peroxidation of aqueous multilamellar phospholipid liposomes.* Biochim Biophys Acta, 1985. 835(2): p. 298–303.
231. Stevenson, N. R. and M. K. Brush, *Existence and characteristics of Na positive-dependent active transport of ascorbic acid in guinea pig.* Am J Clin Nutr, 1969. 22(3): p. 318–26.
232. Kallner, A., D. Hartmann, and D. Hornig, *On the absorption of ascorbic acid in man.* Int J Vitam Nutr Res, 1977. 47(4): p. 383–8.
233. Hardman, J. G., et al, *Goodman & Gilman's The Pharmacological Basis of Therapuetics.* 9th ed. 1996, New York: McGraw-Hill.
234. Swanson, C. A., et al., *Human [74Se]selenomethionine metabolism: a kinetic model.* Am J Clin Nutr, 1991. 54(5): p. 917–26.
235. McGuire, M. K., et al., *Selenium status of infants is influenced by supplementation of formula or maternal diets.* Am J Clin Nutr, 1993. 58(5): p. 643–8.
236. Deagen, J. T., et al., *Effects of dietary selenite, selenocystine and selenomethionine on selenocysteine lyase and glutathione peroxidase activities and on selenium levels in rat tissues.* J Nutr, 1987. 117(1): p. 91–8.
237. Franke, K. W., *New toxicant occurring natrually in certain samples of plant foodstuffs: results obtained in preliminary feeding trials.* J Nutr, 1934. 8: p. 597–603.
238. Garland, M., et al., *The epidemiology of selenium and human cancer*, in *Natural Antioxidants in Human Health and Disease*, B. Frei, Editor. 1994, Academic Press: San Diego. p. 263–281.
239. Ip, C., *Differential effect of dietary methionine on the bibpotency of selenomethionine and selenite in cancer chemoprevention.* J Natl Cancer Inst, 1988. 80(4): p. 258–62.
240. Olsson, B., et al., *Pharmacokinetics and bioavailability of reduced and oxidized N-acetylcysteine.* Eur J Clin Pharmacol, 1988. 34(1): p. 77–82.
241. Borgstrom, L., B. Kagedal, and O. Paulsen, *Pharmacokinetics of N-acetylcysteine in man.* Eur J Clin Pharmacol, 1986. 31(2): p. 217–22.
242. De Caro, L., et al., *Pharmacokinetics and bioavailability of oral acetylcysteine in healthy volunteers.* Arzneimittelforschung, 1989. 39(3): p. 382–6.

243. Sjodin, K., et al., *Metabolism of N-acetyl-L-cysteine. Some structural requirements for the deacetylation and consequences for the oral bioavailability.* Biochem Pharmacol, 1989. 38(22): p. 3981–5.
244. Jones, A. L., et al., *Pharmacokinetics of N-acetylcysteine are altered in patients with chronic liver disease.* Aliment Pharmacol Ther, 1997. 11(4): p. 787–91.
245. Anonymous, *Clinical development plan: curcumin.* J Cell Biochem Suppl, 1996. 26: p. 72–85.
246. Shoba, G., et al., *Influence of piperine on the pharmacokinetics of curcumin in animals and human volunteers.* Planta Med, 1998. 64(4): p. 353–6.
247. Anonymous, *Clinical Development Plan: tea extracts green tea polyphenols epigallocatechin gallate.* Journal of Cellular Biochemistry, 1996. 26s: p. 236–257.
248. Krinsky, N. I., D. G. Cornwell, and J. L. Oncley, *The transport of vitamin A and carotenoids in human plasma.* Arch Biochem Biophys, 1958. 73: p. 233–46.
249. Stahl, W. and H. Sies, *Uptake of lycopene and its geometrical isomers is greater from heat-processed than from unprocessed tomato juice in humans.* J Nutr, 1992. 122(11): p. 2161–6.
250. Koonsvitsky, B. P., et al., *Olestra affects serum concentrations of alpha-tocopherol and carotenoids but not vitamin D or vitamin K status in free-living subjects.* J Nutr, 1997. 127(8 Suppl): p. 1636S–1645S.
251. Cooper, D. A., D. R. Webb, and J. C. Peters, *Evaluation of the potential for olestra to affect the availability of dietary phytochemicals.* J Nutr, 1997. 127(8 Suppl): p. 1699S–1709S.
252. Schlagheck, T. G., et al., *Olestra dose response on fat-soluble and water-soluble nutrients in humans.* J Nutr, 1997. 127(8 Suppl): p. 1646S–1665S.
253. Covey, D. S., et al., *Clinical Development Plan: beta-carotene and other carotenoids.* J Cell Biochem Suppl, 1994. 20: p. 110–140.
254. Kelloff, G. J., et al., *Clinical development plan: beta-carotene and other carotenoids.* J Cell Biochem Suppl, 1994. 20: p. 110–140.
255. Hill M. J., M. B., and Bussey H J R, *Aetiology of adenoma-carcinoma sequence in large bowel.* Lancet, 1978. 1: p. 245–7.
256. Potter, J. D., *Colorectal cancer: molecules and populations.* J Nat Cancer Inst, 1999. 91(11): p. 916–932.
257. *Cancer Facts and Figures—1997,.* 1997, American Cancer Society: Atlanta: ACS.
258. W C R F Panel, J. P.-C., *Chapter 4.10 Colon, Rectum,* in *Diet, Nutrition, and the Prevention of Cancer: a Global Perspective.* 1996, WCRF/AICR. p. 216–251.
259. Haenszel, W., *Cancer Mortality among the foreign born in the United States.* J Natl Cancer Inst, 1961. 26: p. 37–132.
260. McMichael, A. J. and G. G. Giles, *Cancer in migrants to Australia: extending the descriptive epidemiological data.* Cancer Res, 1988. 48(3): p. 751–6.
261. Nelson, N. J., *Is chemoprevention overrated or underfunded.* J Natl Cancer Inst, 1996. 88: p. 947–9.
262. Lynch, H. T. and T. Smyrk, *Hereditary nonpolyposis colorectal cancer (Lynch syndrome). An updated review.* Cancer, 1996. 78(6): p. 1149–67.
263. Winawer, S. J., et al., *Colorectal cancer screening: clinical guidelines and rationale [see comments] [published errata appear in Gastroenterology 1997 Mar; 112(3):1060 and 1998 March; 114(3):625].* Gastroenterology, 1997. 112(2): p. 594–642.
264. Turesky, R. J., et al., *Metabolic activation of carcinogenic heterocyclic aromatic amines by human liver and colon.* Carcinogenesis, 1991. 12(10): p. 1839–45.
265. Kadlubar, F. F., et al., *Polymorphisms for aromatic amine metabolism in humans: relevance for human carcinogenesis.* Environ Health Perspect, 1992. 98: p. 69–74.
266. Freudenheim, J. L., et al., *Folate intake and carcinogenesis of the colon and rectum.* Int J Epidemiol, 1991. 20(2): p. 368–74.
267. Giovannucci, E., et al., *Alcohol, low-methionine—low-folate diets, and risk of colon cancer in men [see comments].* J Natl Cancer Inst, 1995. 87(4): p. 265–73.
268. Giovannucci, E., et al., *Folate, methionine, and alcohol intake and risk of colorectal adenoma [see comments].* J Natl Cancer Inst, 1993. 85(11): p. 875–84.
269. Slattery, M. L., et al., *Are dietary factors involved in DNA methylation associated with colon cancer?* Nutr Cancer, 1997. 28(1): p. 52–62.
270. Ulrich, C. M., et al., *Colorectal Adenomas and the C677 MTCHR Polymorphism: Evidence for gene-environment interaction?* Cancer Epi Biomar Prev, 1999. 8: p. 659–668.
271. Tomeo, C. A., et al., *Harvard Report on Cancer Prevention. Volume 3: prevention of colon cancer in the United States.* Cancer Causes Control, 1999 10(3): p. 167–80.
272. Parkin, D. M. and C. S. Muir, *Cancer Incidence in Five Continents. Comparability and quality of data.* IARC Sci Publ, 1992. 120: p. 45–173.
273. WCRF Panel, J. P.-C., *Chapter 2 Diet and the cancer process,* in *Food, Nutrition and the Prevention of Cancer: a global perspective.* 1996, WCRF/AICR. p. 54–71.
274. Potter, J., et al., *Colon cancer: a review of the epidemiology.* Epidemiol Rev, 1993. 15: p. 499–545.
275. Trock, B., E. Lanza, and P. Greenwald, *Dietary fiber, vegetables, and colon cancer: critical review and meta-analyses of the epidemiologic evidence.* J Natl Cancer Inst, 1990. 82(8): p. 650–61.
276. Ma, J., et al., *Methylenetetrahydrofolate reductase polymorphism, dietary interactions, and risk of colorectal cancer.* Cancer Res, 1997.57(6): p.1098–102.
277. Chen, J., et al., *A methylenetetrahydrofolate reductase polymorphism and the risk of colorectal cancer.* Cancer Res, 1996. 56(21): p. 4862–4.
278. Vane, J. R., R. J. Flower, and R. M. Botting, *History of aspirin and its mechanism of action.* Stroke, 1990. 21(12 Suppl): p. IV12–23.
279. Wright, F., *Historical overview of NSAIDs.* Eur J Rheumatol Inflamm, 1993. 13(1): p. 4–6.
280. Lewis, W. H. and M. P. F. Elvin-Lewis, in *Medical Botany: Plants Affecting Man's Health.* 1977, John Wiley & Sons: New York. p. 150–152.
281. Insel, P., *Chapter 27 Analgesic-Antipyretic and Anti-inflammatory Agents and Drugs Employed in the Treatment of Gout,* in *Goodman & Gillman's The Pharmacological Basis of Therapeutics, Ninth Edition,* J. G. Hardman, Limbird, L. E., Molinoff, P. B., Ruddon, R. W. and Gillman, A. G., Editor. 1996, McGraw-Hill: New York. p. 617–657.
282. Kune, G. A., S. Kune, and L. F. Watson, *Colorectal cancer risk, chronic illnesses, operations, and medications: case control results from the Melbourne Colorectal Cancer Study.* Cancer Res, 1988. 48(15): p. 4399–404.
283. Rosenberg, L., et al., *A hypothesis: nonsteroidal anti-inflammatory drugs reduce the incidence of large-bowel cancer [see comments].* J Natl Cancer Inst, 1991. 83(5): p.355–8.
284. Rosenberg, L., C. Louik, and S. Shapiro, *Nonsteroidal antiinflammatory drug use and reduced risk of large bowel carcinoma.* Cancer, 1998. 82(12): p. 2326–33.

285. Suh, O., C. Mettlin, and N. J. Petrelli, *Aspirin use, cancer, and polyps of the large bowel.* Cancer, 1993. 72(4): p. 1171–7.
286. Peleg, II, et al., *Aspirin and nonsteroidal anti-inflammatory drug use and the risk of subsequent colorectal cancer* [see comments]. Arch Intern Med, 1994. 154(4): p. 394–9.
287. Muscat, J. E., S. D. Stellman, and E. L. Wynder, *Nonsteroidal antiinflammatory drugs and colorectal cancer* [see comments]. Cancer, 1994. 74(7): p. 1847–54.
288. La Vecchia, C., et al., *Aspirin and colorectal cancer.* Br J Cancer, 1997. 76(5): p. 675–7.
289. Schreinemachers, D. M. and R. B. Everson, *Aspirin use and lung, colon, and breast cancer incidence in a prospective study* [see comments]. Epidemiology, 1994. 5(2): p. 138–46.
290. Giovannucci, E., et al., *Aspirin use and the risk for colorectal cancer and adenoma in male health professionals* [see comments]. Ann Intern Med, 1994. 121(4): p. 241–6.
291. Giovannucci, E., et al., *Aspirin and the risk of colorectal cancer in women* [see comments]. N Engl J Med, 1995. 333(10): p. 609–14.
292. Paganini-Hill, A., et al., *Aspirin use and chronic diseases: a cohort study of the elderly* [see comments]. Bmj, 1989. 299(6710): p. 1247–50.
293. Gann, P. H., et al., *Low-dose aspirin and incidence of colorectal tumors in a randomized trial* [see comments]. J Natl Cancer Inst, 1993. 85(15): p. 1220–4.
294. Sturmer, T., et al., *Aspirin use and colorectal cancer: post-trial follow-up data from the Physicians' Health Study.* Ann Intern Med, 1998. 128(9): p. 713–20.
295. Logan, R. F., et al., *Effect of aspirin and non-steroidal anti-inflammatory drugs on colorectal adenomas: case-control study of subjects participating in the Nottingham faecal occult blood screening programme* [see comments]. Bmj, 1993. 307(6899): p. 285–9.
296. Greenberg, E. R., et al., *Reduced risk of large-bowel adenomas among aspirin users. The Polyp Prevention Study Group.* J Natl Cancer Inst, 1993. 85(11): p. 912–6.
297. Giardiello, F. M., et al., *Treatment of colonic and rectal adenomas with sulindac in familial adenomatous polyposis.* N Engl J Med, 1993. 328(18): p. 1313–6.
298. Ruschoff, J., et al., *Aspirin suppresses the mutator phenotype associated with hereditary nonpolyposis colorectal cancer by genetic selection.* Proc Natl Acad Sci USA, 1998. 95(19): p. 11301–6.
299. Isomaki, H. A., T. Hakulinen, and U. Joutsenlahti, *Excess risk of lymphomas, leukemia and myeloma in patients with rheumatoid arthritis.* J Chronic Dis, 1978. 31(11): p. 691–6.
300. Laakso, M., et al., *Cancer mortality in patients with rheumatoid arthritis.* J Rheurnatol, 1986. 13(3): p. 522–6.
301. Gridley, G., et al., *Incidence of cancer among patients with rheumatoid arthritis* [see comments]. J Natl Cancer Inst, 1993. 85(4): p. 307–11.
302. Pollard, M. and P. H. Luckert, *Indomethacin treatment of rats with dimethylhydrazine-induced intestinal tumors.* Cancer Treat Rep, 1980. 64(12): p. 1323–7.
303. Narisawa, T., et al., *Inhibition of development of methylnitrosourea-induced rat colon tumors by indomethacin treatment.* Cancer Res, 1981. 41(5): p. 1954–7.
304. Pollard, M. and P. H. Luckert, *Effect of indomethacin on intestinal tumors induced in rats by the acetate derivative of dimethylnitrosamine.* Science, 1981. 214(4520): p. 558–9.
305. Pollard, M., P. H. Luckert, and M. A. Schmidt, *The suppressive effect of piroxicam on autochthonous intestinal tumors in the rat.* Cancer Lett, 1983. 21(1): p. 57–61.
306. Pollard, M. and P. H. Luckert, *Prolonged antitumor effect of indomethacin on autochthonous intestinal tumors in rats.* J Natl Cancer Inst, 1983. 70(6): p. 1103–5.
307. Narisawa, T., et al., *Inhibition of initiation and promotion by N-methylnitrosourea-induced colon carcinogenesis in rats by non-steroid anti-inflammatory agent indomethacin.* Carcinogenesis, 1983.4(10): p. 1225–7.
308. Pollard, M. and P. H. Luckert, *Effect of piroxicam on primary intestinal tumors induced in rats by N-methylnitrosourea.* Cancer Lett, 1984. 25(2): p. 117–21.
309. Reddy, B. S., H. Maruyarna, and G. Kelloff, *Dose-related inhibition of colon carcinogenesis by dietary piroxicam, a nonsteroidal antiinflammatory drug, during different stages of rat colon tumor development.* Cancer Res, 1987. 47(20): p. 5340–6.
310. Moorghen, M., et al., *A protective effect of sulindac against chemically-induced primary colonic tumours in mice.* J Pathol, 1988. 156(4): p. 341–7.
311. Craven, P. A., DeRubertis, F R, *The evolution of cancer of the colon and rectum.* Cancer, 1992. 36: p. 2251–2270.
312. Kawamori, T., et al., *Chemopreventive activity of celecoxib, a specific cyclooxygenase-2 inhibitor, against colon carcinogenesis.* Cancer Res, 1998. 58(3): p. 409–12.
313. IARC, *General Remarks*, in *Non-Steroidal Anti-Inflammatory Drugs*, I.A.f.R.o. Cancer, Editor. 1997, International Agency for Cancer Research: Leyon, France. p. 15–39.
314. Loll, P. J., D. Picot, and R. M. Garavito, *The structural basis of aspirin activity inferred from the crystal structure of inactivated prostaglandin H2 synthase* [see comments]. Nat Struct Biol, 1995. 2(8): p. 637–43.
315. Picot, D., P. J. Loll, and R. M. Garavito, *The X-ray crystal structure of the membrane protein prostaglandin H2 synthase-1* [see comments]. Nature, 1994. 367(6460): p. 243–9.
316. Loll, P. J., et al., *Synthesis and use of iodinated nonsteroidal antiinflammatory drug analogs as crystallographic probes of the prostaglandin H2 synthase cyclooxygenase active site.* Biochemistry, 1996. 35(23): p. 7330–40.
317. Marnett, L. J., *ASPIRIN AND THE POTENTIAL ROLE OF PROSTAGLANDINS IN COLON CANCER* (311 Refs). Cancer Res, 1992.52(20): p.5575–89.
318. Kalgutkar, A. S., et al., *Aspirin-like molecules that covalently inactivate cyclooxygenase-2* [see comments]. Science, 1998. 280(5367): p. 1268–70.
319. Barnes, C. J., et al., *Non-steroidol anti-inflammatory drug effect on crypt cell proliferation and apoptosis during initiation of rat colon carcinogenesis.* Br J Cancer, 1998. 77(4): p. 573–80.
320. Tsujii, M., et al., *Cyclooxygenase regulates angiogenesis induced by colon cancer cells* [published erratum appears in Cell 1998 July 24;94(2):following 271]. Cell, 1998. 93(5): p. 705–16.
321. *Non-Steroidal Anti-inflammatory Drugs.* IARC Handbooks of Cancer Prevention. Vol. 1. 1997, Lyon: International Agency for Research on Cancer.
322. Ciolino, H. P., et al., *Effect of curcumin on the aryl hydrocarbon receptor and cytochrome P450 1A1 in MCF-7 human breast carcinoma cells.* Biochem Pharmacol, 1998. 56(2): p. 197–206.
323. Zhang, F., et al., *Curcumin inhibits cyclooxygenase-2 transcription in bile acid- and phorbol ester-treated*

*human gastrointestinal epithelial cells.* Carcinogenesis, 1999. 20(3): p. 445–51.
324. Deodhar, S. D., R. Sethi, and R. C. Srimal, *Preliminary study on antirheumatic activity of curcumin (diferuloyl methane).* Indian J Med Res, 1980. 71: p. 632–4.
325. Srimal, R. C., *Curcumin.* Drugs Future, 1987. 12: p. 331–333.
326. Potter, J. D., *Risk factors for colon neoplasia—epidemiology and biology.* Eur J Cancer, 1995. 31A(7–8): p. 1033–8.
327. Wu, A. H., Paganini-Hill A., Ross, R. K., and Henderson, B. E., *Alcohol, physical activity, and other risk factors for colorectal cancer: A prospective study.* Br J Cancer, 1987. 55: p. 687–694.
328. Willett, W. C., et al., *Relation of meat, fat, and fiber intake to the risk of colon cancer in a prospective study among women [see comments].* N Engl J Med, 1990. 323(24): p. 1664–72.
329. Stemmermann, G. N., A. Nomura, and P. H. Chyou, *The influence of dairy and nondairy calcium on subsite large-bowel cancer risk.* Dis Colon Rectum, 1990. 33(3): p. 190–4.
330. Kampman, E., et al., *Fermented dairy products, calcium, and colorectal cancer in The Netherlands Cohort Study.* Cancer Res, 1994. 54(12): p. 3186–90.
331. Kearney, J., et al., *Calcium, vitamin D, and dairyfoods and the occurrence of colon cancer in men.* Am J Epidemiol, 1996. 143(9): p. 907–17.
332. Heilbrun, L. K., et al., *Colon cancer and dietary fat, phosphorus, and calcium in Hawaiian-Japanese men.* Am J Clin Nutr, 1986. 43(2): p. 306–9.
333. Garland, C., et al., *Dietary vitamin D and calcium and risk of colorectal cancer: a 19-year prospective study in men.* Lancet, 1985. 1(8424): p. 307–9.
334. Bostick, R. M., et al., *Calcium and colorectal epithelial cell proliferation: a preliminary randomized, double-blinded, placebo-controlled clinical trial.* J Natl Cancer Inst, 1993. 85(2): p. 132–41.
335. Zaridze, D., Filipchenko, V., Kustov, V., et al., *Diet and colorectal cancer: results of two case-control studies in Russia.* Eur J Cancer, 1993. 29A: p. 112–115.
336. Arbman, G., et al., *Cereal fiber, calcium, and colorectal cancer.* Cancer, 1992. 69(8): p. 2042–8.
337. Benito, E., et al., *A population-based case-control study of colorectal cancer in Majorca. I. Dietary factors.* Int J Cancer, 1990. 45(1): p. 69–76.
338. Graham, S., et al., *Dietary epidemiology of cancer of the colon in western New York.* Am J Epidemiol, 1988. 128(3): p. 490–503.
339. Freudenheim, J. L., et al., *A case-control study of diet and rectal cancer in western New York.* Am J Epidemiol, 1990. 131(4): p. 612–24.
340. Kune, G. A. and S. Kune, *The nutritional causes of colorectal cancer: an introduction to the Melbourne study.* Nutr Cancer, 1987. 9(1): p. 1–4.
341. Macquart-Moulin, G., et al., *Case-control study on colorectal cancer and diet in Marseilles.* Int J Cancer, 1986. 38(2): p. 183–91.
342. Slattery, M. L., A. W. Sorenson, and M. H. Ford, *Dietary calcium intake as a mitigating factor in colon cancer.* Am J Epidemiol, 1988. 128(3): p.504–14.
343. Lee, H. P., et al., *Colorectal cancer and diet in an Asian population—a case-control study among Singapore Chinese.* Int J Cancer, 1989. 43(6): p. 1007–16.
344. Whittemore, A. S., et al., *Diet, physical activity, and colorectal cancer among Chinese in North America and China.* J Natl Cancer Inst, 1990. 82(11): p. 915–26.
345. Peters, R. K., et al., *Diet and colon cancer in Los Angeles County, Calif.* Cancer Causes Control, 1992. 3(5): p. 457–73.
346. Meyer, F. and E. White, *Alcohol and nutrients in relation to colon cancer in middle-aged adults.* Am J Epidemiol, 1993. 138(4): p. 225–36.
347. Tuyns, A. J., M. Haelterman, and R. Kaaks, *Colorectal cancer and the intake of nutrients: oligosaccharides are a risk factor, fats are not. A case-control study in Belgium.* Nutr Cancer, 1987. 10(4): p. 181–96.
348. Negri, E., et al., *Calcium, dairy products, and colorectal cancer.* Nutr Cancer, 1990. 13(4): p. 255–62.
349. Bergsma-Kadijk, J. A., et al., *Calcium does not protect against colorectal neoplasia.* Epidemiology, 1996. 7(6): p. 590–7.
350. Baron, J. A., et al., *Calcium supplements for the prevention of colorectal adenomas. Calcium Polyp Prevention Study Group [see comments].* N Engl J Med, 1999. 340(2): p. 101–7.
351. Lipkin, M. and H. Newmark, *Effect of added dietary calcium on colonic epithelial-cell proliferation in subjects at high risk for familial colonic cancer.* N Engl J Med, 1985. 313(22): p. 138–14.
352. Lipkin, M., et al., *Colonic epithelial cell proliferation in responders and nonresponders to supplemental dietary calcium.* Cancer Res, 1989. 49(1): p. 248–54.
353. Wargovich, M. J., et al., *Calcium supplementation decreases rectal epithelial cell proliferation in subjects with sporadic adenoma [see comments].* Gastroenterology, 1992. 103(1): p. 92–7.
354. Bostick, R. M., et al., *Calcium and colorectal epithelial cell proliferation in sporadic adenoma patients: a randomized, double-blinded, placebo-controlled clinical trial [see comments].* J Natl Cancer Inst, 1995. 87(17): p. 1307–15.
355. Holt, P. R., et al., *Modulation of abnormal colonic epithelial cell proliferation and differentiation by low-fat dairy foods: a randomized controlled trial [see comments].* Jama, 1998. 280(12): p. 1074–9.
356. Pence, B. C. and F. Buddingh, *Inhibition of dietary fat-promoted colon carcinogenesis in rats by supplemental calcium or vitamin D3.* Carcinogenesis, 1988. 9(1): p. 187–90.
357. Wargovich, M. J., et al., *Inhibition of the promotional phase of azoxymethane-induced colon carcinogenesis in the F344 rat by calcium lactate: effect of simulating two human nutrient density levels.* Cancer Lett, 1990. 53(1): p. 17–25.
358. Lipkin, M. and H. Newmark, *Calcium and the prevention of colon cancer.* J Cell Biochem Suppl, 1995. 22: p. 65–73.
359. Buset, M., Lipkin, M., Winawer, S., et al., *Inhibition of human colonic epithelial cell proliferation in vivo and in vitro by calcium.* Cancer Res, 1987. 46: p. 5426–5430.
360. Arlow, F. L., et al., *Attenuation of azoxymethane-induced colonic mucosal ornithine decarboxylase and tyrosine kinase activity by calcium in rats.* Cancer Res, 1989. 49(21): p. 5884–8.
361. Wargovich, M. J., et al., *Calcium ameliorates the toxic effect of deoxycholic acid on colonic epithelium.* Carcinogenesis, 1983. 4(9): p. 1205–7.
362. Vogel, V. G. and R. S. McPherson, *Dietary epidemiology of colon cancer.* Hematol Oncol Clin North Am, 1989. 3(1): p. 35–63.
363. Marcus, R., *Chapter 61 Agents Affecting Calcification and Bone Turnover, in Goodman & Gillman's The Pharmacological Basis of Therapeutics, Ninth Edition,* J. G.

Hardman, Limbird, L. E., Molinoff, P. B., Ruddon, R. W. and Gillman, A. G., Editor. 1996, McGraw-Hill: New York.

364. Garland, C. F. and F. C. Garland, *Do sunlight and vitamin D reduce the likelihood of colon cancer?* Int J Epidemiol, 1980. 9(3): p. 227–31.

365. Gorham, E. D., C. F. Garland, and F. C. Garland, *Acid haze air pollution and breast and colon cancer mortality in 20 Canadian cities.* Can J Public Health, 1989. 80(2): p. 96–100.

366. Emerson, J. C. and N. S. Weiss, *Colorectal cancer and solar radiation.* Cancer Causes Control, 1992. 3(1): p. 95–9.

367. Bostick, R. M., et al., *Relation of calcium, vitamin D, and dairy food intake to incidence of colon cancer among older women. The Iowa Women's Health Study.* Am J Epidemiol, 1993. 137(12): p. 1302–17.

368. Martinez, M. E., et al., *Calcium, vitamin D, and the occurrence of colorectal cancer among women.* J Natl Cancer Inst, 1996. 88(19): p. 1375–82.

369. Zheng, W., et al., *A prospective cohort study of intake of calcium, vitamin D, and other micronutrients in relation to incidence of rectal cancer among postmenopausal women.* Cancer Epidemiol Biomarkers Prev, 1998. 7(3): p. 221–5.

370. Benito, E., et al., *Nutritional factors in colorectal cancer risk: a case-control study in Majorca.* Int J Cancer, 1991. 49(2): p. 161–7.

371. Boutron, M. C., et al., *Calcium, phosphorus, vitamin D, dairy products and colorectal carcinogenesis: a French case—control study [see comments].* Br J Cancer, 1996. 74(1): p. 145–51.

372. Pritchard, R. S., J. A. Baron, and M. Gerhardsson de Verdier, *Dietary calcium, vitamin D, and the risk of colorectal cancer in Stockholm, Sweden.* Cancer Epidemiol Biomarkers Prev, 1996. 5(11): p. 897–900.

373. Marcus, P. M. and P. A. Newcomb, *The association of calcium and vitamin D, and colon and rectal cancer in Wisconsin women.* Int J Epidemiol, 1998. 27(5): p. 788–93.

374. Garland, C. F., et al., *Serum 25-hydroxyvitamin D and colon cancer: eight-year prospective study [see comments].* Lancet, 1989. 2(8673): p. 1176–8.

375. Tangrea, J., et al., *Serum levels of vitamin D metabolites and the subsequent risk of colon and rectal cancer in Finnish men.* Cancer Causes Control, 1997. 8(4): p. 615–25.

376. Niv, Y., et al., *In colorectal carcinoma patients, serum vitamin D levels vary according to stage of the carcinoma.* Cancer, 1999. 86(3): p. 391–7.

377. Ferraroni, M., et al., *Selected micronutrient intake and the risk of colorectal cancer.* Br J Cancer, 1994. 70(6): p. 1150–5.

378. Neugut, A. I., et al., *The effect of calcium and vitamin supplements on the incidence and recurrence of colorectal adenomatous polyps.* Cancer, 1996. 78(4): p. 723–8.

379. Shabahang, M., et al., *Growth inhibition of HT-29 human colon cancer cells by analogues of 1,25-dihydroxyvitamin D3.* Cancer Res, 1994. 54(15): p.4057–64.

380. Zhao, X. and D. Feldman, *Regulation of vitamin D receptor abundance and responsiveness during differentiation of HT-29 human colon cancer cells.* Endocrinology, 1993. 132(4): p. 1808–14.

381. Sitrin, M. D., et al., *Dietary calcium and vitamin D modulate 1,2-dimethylhydrazine-induced colonic carcinogenesis in the rat.* Cancer Res, 1991. 51(20): p. 5608–13.

382. Cross, H. S., et al., *Growth control of human colon cancer cells by vitamin D and calcium in vitro.* J Natl Cancer Inst, 1992. 84(17): p. 1355–7.

383. DeLuca, H. F. and V. Ostrem, *The relationship between the vitamin D system and cancer.* Adv Exp Med Biol, 1986. 206: p. 413–29.

384. Wargovich, M. J. and P. H. Lointier, *Calcium and vitamin D modulate mouse colon epithelial proliferation and growth characteristics of a human colon tumor cell line.* Can J Physiol Pharmacol, 1987. 65(3): p. 472–7.

385. Brenner, R. V., et al., *The antiproliferative effect of vitamin D analogs on MCF-7 human breast cancer cells.* Cancer Lett, 1995. 92(1): p. 77–82.

386. Frampton, R. J., et al., *Presence of 1,25-dihydroxyvitamin D3 receptors in established human cancer cell lines in culture.* Cancer Res, 1982. 42(3): p. 1116–9.

387. Thomas, M. G., et al., *Vitamin D receptor expression in colorectal cancer.* J Clin Pathol, 1999. 52(3): p. 181–3.

388. Belleli, A., et al., *A protective role of 1,25-dihydroxyvitamin D3 in chemically induced rat colon carcinogenesis.* Carcinogenesis, 1992. 13(12): p. 2293–8.

389. Lointier, P., et al., *The role of vitamin D3 in the proliferation of a human colon cancer cell line in vitro.* Anticancer Res, 1987. 7(4B): p. 817–21.

390. Cross, H. S., C. Huber, and M. Peterlik, *Antiproliferative effect of 1,25-dihydroxyvitamin D3 and its analogs on human colon adenocarcinoma cells (CaCo-2): influence of extracellular calcium.* Biochem Biophys Res Commun, 1991. 179(1): p. 57–62.

391. Colston, K. W., et al., *Effects of synthetic vitamin D analogues on breast cancer cell proliferation in vivo and in vitro.* Biochem Pharmacol, 1992. 44(4): p. 693–702.

392. Norman, A. W., et al., *Structure-function studies on analogues of 1 alpha,25-dihydroxyvitamin D3: differential effects on leukemic cell growth, differentiation, and intestinal calcium absorption.* Cancer Res, 1990. 50(21): p. 6857–64.

393. Reitsma, P. H., et al., *Regulation of myc gene expression in HL-60 leukaemia cells by a vitamin D metabolite.* Nature, 1983. 306(5942): p. 492–4.

394. Koizumi, T., et al., *Suppression of c-myc mRNA expression by steroid hormones in HTLV-I-infected T-cell line, KH-2.* Int J Cancer, 1989. 44(4): p. 701–6.

395. Brelvi, Z. S. and G. P. Studzinski, *Inhibition of DNA synthesis by an inducer of differentiation of leukemic cells, 1 alpha, 25 dihydroxy vitamin D3, precedes down regulation of the c-myc gene.* J Cell Physiol, 1986. 128(2): p. 171–9.

396. Karmali, R., et al., *1,25(OH)2D3 regulates c-myc mRNA levels in tonsillar T lymphocytes.* Immunology, 1991. 74(4): p. 589–93.

397. Tu-Yu, A. H., R. C. Morris, and H. E. Ives, *Differential modulation of fos and jun gene expression by 1,25-dihydroxyvitamin D3.* Biochem Biophys Res Commun, 1993. 193(1): p. 161–6.

398. Wiseman, H., *Vitamin D is a membrane antioxidant. Ability to inhibit iron-dependent lipid peroxidation in liposomes compared to cholesterol, ergosterol and tamoxifen and relevance to anticancer action.* FEBS Lett, 1993. 326(1–3): p. 285–8.

399. Oikawa, T., et al., *Inhibition of angiogenesis by vitamin D3 analogues [**published erratum appears in Eur J Pharmacol 1990 July 17;182(3):616].* Eur J Pharmacol, 1990. 178(2): p. 247–50.

400. Colston, K. W., U. Berger, and R. C. Coombes, *Possible role for vitamin D in controlling breast cancer cell proliferation.* Lancet, 1989. 1(8631): p. 188–91.

401. DeLuca, H. F., *New concepts of vitamin D functions.* Ann N Y Acad Sci, 1992. 669: p. 59–68; discussion 68–9.

402. Abe, E., Miyaura, C., Sakagami, H., Takeda, M., et al., *Differentiation of mouse myeloid leukemia cells induced by 1-alpha, 25-hydroxyvitamin D3.* Proc. Natl. Acad. Sci. USA, 1981. 78: p. 4990–4994.

403. Petkovich, P. M., et al., *1,25-Dihydroxyvitamin D3 increases epidermal growth factor receptors and transforming growth factor beta-like activity in a bone-derived cell line.* J Biol Chem, 1987. 262(28): p. 13424–8.

404. Naveilhan, P., et al., *Induction of glioma cell death by 1,25(OH)2 vitamin D3: towards an endocrine therapy of brain tumors?* J Neurosci Res, 1994. 37(2): p. 271–7.

405. James, S. J., A. G. Basnakian, and B. J. Miller, *In vitro folate deficiency induces deoxynucleotide pool imbalance, apoptosis, and mutagenesis in Chinese hamster ovary cells.* Cancer Res, 1994. 54(19): p. 5075–80.

406. Blount, B. C. and B. N. Ames, *DNA damage infolate deficiency.* Baillieres Clin Haematol, 1995. 8: p. 461–478.

407. Jennings, E., *Folic acid as a cancer-preventing agent.* Med. Hypotheses, 1995. 45: p. 297–303.

408. Pogribny, I. P., et al., *Breaks in genomic DNA and within the p53 gene are associated with hypomethylation in livers of folate/methyl-deficient rats [published erratum appears in Cancer Res 1995 June 15;55(12):2711].* Cancer Res, 1995. 55(9): p. 1894–901.

409. Wainfan, E. and L. A. Poirier, *Methyl groups in carcinogenesis: effects on DNA methylation and gene expression.* Cancer Res, 1992. 52(7 Suppl): p. 2071s–2077s.

410. Ahuja, N., et al., *Association between CpG island methylation and microsatellite instability in colorectal cancer.* Cancer Res, 1997. 57(16): p. 3370–4.

411. Lengauer, C., K. W. Kinzler, and B. Vogelstein, *Genetic instability in colorectal cancers.* Nature, 1997. 386 (6625): p. 623–7.

412, Lengauer, C., K. W. Kinzler, and B. Vogelstein, *DNA methylation and genetic instability in colorectal cancer cells [see comments].* Proc Natl Acad Sci USA, 1997. 94(6): p. 2545–50.

413. Gama-Sosa, M. S., Slagel, V. A., Trewyn, R. W., et al., *The 5-methylcytosine content of DNA from human tumors.* Nucleic Acids Res., 1990. 11: p. 6883–6894.

414. Laird, P. W. and R. Jaenisch, *DNA methylation and cancer.* Hum Mol Genet, 1994. 3(Spec No): p. 1487–95.

415. Vogelstein, B., et al., *Genetic alterations during colorectal-tumor development.* N Engl J Med, 1988. 319 (9): p. 525–32.

416. Kim, Y. I., et al., *Global DNA hypomethylation increases progressively in cervical dysplasia and carcinoma.* Cancer, 1994. 74(3): p. 893–9.

417. Cooper, A. J., *Biochemistry of sulfur-containing amino acids.* Annu Rev Biochem, 1983.52: p. 187–222.

418. Giovannucci, E., et al., *Multivitamin use, folate, and colon cancer in women in the Nurses' Health Study [see comments].* Ann Intern Med, 1998. 129(7): p. 517–24.

419. Baron, J. A., et al., *Folate intake, alcohol consumption, cigarette smoking, and risk of colorectal adenomas.* J Natl Cancer Inst, 1998. 90(1): p. 57–62.

420. Lashner, B. A., et al., *Effect of folate supplementation on the incidence of dysplasia and cancer in chronic ulcerative colitis. A case-control study [see comments].* Gastroenterology, 1989. 97(2): p. 255–9.

421. Benito, E., et al., *Diet and colorectal adenomas: a case-control study in Majorca.* Int J Cancer, 1993. 55(2): p. 213–9.

422. Bird, C. L., et al., *Red cell and plasma folate, folate consumption, and the risk of colorectal adenomatous polyps.* Cancer Epidemiol Biomarkers Prev, 1995. 4(7): p. 709–14.

423. Paspatis, G. A., et al., *Folate status and adenomatous colonic polyps. A colonoscopically controlled study.* Dis Colon Rectum, 1995. 38(1): p. 64–7; discussion 67–8.

424. Glynn, S. A., et al., *Colorectal cancer and folate status: a nested case-control study among male smokers.* Cancer Epidemiol Biomarkers Prev, 1996. 5(7): p. 487–94.

425. Tseng, M., et al., *Micronutrients and the risk of colorectal adenomas [see comments] [**published erratum appears in Am J Epidemiol 1997 November 1;146 (9):788].* Am J Epidemiol, 1996. 144(11): p. 1005–14.

426. White, E., J. S. Shannon, and R. E. Patterson, *Relationship between vitamin and calcium supplement use and colon cancer.* Cancer Epidemiol Biomarkers Prev, 1997. 6(10): p. 769–74.

427. Kato, I., et al., *Serum folate, homocysteine and colorectal cancer risk in women: a nested case-control study.* Br J Cancer, 1999. 79(11–12): p. 1917–22.

428. Ma, J., et al., *A polymorphism of the methionine synthase gene: association with plasma folate, vitamin B12, homocyst(e)ine, and colorectal cancer risk.* Cancer Epidemiol Biomarkers Prev, 1999. 8(9): p. 825–9.

429. Slattery, M. L., et al., *Methylenetetrahydrofolate reductase, diet, and risk of colon cancer.* Cancer Epidemiol Biomarkers Prev, 1999. 8(6): p. 513–8.

430. Hillman, R. S., *Chapter 53 Hematopoetic Agents: Growth Factors, Minerals and Vitamins, in Goodman & Gillman's The Pharmacological Basis of Therapeutics, Ninth Edition,* J. G. Hardman, Limbird, L. E., Molinoff, P. B., Ruddon, R. W. and Gillman, A. G., Editor. 1996, McGraw-Hill: New York. p. 1311–1340.

431. Marcus, R. a. C., A. M., *Chapter 62 Water-Soluble Vitamins, in Goodman & Gillman's The Pharmacological Basis of Therapeutics, Ninth Edition,* J. G. Hardman, Limbird, L. E., Molinoff, P. B., Ruddon, R. W. and Gillman, A. G., Editor. 1996, McGraw-Hill: New York. p. 1555–1572.

432. NCI, D., *Clinical Development Plan: Folic Acid.* J. Cell. Biochemistry, 1996. 26S:p. 100–113.

433. World Cancer Research Fund (WCRF) Panel (Potter J. D., C., *Diet, nutrition, and the prevention of cancer: a global perspective.* 1996, Washington D.C.: WCRF/ American Institute of Cancer Research.

434. Hercberg, S., et al., *The potential role of antioxidant vitamins in preventing cardiovascular diseases and cancers.* Nutrition, 1998. 14(6): p. 513–20.

435. Slattery, M. L., et al., *Diet diversity, diet composition, and risk of colon cancer (United States).* Cancer Causes Control, 1997. 8(6): p. 872–82.

436. Slattery, M. L., et al., *Eating patterns and risk of colon cancer [see comments].* Am J Epidemiol, 1998. 148(1): p. 4–16.

What is claimed is:

1. A combination of nutrients useful in reducing colorectal cancer risk in a mammalian subject, said combination consisting essentially of the nutrient ingredients specified below, and wherein each nutrient ingredient is contained in a measured amount such that the proportional amount of each respective nutrient ingredient, relative to the other nutrient ingredient measured amounts in the combination, is as follows:

Salicin: 20–200 mg

Curcumin: 5–50 mg

Calcium: 200–2500 mg

Vitamin D: 100–1000 IU

Folic Acid: 200–1000 mcg

Vitamin $B_6$: 0.5–10 mg

Vitamin $B_{12}$: 0.1–100 mcg.

2. The combination of claim 1, wherein said nutrient ingredients are packaged together with instructions directing the administration of the combination to said subject.

3. The combination of claim 1, wherein said salicin nutrient ingredient comprises salicin from a white willow bark extract at a concentration of about 15% salicin.

4. The combination of claim 1, wherein said Curcumin nutrient ingredient comprises curcumin from a turmeric extract.

5. The combination of claim 1, wherein said Calcium nutrient ingredient is in the form of calcium carbonate.

6. The combination of claim 1, wherein said Vitamin D nutrient ingredient is in the form of vitamin $D_3$.

7. The combination of claim 1, wherein said Vitamin $B_6$ nutrient ingredient is in the form of pyridoxine or a salt thereof.

8. The combination of claim 1, wherein said nutrient ingredients are formulated together in a unit dosage form.

9. The combination of claim 1, wherein said nutrient ingredients are packaged together, and wherein a first one or more of said nutrient ingredients are formulated in a first unit dosage form and a second one or more of said nutrient ingredients are formulated in a second unit dosage form.

10. The combination of claim 2, wherein said instructions specify a timing schedule for the administration of said nutrient ingredients of the combination.

11. The combination of claim 10, wherein said instructions specify a timing schedule whereby daily amounts of said nutrient ingredients of said combination are administered to said subject as follows, within a tolerance of ±20% for each listed amount:

Salicin: 120 mg daily

Curcumin: 10 mg daily

Calcium: 800 mg daily

Vitamin D: 400 IU daily

Folic Acid: 800 mcg daily

Vitamin $B_6$: 2 mg daily

Vitamin $B_{12}$: 6 mcg daily.

12. The combination of claim 11, wherein said instructions specify administration of said daily amounts in two or more fractional portions over the course of a given day.

* * * * *